(12) United States Patent
Hennequin et al.

(10) Patent No.: US 7,262,201 B1
(45) Date of Patent: Aug. 28, 2007

(54) QUINAZOLINE DERIVATIVES

(75) Inventors: Laurent F A Hennequin, Reims (FR); Georges Pasquet, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/806,836

(22) PCT Filed: Oct. 5, 1999

(86) PCT No.: PCT/GB99/03295
§ 371 (c)(1),
(2), (4) Date: Jun. 12, 2001

(87) PCT Pub. No.: WO00/21955
PCT Pub. Date: Apr. 20, 2000

(30) Foreign Application Priority Data

Oct. 8, 1998 (EP) .................................. 98402496

(51) Int. Cl.
*A61K 31/5377* (2006.01)
*A61K 31/517* (2006.01)
*C07D 403/12* (2006.01)
*C07D 403/14* (2006.01)
*C07D 405/14* (2006.01)

(52) U.S. Cl. .............................. 514/266.3; 514/234.5; 514/266.2; 514/266.4; 544/116; 544/284; 544/287; 544/293

(58) Field of Classification Search ............. 514/234.5, 514/266.2, 266.3, 266.4; 544/116, 284, 287, 544/293
See application file for complete search history.

(56) References Cited

U.S. PATENT DOCUMENTS

| | | | |
|---|---|---|---|
| 5,409,930 A | 4/1995 | Spada et al. ................. | 514/248 |
| 5,411,963 A | 5/1995 | Dreikorn et al. ............ | 514/259 |
| 5,480,883 A | 1/1996 | Spada et al. ................. | 514/249 |
| 5,571,815 A | 11/1996 | Schaper et al. ............. | 514/269 |
| 5,646,153 A | 7/1997 | Spada et al. ................. | 514/259 |
| 5,710,158 A | 1/1998 | Myers et al. ................ | 514/259 |
| 5,714,493 A | 2/1998 | Myers et al. ................ | 514/259 |
| 5,721,237 A | 2/1998 | Myers et al. ................ | 514/259 |
| RE36,256 E | 7/1999 | Spada et al. ................. | 514/249 |
| 6,057,320 A | 5/2000 | Spada et al. ................. | 514/249 |

(Continued)

FOREIGN PATENT DOCUMENTS

DE 2213558 10/1972

(Continued)

OTHER PUBLICATIONS

Lewis, R.J., Sr. Hawley's Condensed Chemical Dictionary, 12th Edition, (c) 1993, Van Nostrand Reinhold publishing company, New York, NY., p. 1145.*

(Continued)

*Primary Examiner*—Emily Bernhardt
*Assistant Examiner*—Tamthom N. Truong
(74) *Attorney, Agent, or Firm*—Morgan Lewis & Bockius LLP

(57) ABSTRACT

The invention relates to the use of compounds of the formula I:

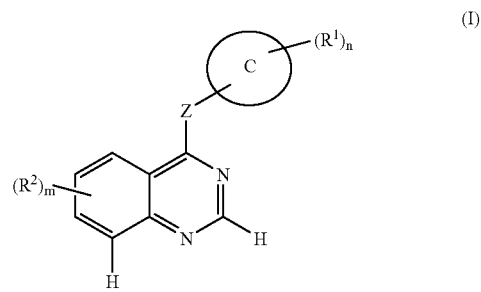

wherein: ring C is a 5-6 membered heterocyclic moiety; Z is —O—, —S—, or —$CH_2$—; $R^1$ is hydrogen, $C_{1-4}$alkyl, $C_{1-4}$alkoxymethyl, di($C_{1-4}$)alkoxy)methyl, $C_{1-4}$alkanoyl, trifluoromethyl, cyano, amino, $C_{2-5}$alkenyl, $C_{2-5}$alkynyl, carboxy, $C_{3-7}$cycloalkyl, $C_{3-7}$-cycloalkyl$C_{1-3}$alkyl, or an optionally substituted group selected from phenyl, benzyl, phenyl$C_{2-4}$alkyl and a 5-6 membered heterocyclic group; n is an integer from 0 to 5; m is an integer from 0 to 3; $R^2$ represents hydrogen, hydroxy, halgeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or $R^5X^1$— (wherein $X^1$ represents a direct bond, —$CH_2$—, or a heteroatom linker group and $R^5$ is an alkyl, alkenyl or alkynyl chain optionally substituted by for example hydroxy, amino, nitro, alkyl, cycloalkyl, alkoxyalkyl, or an optionally substituted group selected from pyridone, phenyl and a heterocyclic ring, which alkyl, alkenyl or alkynyl chain may have a heteroatom linker group, or $R^5$ is an optionally substituted group selected from pyridone, phenyl and a heterocyclic ring, and salts thereof, in the manufacture of a medicament for use in the production of an antiangiogenic and/or vascular permeability reducing effect in warm-blooded animals, processes for the preparation of such compounds, pharmaceutical compositions containing a compound of formula I or a pharmaceutically acceptable salt thereof as active ingredient and compounds of formula I. The compounds of formula I and the pharmaceutically acceptable salts thereof inhibit the effects of VEGF, a property of value in the treatment of a number of disease states including cancer and rheumatoid arthritis.

10 Claims, No Drawings

U.S. PATENT DOCUMENTS 6,645,969 B1 * 11/2003 Myers et al. ............ 514/230.5
6,649,635 B2 * 11/2003 McMahon et al. .......... 514/340

FOREIGN PATENT DOCUMENTS

| EP | 0326330 A2 | 8/1989 |
|---|---|---|
| EP | 0743308 A2 | 11/1996 |
| WO | 87/04321 | 7/1987 |
| WO | 87-04321 * | 7/1987 |
| WO | 92/16527 | 10/1992 |
| WO | 92/20642 | 11/1992 |
| WO | WO95/15758 | 6/1995 |
| WO | 95/19774 | 7/1995 |
| WO | 96/14331 | 5/1996 |
| WO | 96/30370 | 10/1996 |
| WO | WO96/39145 | 12/1996 |
| WO | 97/03069 | 1/1997 |
| WO | 97/17329 | 5/1997 |
| WO | 98/02434 | 1/1998 |
| WO | 98/14431 | 4/1998 |
| WO | 99/09016 | 1/1999 |
| WO | 99/35146 | 7/1999 |
| WO | WO99/35132 | 7/1999 |
| WO | 00/44728 | 8/2000 |

OTHER PUBLICATIONS

Mohammadi et. al. The EMBO Journal, 1998, vol. 17, No. 20, pp. 5896-5904.*

Brower V., "Tumor angiogenesis—new drugs on the block", Nature Biotechnology, vol. 17, Oct. 1999, pp. 963-968.*

Shawver et al., "Receptor tyrosine kinases as targets for inhibition of angiogenesis", DDT, vol. 2, Feb. 1997, pp. 50-63.

Kumar, "Reactions of Diazines with Nucleophiles-IV. The Reactivity of 5-Bromo-1,3,6-trimethyluracil with Thiolate ions-Substitution Versus X-Philic Versus Single Electron Transfer Reactions", Bioorg. & Med. Chem., 1995, 3, 7, 891-897.

* cited by examiner

QUINAZOLINE DERIVATIVES

This application is the National Phase of International Application PCT/GB99/03295 filed Oct. 5, 1999 which designated the U.S. and that International Application The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844). Basis FGF (bFGF) is a potent stimulator of angiogenesis (e.g. Hayek et al, 1987, Biochem. Biophys. Res. Commun. 147: 876-880) and raised levels of FGFs have been found in the serum (Fujimoto et al, 1991, Biochem. Biophys. Res. Commun. 180:386-392) and urine (Nguyen et al, 1993, J. Natl. Cancer. Inst. 85:241-242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tryposin kinase receptor, Flt4. Two of these related RTKs, Flt and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. Compounds of the present invention generally possess higher potency against VEGF receptor tyrosine kinase than against epidermal growth factor (EGF) receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase. Compounds of the present invention generally possess higher potency against VEGF receptor tyrosine kinase than against FGF R1 receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against FGF R1 receptor tyrosine kinase.

According to one aspect of the present invention there is provided the use of compounds of the formula I:

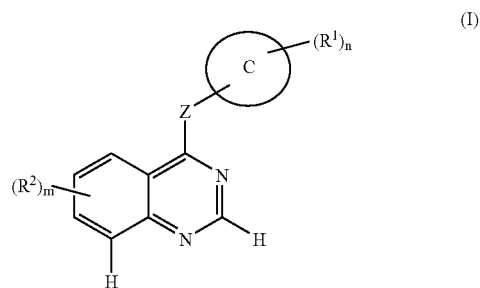

wherein:
   ring C is a 5-6 membered heterocyclic moiety which may be saturated or unsaturated, which may be aromatic or non-aromatic, and which contains 1-3 heteroatoms selected independently from O, N and S;
   Z is —O—, —NH—, —S— or —CH$_2$—;
   R$^1$ represents hydrogen, C$_{1-4}$alkyl, C$_{1-4}$alkoxymethyl, di(C$_{1-4}$)alkoxy)methyl, C$_{1-4}$alkanoyl, trifluoromethyl, cyano, amino, C$_{2-5}$alkenyl, C$_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogen, C$_{1-3}$alkyl, C$_{1-3}$alkoxy, C$_{1-3}$alkanoyloxy, trifluoromethyl, cyano, amino, nitro, C$_{2-4}$alkanoyl, $C_{1-4}$alkanoylamino, $C_{1-4}$alkoxycarbonyl, $C_{1-1}$alkylsulphanyl, $C_{1-4}$alkylsulphinyl, $C_{1-4}$alkylsulphonyl, carbamoyl, $\underline{N}$-$C_{1-4}$alkylcarbamoyl, $\underline{N},\underline{N}$-di($C_{1-4}$alkyl)carbamoyl, aminosulphonyl, $\underline{N}$-$C_{1-4}$alkylaminosulphonyl, $\underline{N},\underline{N}$-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl, and additionally substituents on the phenyl, benzyl or heterocyclic group may be selected from $C_{1-4}$alkylamino, $C_{1-4}$hydroxyalkyl, $C_{1-4}$-aminoalkyl, $C_{1-4}$haloalkyl, $C_{1-4}$hydroxyalkoxy and carboxy; and additionally $R^1$ may represent carboxy, $C_{3-7}$cycloalkyl, $C_{3-7}$cycloalkyl$C_{1-3}$alkyl, or phenyl$C_{2-4}$alkyl wherein the phenyl moiety may bear up to 5 substituents selected from the list hereinbefore defined for a phenyl ring which is directly linked to ring C;

n is an integer from 0 to 5;

m is an integer from 0 to 3;

$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or$R^5X^1$— (wherein $X^1$ represents a direct bond, —O—, —$CH_2$—, —OCO—, carbonyl, —S—, —SO—, —$SO_2$—, —$NR^6$CO—, —$CONR^7$—, —$SO_2NR^8$—, —$NR^9SO_2$— or —$NR^{10}$— (wherein $R^6$, $R^7$, $R^8$, $R^9$ and $R^{10}$ each independently represents hydrogen, $C_{1-3}$alkyl or $C_{1-3}$alkoxy$C_{2-3}$alkyl), and $R^5$ is selected from one of the following seventeen groups:

1) hydrogen or $C_{1-5}$alkyl which may be unsubstituted or which may be substituted with one or more groups selected from hydroxy, fluoro and amino, and additionally chloro and bromo;
2) $C_{1-5}$alkyl$X^2COR^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-3}$alkyl or $C_{1-3}$alkoxy$C_{2-3}$alkyl, or $C_{4-5}$alkyl));
3) $C_{1-5}$alkyl$X^3R^{16}$ (wherein $X^3$ represents —O—, —S—, —SO—, —$SO_2$—, —OCO—, —$NR^{17}$CO—, —$CONR^{18}$, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$-alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy, and additional possible substituents for the cyclic group are $C_{1-4}$cyanoalkyl and $C_{1-4}$alkoxycarbonyl);
4) $C_{1-5}$-alkyl$X^4C_{1-5}$alkyl$X^5R^{22}$ (wherein $X^4$ and $X^5$ which may be the same or different are each —O—, —S—, —SO—, —$SO_2$—, —$NR^{23}$CO—, —$CONR^{24}$—, —$SO_2NR^{25}$—, —$NR^{26}SO_2$— or —$NR^{27}$— (wherein $R^{23}$, $R^{24}$, $R^{25}$, $R^{26}$ and $R^{27}$ each independently represents hydrogen, $C_{1-3}$alkyl, or $C_{1-3}$alkoxy$C_{2-3}$alkyl) and $R^{22}$ represents hydrogen or $C_{1-3}$alkyl, or $R^{22}$ represents $C_{1-3}$alkoxy$C_{2-3}$alkyl);
5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl, and an additional possible substituent is $C_{1-4}$alkoxycarbonyl);
6) $C_{1-5}$alkyl$R^{28}$ (wherein $R^{28}$ is as defined hereinbefore);
7) $C_{2-5}$alkenyl$R^{28}$ (wherein $R^{28}$ is as defined hereinbefore);
8) $C_{2-5}$alkynyl$R^{28}$ (wherein $R^{28}$ is as defined hereinbefore);
9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogen, amino $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{30}R^{31}$ and —$NR^{32}COR^{33}$ (where $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl));
10) $C_{1-3}$alkyl$R^{29}$ (wherein $R^{29}$ is as defined hereinbefore);
11) $C_{2-5}$alkenyl$R^{29}$ (wherein $R^{29}$ is as defined hereinbefore);
12) $C_{2-5}$alkynyl$R^{29}$ (wherein $R^{29}$ is as defined hereinbefore);
13) $C_{1-5}$alkyl$X^6R^{29}$ (wherein $X^6$ represents —O—, —S—, —SO—, —$SO_2$—, —$NR^{34}$CO—, —$CONR^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);
14) $C_{2-5}$alkenyl$X^7R^{29}$ (wherein $X^7$ represents —O—, —S—, —SO—, —$SO_2$—, —$NR^{39}$CO—, —$CONR^{40}$—, —$SO_2NR^{41}$—, —$NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);
15) $C_{2-5}$alkynyl$X^8R^{29}$ (wherein $X^8$ represents —O—, —S—, —SO—, —$SO_2$—, —$NR^{44}$CO—, —$CONR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);
16) $C_{1-3}$alkyl$X^9C_{1-3}$alkyl$R^{29}$ (wherein $X^9$ represents —O—, —S—, —SO—, —$SO_2$—, —$NR^{49}$CO—, —$CONR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore); and
17) $C_{1-3}$alkyl$X^9C_{1-3}$alkyl$R^{28}$ (wherein $X^9$ $^{and\ R^{28}}$ are as defined hereinbefore); and additionally $R^5$ may be selected from a group;
18) $C_{1-3}$alkyl$R^{54}C_{1-3}$alkyl$X^9R^{55}$ (wherein $X^9$ is as defined hereinbefore and $R^{54}$ and $R^{55}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$cyanoalkyl and $C_{1-4}$alkoxycarbonyl), with the proviso that $R^{54}$ cannot be hydrogen;

and additionally wherein any $C_{1-3}$alkyl, $C_{2-5}$alkenyl or $C_{2-5}$alkynyl group in $R^5X^1$— may bear one and salts thereof, and prodrugs thereof for example esters, amides and sulphides, preferably esters and amides, in the manufacture of a medicament for use in the production of an antiangiogenic and/or vascular permeability reducing effect in warm-blooded animals such as humans.

Preferably ring C is a 5-6-membered heteroaromatic moiety which contains 1-3 heteroatoms selected independently from O, N and S.

More preferably ring C is a 5-membered heteroaromatic moiety which contains 1-3 heteroatoms selected independently from O, N and S.

Especially ring C is pyrazolyl.

Particularly ring C is pyrazolyl wherein the substituent at the 4-position of the pyrazolyl ring is hydrogen.

Preferably Z is —O— or —S—, especially —O—.

In another preferred embodiment of the invention Z is —O— or —NH—.

Preferably $R^1$ represents a phenyl group, a benzyl group or a 5-6-membered heteroaromatic group with 1-3 heteroatoms, selected independently from O, S and N, (linked via a ring carbon atom), which phenyl, benzyl or heteroaromatic group may be substituted as defined hereinbefore. Preferred 5-6-membered heteroaromatic groups contain one or two N atoms (for example, pyrrole, pyridine, pyrazole, imidazole, pyrimidine, pyrazine and pyridazine), two N atoms and one S atom (for example 1,2,5- and 1,3,4-thiadizole), one N and one O atom (for example oxazole, isoxazole and oxazine), one N and one S atom (for example thiazole and isothiazole) and one O or one S atom (furan and thiophene0.

More preferably $R^1$ is a phenyl group or a 5-6-membered heteroaromatic group with 1-3 heteroatoms, selected independently from O, S and N, (linked via a ring carbon atom), which phenyl or heteroaromatic group is optionally substituted as hereinbefore defined.

Especially $R^1$ is phenyl optionally substituted as hereinbefore defined.

In another preferred embodiment of the invention $R^1$ is a phenyl, thienyl or a furyl group which phenyl, thienyl or furyl group is optionally substituted as hereinbefore defined.

In another preferred embodiment of the invention $R^1$ is a phenyl or a furyl group which phenyl or furyl group is optionally substituted as hereinbefore defined.

Preferably the substituents on an available ring carbon atom in $R^1$ are selected independently from halogeno, $C_{1-2}$alkyl, $C_{1-2}$alkoxy, trifluoromethyl, cyano, nitro, $C_{2-3}$alkanoyl, $C_{1-3}$alkanoylamino, $C_{1-3}$alkoxycarbonyl, $C_{1-3}$alkylsulphanyl, $C_{1-3}$alkylsulphinyl, $C_{1-3}$alkylsulphonyl, carbamoyl, N-$C_{1-3}$alkylcarbamoyl, N,N-di($C_{1-3}$alkyl)aminosulphonyl, $C_{1-3}$alkylsulphonylamino, and a saturated heterocyclic group selected from morpholino, thiomorpholino, pyrrolidin-1-yl, piperazin-1-yl, piperazin-4-yl, and piperidino which saturated heterocyclic group may be substituted as hereinbefore defined.

More preferably the substituents on an available ring carbon atom in $R^1$ are selected independently from halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl, and a saturated heterocyclic group selected from morpholino, thiomorpholino, pyrrolidin-1-yl, piperazin-1-yl, piperazin-4-yl, and piperidino which saturated heterocyclic group is unsubstituted.

In another more preferred embodiment of the invention the substituents on an available ring carbon atom in $R^1$ are selected independently from $C_{1-2}$alkyl, $C_{1-2}$-alkoxy, halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl) aminosulphonyl, and a saturated heterocyclic group selected from morpholino, thiomorpholino, pyrrolidin-1-yl, piperazin-1-yl, piperazin-4-yl, and piperidino which saturated heterocyclic group is unsubstituted.

Preferably n is 1.

Preferably m is an integer from 0 to 2, more preferably 1 or 2, most preferably 2.

Advantageously $X^1$ represents —O—, —S—, —NR$^6$CO—, —NR$^9$SO$_2$— or —NR$^{10}$— (wherein $R^6$, $R^9$ and $R^{10}$ each independently represents hydrogen, $C_{1-2}$alkyl or $C_{1-2}$alkoxyethyl).

Preferably $X^1$ represents —O—, —S—, —NR$^6$CO—, —NR$^9$SO$_2$— (wherein $R^6$ and $R^9$ each independently represents hydrogen or $C_{1-2}$alkyl) or NH.

More preferably $X^1$ represents —O—, —S—, —NR$^6$CO— (wherein $R^6$ represents hydrogen or $C_{1-2}$alkyl) or NH.

Particularly $X^1$ represents —O— or —NR$^6$CO— (wherein $R^6$ represents hydrogen or $C_{1-2}$alkyl), more particularly —O— or —NHCO—, especially —O—.

Advantageously $X^2$ represents —O— or NR$^{12}$ (wherein $R^{12}$ represents hydrogen, $C_{1-3}$alkyl or $C_{1-2}$alkoxyethyl).

Advantageously $X^3$ represents —O—, —S—, —SO—, —SO$_2$—, —NR$^{17}$CO—, —NR$^{20}$SO$_2$— or —NR$^{21}$— (wherein $R^{17}$, $R^{20}$ and $R^{21}$ each independently represents hydrogen, $C_{1-2}$alkyl or $C_{1-2}$alkoxyethyl).

Preferably $X^3$ represents —O—, —S—, —SO—, —SO$_2$— or —NR$^{21}$— (wherein $R^{21}$ represents hydrogen, $C_{1-2}$alkyl or $C_{1-2}$alkoxyethyl).

More preferably $X^3$ represents —O— or —NR$^{21}$— (wherein $R^{21}$ represents hydrogen or $C_{1-2}$alkyl).

Advantageously $X^4$ and $X^5$ which may be the same or different each represents —O—, —S—, —SO—, —SO$_2$— or —NR$^{27}$— (wherein $R^{27}$ represents hydrogen, $C_{1-3}$alkyl or $C_{1-2}$alkoxyethyl).

Preferably $X^4$ and $X^5$ which may be the same or different each represents —O—, —S— or —NR$^{27}$— (wherein $R^{27}$ represents hydrogen, $C_{1-2}$alkyl or $C_{1-2}$alkoxyethyl).

More preferably $X^4$ and $X^5$ which may be the same or different each represents —O— or —NH—.

Advantageously $X^6$ represents —O—, —S— or —NR$^{38}$— (wherein $R^{38}$ represents hydrogen, $C_{1-2}$-alkyl or $C_{1-2}$alkoxyethyl).

Preferably $X^6$ represents —O— or —NR$^{38}$— (wherein $R^{38}$ represents hydrogen or $C_{1-2}$alkyl).

Advantageously $X^7$ represents —O—, —S— or —NR$^{43}$— (wherein $R^{43}$ represents hydrogen, $C_{1-2}$-alkyl or $C_{1-2}$alkoxyethyl).

Preferably $X^7$ represents —O— or —$NR^{43}$— (wherein $R^{43}$ represents hydrogen or $C_{1-2}$alkyl).

Advantageously $X^8$ represents —O—, —S— or —$NR^{48}$— (wherein $R^{48}$ represents hydrogen, $C_{1-2}$alkyl or $C_{1-2}$alkoxyethyl).

Preferably $X^8$ represents —O— or —$NR^{48}$— (wherein $R^{48}$ represents hydrogen or $C_{1-2}$alkyl).

Advantageously $X^9$ represents —O—, —S— or —$NR^{53}$— (wherein $R^{53}$ represents hydrogen, $C_{1-2}$alkyl or $C_{1-2}$alkoxyethyl).

Preferably $X^9$ represents —O— or —$NR^{53}$— (wherein $R^{53}$ represents hydrogen or $C_{1-2}$alkyl).

Preferably $R^{28}$ is pyrrolidinyl, piperazinyl, piperidinyl, morpholino or thiomorpholino (linked preferably via nitrogen) which group may carry 1 or 2 substituents selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl.

Preferably $R^{29}$ represents a pyridone group or a 5-6-membered aromatic heterocyclic group with 1 to 3 heteroatoms selected from O, N and S, which pyridone group or heterocyclic group may be substituted as hereinbefore defined.

Where $R^{29}$ is a 5-6-membered aromatic heterocyclic group, it preferably has 1 or 2 heteroatoms, selected from O, N and S, of which more preferably one is N, and may be substituted as hereinbefore defined.

$R^{29}$ is particularly a pyridone, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention $R^{29}$ represents a pyridone, phenyl or 5-6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{29}$, conveniently substituents are selected from halogeno, $C_{1-4}$alkyl, $C_{1-4}$alkoxy and cyano, more conveniently substituents are selected from chloro, fluoro, methyl and ethyl.

Preferably $R^{54}$ is a 5-6-membered saturated heterocyclic group with 1-2 heteroatoms, selected independently from O, S and N, which heterocyclic group is optionally substituted as hereinbefore defined.

More preferably $R^{54}$ is a 6-membered saturated heterocyclic group with 1-2 heteroatoms, selected independently from O, S and N, which heterocyclic group is optionally substituted as hereinbefore defined.

In one embodiment of the present invention $R^{54}$ is piperidinyl, pyrrolidinyl or piperazinyl, which group is optionally substituted as hereinbefore defined.

Preferably $R^{55}$ is $C_{1-3}$alkyl or a 5-6-membered saturated heterocyclic group with 1-2 heteroatoms, selected independently from O, S and N, which heterocyclic group is optionally substituted as hereinbefore defined.

More preferably $R^{55}$ is a 5-6-membered saturated heterocyclic group with 1-2 heteroatoms, selected independently from O, S and N, which heterocyclic group is optionally substituted as hereinbefore defined.

Especially $R^{55}$ is a group selected from morpholino, pyrrolidin-1-yl, piperidino, piperazin-1-yl and thiomorpholino which group is optionally substituted as hereinbefore defined.

Conveniently $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following seventeen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkyl$X^2COR^{11}$ (wherein $X^2$ is as hereinbefore defined and $R^{11}$ represents $C_{1-3}$alkyl, —$NR^{13}R^{14}$ or —$OR^{15}$ (wherein $R^{13}$, $R^{14}$ and $R^{15}$ which may be the same or different are each $C_{1-2}$alkyl or $C_{1-2}$alkoxyethyl));
3) $C_{2-4}$alkyl$X^3R^{16}$ (wherein $X^3$ is as hereinbefore defined and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $C_{1-5}$alkyl$R^{56}$ (wherein $R^{56}$ is a 5-6-membered saturated heterocyclic group with 1-2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl) or $C_{2-5}$alkyl$R^{57}$ (wherein $R^{57}$ is a 5-6-membered saturated heterocyclic group with 1-2 heteroatoms of which one is N and the other is selected independently from O, S and N, which heterocyclic group is linked to $C_{2-5}$alkyl through a nitrogen atom and which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);
6) $C_{3-4}$alkenyl$R^{58}$ (wherein $R^{58}$ represents $R^{56}$ or $R^{57}$ as defined hereinbefore);
7) $C_{3-4}$alkynyl$R^{58}$ (wherein $R^{58}$ represents $R^{56}$ or $R^{57}$ as defined hereinbefore);
8) $R^{29}$ (wherein $R^{29}$ represents $R^{56}$ or $R^{57}$ as defined hereinbefore);
9) $C_{1-5}$alkyl$R^{29}$ (wherein $R^{29}$ is as defined hereinbefore);
10) $C_{3-5}$alkynyl$R^{29}$ (wherein $R^{29}$ is as defined hereinbefore);
11) $C_{3-5}$alkynyl$R^{29}$ (wherein $R^{29}$ is as defined hereinbefore);
12) $C_{1-5}$alkyl$X^6R^{29}$ (wherein $X^6$ and $R^{29}$ are as defined hereinbefore);
13) $C_{4-5}$alkenyl$X^7R^{29}$ (wherein $X^7$ and $R^{29}$ are as defined hereinbefore);
14) $C_{4-5}$alkynyl$X^8R^{29}$ (wherein $X^8$ and $R^{29}$ are as defined hereinbefore);
15) $C_{2-3}$alkyl$X^9C_{1-2}$alkyl$R^{29}$ (wherein $X^9$ and $R^{29}$ are as defined hereinbefore);
16) $R^{28}$ (wherein $R^{28}$ is as defined hereinbefore); and
17) $C_{2-3}$alkyl$X^9C_{1-2}$alkyl$R^{28}$ (wherein $X^9$ and $R^{28}$ are as defined hereinbefore); and additionally $R^5$ may be selected from a group;
18) $C_{2-3}$alkyl$R^{54}C_{1-2}$alkyl$X^9R^{55}$ (wherein $X^9$, $R^{54}$ and $R^{55}$ are as defined hereinbefore); and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Advantageously $R^2$ represents hydroxy, halogeno, nitro, trifluoromethyl, $C_{1-3}$alkyl, cyano, amino or $R^5X^1$—[wherein $X^1$ is as hereinbefore defined and $R^5$ is selected from one of the following seventeen groups;

1) $C_{1-4}$alkyl which may be unsubstituted or substituted with one or more fluorine atoms, or $C_{2-4}$alkyl which may be unsubstituted or substituted with 1 or 2 groups selected from hydroxy and amino;
2) $C_{2-3}$alkyl$X^2COR^{11}$ (wherein $X^2$ is as hereinbefore defined and $R^{11}$ represents —$NR^{13}R^{14}$ or —$OR^{15}$ (wherein $R^{13}$, $R^{14}$ and $R^{15}$ which may be the same or different are each $C_{1-2}$alkyl or $C_{1-2}$alkoxyethyl));
3) $C_{2-4}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear 1 or 2 substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $C_{1-4}$alkyl$R^{59}$ (wherein $R^{59}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry 1 or 2 substituents selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl) or $C_{2-4}$alkyl$R^{60}$ (wherein $R^{60}$ is a group selected from morpholino, thiomorpholino, pyrrolidin-1-yl, piperazin-1-yl and piperidino which group may carry 1 or 2 substituents selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl);
6) $C_{3-4}$alkenyl$R^{61}$ (wherein $R^{61}$ represents $R^{59}$ or $R^{60}$ as defined hereinbefore);
7) $C_{3-4}$alkynyl$R^{61}$ (wherein $R^{61}$ represents $R^{59}$ or $R^{60}$ as defined hereinbefore);
8) $R^{29}$ (wherein $R^{29}$ is as defined hereinbefore);
9) $C_{1-4}$alkyl$R^{29}$ (wherein $R^{29}$ is as defined hereinbefore);
10) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);
11) 1-$R^{29}$prop-1-yn-3-yl or 1-$R^{29}$but-2-yn-4-yl (wherein $R^{29}$ is as defined hereinbefore with the proviso that when $R^5$ is 1-$R^{29}$prop-1-yn-3-yl, $R^{29}$ is linked to the alkynyl group via a carbon atom);
12) $C_{1-5}$alkyl$X^6R^{29}$ (wherein $X^6$ and $R^{29}$ are as defined hereinbefore);
13) 1-($R^{29}X^7$)but-2-en-4-yl (wherein $X^7$ and $R^{29}$ are as defined hereinbefore);
14) 1-($R^{29}X^8$)but-2-yn-4-yl (wherein $X^8$ and $R^{29}$ are as defined hereinbefore);
15) $C_{2-3}$alkyl$X^9C_{1-2}$alkyl$R^{29}$ (wherein $X^9$ and $R^{29}$ are as defined hereinbefore);
16) $R^{28}$ (wherein $R^{28}$ is as defined hereinbefore); and
17) $C_{2-3}$alkyl$X^9C_{1-2}$alkyl$R^{28}$ (wherein $X^9$ and $R^{28}$ are as defined hereinbefore); and additionally $R^5$ may be selected from a group;
18) $C_{2-3}$alkyl$R^{54}C_{1-2}$alkyl$X^9R^{55}$ (wherein $X^9$, $R^{54}$ and $R^{55}$ are as defined hereinbefore); and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following fifteen groups;

1) $C_{1-3}$alkyl which may be unsubstituted or substituted with one or more fluorine atoms, or $C_{2-3}$alkyl which may be unsubstituted or substituted with 1 or 2 groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;
3) $C_{2-3}$alkyl$X^3R^{16}$ (wherein $X^3$ is as defined hereinbefore and $R^{16}$ is a group selected from $C_{1-2}$alkyl, cyclopentyl, cyclohexyl, pyrrolidinyl and piperidinyl which group is linked to $X^3$ through a carbon atom and which $C_{1-2}$alkyl group may bear 1 or 2 substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl);
5) $C_{1-2}$alkyl$R^{59}$ (wherein $R^{59}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which heterocyclic group may carry one substituent selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl) or $C_{2-3}$alkyl$R^{60}$ (wherein $R^{60}$ is a group selected from morpholino, thiomorpholino, piperidino, piperazin-1-yl and pyrrolidin-1-yl which group may carry one substituent selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl);
6) $R^{29}$ (wherein $R^{29}$ is as defined hereinbefore);
7) $C_{1-4}$alkyl$R^{29}$ (wherein $R^{29}$ is as defined hereinbefore);
8) 1-$R^{29}$but-2-en-4-yl (wherein $R^{29}$ is as defined hereinbefore);
9) 1-$R^{29}$but-2-yn-4-yl (wherein $R^{29}$ is as defined hereinbefore);
10) $C_{1-5}$alkyl$X^6R^{29}$ (wherein $X^6$ and $R^{29}$ are as defined hereinbefore);
11) 1-($R^{29}X^7$)but-2-en-4-yl (wherein $X^7$ and $R^{29}$ are as defined hereinbefore);
12) 1-($R^{29}X^8$)but-2-yn-4-yl (wherein $X^8$ and $R^{29}$ are as defined hereinbefore);
13) ethyl$X^9$methyl$R^{29}$ (wherein $X^9$ and $R^{29}$ are as defined hereinbefore);
14) $R^{28}$ (wherein $R^{28}$ is as defined hereinbefore); and
15) ethyl$X^9$methyl$R^{28}$ (wherein $X^9$ and $R^{28}$ are as defined hereinbefore); and additionally $R^5$ may be selected from a group;

16) ethylR$^{54}$methylX$^9$R$^{55}$ (wherein X$^9$, R$^{54}$ and R$^{55}$ are as defined hereinbefore); and additionally wherein any C$_{1-5}$alkyl, C$_{2-5}$alkenyl or C$_{2-5}$alkynyl group in R$^5$X$^1$— may bear one or more substituents selected from hydroxy, halogeno and amino].

More preferably R$^2$ represents C$_{1-3}$alkyl, amino or R$^5$X$^1$— [wherein X$^1$ is as hereinbefore defined and R$^5$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-3-yl)propyl, 2-(methylpiperidin-3-yl)ethyl, 2-(methylpiperidin-4-yl)ethyl, 3-(methylpiperidin-3-yl)propyl, 3-(methylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl or 3-(4-oxidomorpholino)propyl, and additionally R$^5$ may represent 2-(2-methoxyethoxy)ethyl, 1-methylpiperidin-4-ylmethyl, 1-(2-methylsulphonylethyl)piperidin-4-ylmethyl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl].

In another aspect R$^2$ represents methoxy, 2-methoxyethoxy, 2-(2-methoxyethoxy)ethoxy, 3-methoxypropoxy, 2-methylsulphonylethoxy, 3-methylsulphonylpropoxy, 2-(tetrahydropyran-4-yloxy)ethoxy, 3-(tetrahydropyran-4-yloxy)propoxy, 2-(4-methylpiperazin-1-yl)ethoxy, 3-(4-methylpiperazin-1-yl)propoxy, 2-morpholinoethoxy, 3-morpholinoethoxy, 3-morpholinopropoxy, 2-(imidazol-1-yl)ethoxy, 3-(imidazol-1-yl)propoxy 2-(1,1-dioxothiomorpholino)ethoxy, 3-(1,1-dioxothiomorpholino)propoxy, 2-(1,2,3-triazol-1-yl)ethoxy, 3-(1,2,3-triazol-1-yl)propoxy, 2-(N-methoxyacetyl-N-methylamino)ethoxy, 3-(N-methoxyacetyl-N-methylamino)propoxy, N-methylpiperidin-3-ylmethoxy, 4-(pyrrolidin-1-yl)but-2-en-yloxy, 2-(2-oxopyrrolidin-1-yl)ethoxy, 3-(2-oxopyrrolidin-1-yl)propoxy, 2-(pyrrolidin-1-yl)ethoxy, 3-(pyrrolidin-1-yl)ethoxy, 3-(pyrrolidin-1-yl)propoxy, 2-(2-(pyrrolidin-1-yl)ethoxy)ethoxy, 2-(2-(4-methylpiperazin-1-yl)ethoxy)ethoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(methylpiperidin-3-yl)ethoxy, 2-(methylpiperidin-4-yl)ethoxy, 3-(methylpiperidin-3-yl)propoxy, 3-(methylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy or 3-(1-isopropylpiperidin-4-yl)propoxy, and additionally R$^2$ may represent 3-(4-methylpiperazin-1-yl)propoxy, 1-methylpiperidin-4-ylmethoxy, 1-(2-methylsulphonylethyl)piperidin-4-ylmethoxy, 1-(2-pyrrolidinylethyl)piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy or 1-(3-azetidinylpropyl)piperidin-4-ylmethoxy.

In another aspect R$^2$ represents 2-methoxyethoxy, 2-(2-methoxyethoxy)ethoxy, 3-methoxypropoxy, 2-methylsulphonylethoxy, 3-methylsulphonylpropoxy, 2-(tetrahydropyran-4-yloxy)ethoxy, 3-(tetrahydropyran-4-yloxy)propoxy, 2-(4-methylpiperazin-1-yl)ethoxy, 3-(4-methylpiperazin-1-yl)propoxy, 2-morpholinoethoxy, 3-morpholinopropoxy, 2-(imidazol-1-yl)ethoxy, 3-(imidazol-1-yl)propoxy 2-(1,1-dioxothiomorpholino)ethoxy, 3-(1,1-dioxothiomorpholino)

propoxy, 2-(1,2,3-triazol-1-yl)ethoxy, 3-(1,2,3-triazol-1-yl)propoxy, 2-(N-methoxyacetyl-N-methylamino)ethoxy, 3-(N-methoxyacetyl-N-methylamino)propoxy, N-methylpiperidin-3-ylmethoxy, 4-(pyrrolidin-1-yl)but-2-en-yloxy, 2-(2-oxopyrrolidin-1-yl)ethoxy, 3-(2-oxopyrrolidin-1-yl)propoxy, 2-(pyrrolidin-1-yl)ethoxy, 3-(pyrrolidin-1-yl)propoxy, 2-(2-(pyrrolidin-1-yl)ethoxy)ethoxy, 2-(2-(4-methylpiperazin-1-yl)ethoxy)ethoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(methylpiperidin-3-yl)ethoxy, 2-(methylpiperidin-4-yl)ethoxy, 3-(methylpiperidin-3-yl)propoxy, 3-(methylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy or 3-(1-isopropylpiperidin-4-yl)propoxy, and additionally $R^2$ may represent 3-(4-methylpiperazin-1-yl)propoxy, 1-methylpiperidin-4-ylmethoxy, 1-(2-methylsulphonylethyl)piperidin-4-ylmethoxy, 1-(2-pyrrolidinylethyl)piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy or 1-(3-azetidinylpropyl)piperidin-4-ylmethoxy.

Where one of the $R^2$ substituents is $R^5X^1$— the substituent $R^5X^1$— is preferably at the 6- or 7-position of the quinazoline ring, more preferably at the 7-position of the quinazoline ring.

When one of the $R^2$ substituents is at the 6-position of the quinazoline ring it is preferably halogeno, $C_{1-3}$alkyl, $C_{1-3}$alkoxy, $C_{1-3}$alkylsulphanyl or —$NR^3R^4$ (wherein $R^3$ and $R^4$ are as defined hereinbefore). Another preferred value for $R^2$ at the 6-position of the quinazoline ring is hydrogen.

When one of the $R^2$ substituents is at the 6-position of the quinazoline ring it is more preferably $C_{1-3}$-alkoxy, especially methoxy.

In another aspect of the present invention there is provided the use of compounds of the formula Ia:

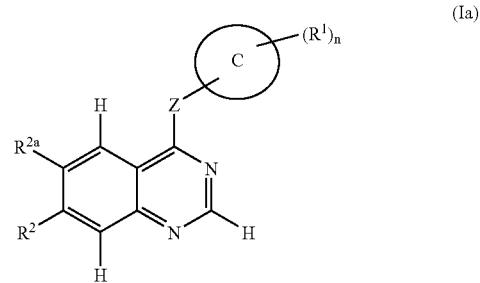

(Ia)

wherein:

ring C, $R^1$, $R^2$, n and Z are as defined hereinbefore with the proviso that $R^2$ is not hydrogen; and $R^{2a}$ represents halogeno, $C_{1-3}$alkyl, $C_{1-3}$alkoxy, $C_{1-3}$alkylthio, —$NR^{3a}R^{4a}$ (wherein $R^{3a}$ and $R^{4a}$, which may be the same or different, each represents hydrogen or $C_{1-3}$alkyl), or $R^{5a}(CH_2)_{za}X^{1a}$ (wherein $R^{5a}$ is a 5- or 6-membered saturated heterocyclic group with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl and $C_{1-4}$alkoxy, za is an integer from 0 to 4 and $X_{1a}$ represents a direct bond, —O—, —$CH_2$—, —S—, —SO—, —$SO_2$—, —$NR^{6a}CO$—, —$CONR^{7a}$—, —$SO_2NR^{8a}$—, —$NR^{9a}SO_2$— or —$NR^{10a}$— (wherein $R^{6a}$, $R^{7a}$, $R^{8a}$, $R^{9a}$ and $R^{10a}$ each independently represents hydrogen, $C_{1-3}$alkyl or $C_{1-3}$alkoxy$C_{2-3}$alkyl); or $R^{2a}$ represents hydrogen);

and salts thereof, and prodrugs thereof for example esters, amides and sulphides, preferably esters and amides, in the manufacture of a medicament for use in the production of an antiangiogenic and/or vascular permeability reducing effect in warm-blooded animals such as humans.

Advantageously $X^{1a}$ represents —O—, —S—, —$NR^{6a}CO$—, —$NR^{9a}SO_2$— or —$NR^{10a}$— (wherein $R^{6a}$, $R^{9a}$ and $R^{10a}$ each independently represents hydrogen, $C_{1-2}$alkyl or $C_{1-2}$alkoxyethyl).

Preferably $X^{1a}$ represents —O—, —S—, —$NR^{6a}CO$—, —$NR^{9a}SO_2$— (wherein $R^{6a}$ and $R^{9a}$ each independently represents hydrogen or $C_{1-2}$alkyl) or NH.

More preferably $X^{1a}$ represents —O—, —S—, —$NR^{6a}CO$— (wherein $R^{6a}$ represents hydrogen or $C_{1-2}$alkyl) or NH.

Particularly $X^{1a}$ represents —O— or —$NR^{6a}CO$— (wherein $R^{6a}$ represents hydrogen or $C_{1-2}$alkyl), more particularly —O— or —NHCO—, especially —O—.

Preferably za is an integer from 1 to 3.

Preferably $R^{5a}$ is a group selected from pyrrolidinyl, piperazinyl, piperidinyl, morpholino and thiomorpholino which group may carry 1 or 2 substituents selected from oxo, hydroxy, halogeno, $C_{1-2}$alkyl, $C_{1-2}$hydroxyalkyl and $C_{1-2}$alkoxy.

Advantageously $R^{2a}$ represents $C_{1-3}$alkyl, $C_{1-3}$alkoxy, amino or $R^{5a}(CH_2)_{za}X^{1a}$ (wherein $R^{5a}$, $X^{1a}$ and za are as defined hereinbefore). Another advantageous value of $R^{2a}$ is hydrogen.

Preferably $R^{2a}$ is methyl, ethyl, methoxy, ethoxy or $R^{5a}(CH_2)_{za}X^{1a}$ (wherein $R^{5a}$, $X^{1a}$ and za are as defined hereinbefore). Another preferred value of $R^{2a}$ is hydrogen.

More preferably $R^{2a}$ is methyl, ethyl, methoxy, ethoxy or $R^{5a}(CH_2)_{za}X^{1a}$ (wherein $R^{5a}$ is a group selected from pyrrolidinyl, piperazinyl, piperidinyl, morpholino and thiomorpholino which group may carry 1 or 2 substituents selected from oxo, hydroxy, halogeno, $C_{1-2}$alkyl, $C_{1-2}$hydroxyalkyl and $C_{1-2}$-alkoxy, $X^{1a}$ is —O—, —S—, —$NR^{6a}CO$—, —$NR^{9a}SO_2$— (wherein $R^{6a}$ and $R^{9a}$ each independently represents hydrogen or $C_{1-2}$alkyl) or NH, and za is an integer from 1 to 3). Another more preferred value of $R^{2a}$ is hydrogen.

Particularly $R^{2a}$ represents methyl, methoxy or $R^{5a}(CH_2)_{za}X^{1a}$ (wherein $R^{5a}$, $X^{1a}$ and za are as defined hereinbefore).

More particularly $R^{2a}$ represents methoxy.

In a further aspect of the present invention there is provided the use of compounds of the formula Ib:

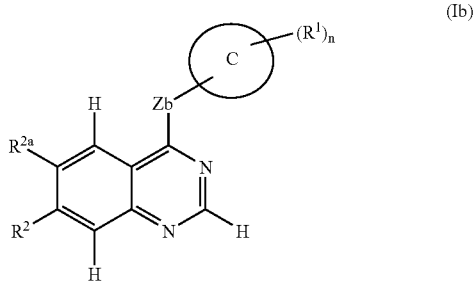

(Ib)

wherein:
ring C, $R^1$, $R^2$, $R^{2a}$ and n are as defined hereinbefore with the proviso that $R^2$ is not hydrogen; and
Zb is —O— or —S—;
and salts thereof, and prodrugs thereof for example esters, amides and sulphides, preferably esters and amides, in the manufacture of a medicament for use in the production of an antiangiogenic and/or vascular permeability reducing effect in warm-blooded animals such as humans.

Preferably Zb is —O—.

According to another aspect of the present invention there are provided compounds of the formula II:

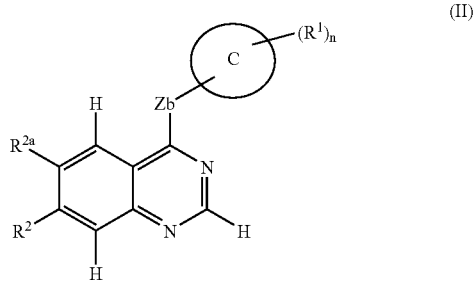

(II)

wherein:
ring C, $R^1$, $R^2$, $R^{2a}$, Zb and n are as defined hereinbefore with the proviso that $R^2$ does not have any of the following values:
hydrogen, substituted or unsubstituted $C_{1-5}$alkyl, halogeno, $C_{1-5}$alkoxy, phenoxy or phenyl$C_{1-5}$alkoxy;
and salts thereof, and prodrugs thereof for example esters, amides and sulphides, preferably esters and amides.

Preferred compounds of the present invention include
4-(5-benzylpyrazol-3-yloxy)-6-methoxy-7-(3-morpholinopropoxy)quinazoline,
7-(2-methoxyethoxy)-4-(5-phenylpyrazol-3-yloxy)quinazoline,
4-(5-butylpyrazol-3-yloxy)-6-methoxy-7-(3-morpholinopropoxy)quinazoline,
6-methoxy-7-(3-morpholinopropoxy)-4-(5-propylpyrazol-3-yloxy)quinazoline,
4-(5-methoxymethylpyrazol-3-yloxy)-6-methoxy-7-(3-morpholinopropoxy)quinazoline,
6-methoxy-7-(3-morpholinopropoxy)-4-(5-(pent-3-en-1-yl)pyrazol-3-yloxy)quinazoline,
6-methoxy-7-(3-morpholinopropoxy)-4-(5-(3-pyridyl)pyrazol-3-yloxy)quinazoline,
4-(5-isobutylpyrazol-3-yloxy)-6-methoxy-7-(3-morpholinopropoxy)quinazoline and
4-(5-(2-cyclopentylethyl)pyrazol-3-yloxy)-6-methoxy-7-(3-morpholinopropoxy)quinazoline
and salts thereof especially hydrochloride salts thereof and prodrugs thereof for example esters, amides and sulphides.

More preferred compounds of the present invention include
4-(5-(4-methoxyphenyl)pyrazol-3-yloxy)-6-methoxy-7-(1-methylpiperidin-4-ylmethoxy)quinazoline,
4-(5-(4-methoxyphenyl)pyrazol-3-yloxy)-6-methoxy-7-(3-(4-methylpiperidin-1-yl)propoxy)quinazoline,
6-methoxy-7-(2-(2-methoxyethoxy)ethoxy)-4-(5-phenylpyrazol-3-yloxy)quinazoline,
4-(5-(3-furyl)pyrazol-3-yloxy)-6-methoxy-7-(3-morpholinopropoxy)quinazoline,
6,7-dimethoxy-4-(5-phenylpyrazol-3-yloxy)quinazoline,
6-methoxy-7-(3-morpholinopropoxy)-4-(5-phenylpyrazol-3-yloxy)quinazoline,
4-(5-(2-fluorophenyl)pyrazol-3-yloxy)-6-methoxy-7-(3-morpholinopropoxy)quinazoline,
6-methoxy-7-(3-morpholinopropoxy)-4-(5-(3-nitrophenyl)pyrazol-3-yloxy)quinazoline,
6-methoxy-7-(3-morpholinopropoxy)-4-(5-(4-nitrophenyl)pyrazol-3-yloxy)quinazoline,
6-methoxy-7-(3-morpholinopropoxy)-4-(5-(4-pyridyl)pyrazol-3-yloxy)quinazoline,
7-(2-(imidazol-1-yl)ethoxy)-6-methoxy-4-(5-phenylpyrazol-3-yloxy)quinazoline and
4-(5-(4-fluorophenyl)pyrazol-3-yloxy)-6-methoxy-7-(3-morpholinopropoxy)quinazoline
and salts thereof especially hydrochloride salts thereof and prodrugs thereof for example esters, amides and sulphides.

Especially preferred compounds of the present invention include
4-(5-(4-chlorophenyl)pyrazol-3-yloxy)-6-methoxy-7-(3-morpholinopropoxy)quinazoline,
6-methoxy-7-(3-(4-methylpiperazin-1-yl)propoxy)-4-(5-phenylpyrazol-3-yloxy)quinazoline,
6-methoxy-7-(2-methoxyethoxy)-4-(5-phenylpyrazol-3-yloxy)quinazoline and
6-methoxy-7-(2-methoxyethoxy)-4-(5-(4-methoxyphenyl)pyrazol-3-yloxy)quinazoline
and salts thereof especially hydrochloride salts thereof and prodrugs thereof for example esters, amides and sulphides.

According to another especially preferred aspect of the present invention there is provided the use of a compound selected from:

6-methoxy-7-(1-methylpiperidin-4-ylmethoxy)-4-(5-phenylpyrazol-3-ylamino)quinazoline and 6,7-dimethoxy-4-(5-phenylpyrazol-3yloxy)quinazoline or a salt thereof, or a prodrug thereof for example an ester or amide, in the manufacture of a medicament for use in the production of an antiangiogenic and/or vascular permeability reducing effect in warm-blooded animals such as humans.

According to another more preferred aspect of the present invention there is provided the use of a compound selected from:

6-methoxy-4-(5-(4-methoxyphenyl)pyrazol-3-ylamino)-7-(1-methylpiperidin-4-ylmethoxy)quinazoline, 4-(5-(4-chlorophenyl)pyrazol-3-ylamino)-6-methoxy-7-(1-methylpiperidin-4-ylmethoxy)quinazoline and 6-methoxy-7-(1-methylpiperidin-4-ylmethoxy)-4-(5-(4-methylphenyl)pyrazol-3-ylamino)quinazoline, or a salt thereof, or a prodrug thereof for example an ester or amide, in the manufacture of a medicament for use in the production of an antiangiogenic and/or vascular permeability reducing effect in warm-blooded animals such as humans.

According to another preferred aspect of the present invention there is provided the use of a compound selected from:

6,7-dimethoxy-4-(5-phenylpyrazol-3-ylamino), 4-(5-(3,4-dichlorophenyl)pyrazol-3-ylamino)-6-methoxy-7-(1-methylpiperidin-4-ylmethoxy)quinazoline, 6-methoxy-7-(1-methylpiperidin-4-ylmethoxy)-4-(5-(3-trifluoromethylphenyl)pyrazol-3-ylamino)quinazoline and 4-(5-cyclopropyl)pyrazol-3-ylamino)-6-methoxy-7-(1-methylpiperidin-4-ylmethoxy)quinazoline or a salt thereof, or a prodrug thereof for example an ester or amide, in the manufacture of a medicament for use in the production of an antiangiogenic and/or vascular permeability reducing effect in warm-blooded animals such as humans.

Another especially preferred group of compounds of the present invention includes 4-(5-(4-methoxyphenyl)pyrazol-3-yloxy)-6-methoxy-7-(1-methylpiperidin-4-ylmethoxy)quinazoline, 4-(5-(4-methoxyphenyl)pyrazol-3-yloxy)-6-methoxy-7-(3-(4-methylpiperidin-1-yl)propoxy)quinazoline, 6-methoxy-7-(2-(2-methoxyethoxy)ethoxy)-4-(5-phenylpyrazol-3-yloxy)quinazoline, 4-(5-(3-furyl)pyrazol-3-yloxy)-6-methoxy-7-(3-morpholinopropoxy)quinazoline, 6-methoxy-7-(3-morpholinopropoxy)-4-(5-phenylpyrazol-3-yloxy)quinazoline, 7-(2-(imidazol-1-yl)ethoxy)-6-methoxy-4-(5-phenylpyrazol-3-yloxy)quinazoline, 4-(5-(4-chlorophenyl)pyrazol-3-yloxy)-6-methoxy-7-(3-morpholinopropoxy)quinazoline, 6-methoxy-7-(3-(4-methylpiperazin-1-yl)propoxy)-4-(5-phenylpyrazol-3-yloxy)quinazoline, 6-methoxy-7-(2-methoxyethoxy)-4-(5-phenylpyrazol-3-yloxy)quinazoline, 4-(5-(4-methoxyphenyl)pyrazol-3-yloxy)-6-methoxy-7-(2-(1,2,3-triazol-1-yl)ethoxy)quinazoline and 4-(5-(4-methoxyphenyl)pyrazol-3-yloxy)-6-methoxy-7-(1-(2-methylsulphonylethyl)piperidin-4-ylmethoxy)quinazoline, and salts thereof especially hydrochloride salts thereof and prodrugs thereof for example esters and amides.

Another more preferred group of compounds of the present invention includes 7-(2-methoxyethoxy)-4-(5-phenylpyrazol-3-yloxy)quinazoline, 4-(5-(2-fluorophenyl)pyrazol-3-yloxy)-6-methoxy-7-(3-morpholinopropoxy)quinazoline, 6-methoxy-7-(3-morpholinopropoxy)-4-(5-(3-nitrophenyl)pyrazol-3-yloxy)quinazoline, 6-methoxy-7-(3-morpholinopropoxy)-4-(5-(4-nitrophenyl)pyrazol-3-yloxy)quinazoline, 6-methoxy-7-(3-morpholinopropoxy)-4-(5-(4-pyridyl)pyrazol-3-yloxy)quinazoline, 4-(5-(4-fluorophenyl)pyrazol-3-yloxy)-6-methoxy-7-(3-morpholinopropoxy)quinazoline, and 6-methoxy-7-(2-methoxyethoxy)-4-(5-(4-methoxyphenyl)pyrazol-3-yloxy)quinazoline, and salts thereof especially hydrochloride salts thereof and prodrugs thereof for example esters and amides.

Another preferred group of compounds of the present invention includes 4-(5-benzylpyrazol-3-yloxy)-6-methoxy-7-(3-morpholinopropoxy)quinazoline, 4-(5-butylpyrazol-3-yloxy)-6-methoxy-7-(3-morpholinopropoxy)quinazoline, 6-methoxy-7-(3-morpholinopropoxy)-4-(5-propylpyrazol-3-yloxy)quinazoline, 4-(5-methoxymethylpyrazol-3-yloxy)-6-methoxy-7-(3-morpholinopropoxy)quinazoline, 6-methoxy-7-(3-morpholinopropoxy)-4-(5-(pent-3-en-1yl)pyrazol-3-yloxy)quinazoline, 6-methoxy-7-(3-morpholinopropoxy)-4-(5-(3-pyridyl)pyrazol-3-yloxy)quinazoline, 4-(5-isobutylpyrazol-3-yloxy)-6-methoxy-7-(3-morpholinopropoxy)quinazoline, 4-(5-(2-cyclopentylethyl)pyrazol-3-yloxy)-6-methoxy-7-(3-morpholinopropoxy)quinazoline, 4-(5-(3,4-dimethoxyphenyl)pyrazol-3-yloxy)-6-methoxy-7-(-3-morpholinopropoxy)quinazoline, 6-methoxy-7-(3-morpholinopropoxy)-4-(5-(pent-3-en-1-yl)pyrazol-3-yloxy)quinazoline, 6-methoxy-7-(3-morpholinopropoxy)-4-(5-(2-phenylethyl)pyrazol-3-yloxy)quinazoline, 4-(5-ethylpyrazol-3-yloxy)-6-methoxy-7-(3-morpholinopropoxy)quinazoline and 4-(5-(4-methoxyphenyl)pyrazol-3-yloxy)-6-methoxy-7-(3-methylsulphonylpropoxy)quinazoline, and salts thereof especially hydrochloride salts thereof and prodrugs thereof for example esters and amides.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl-groups but references to individual alkyl groups such as "propyl" are specific for the straight chain version only. An analogous convention applies to other generic terms. Unless otherwise stated the term "alkyl" advantageously refers to chains with 1-6 carbon atoms, preferably 1-4 carbon atoms. The term "alkoxy" as used herein, unless stated otherwise includes "alkyl"-O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"-O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2-5 carbon atoms, preferably 3-4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2-5 carbon atoms, preferably 3-4 carbon atoms.

For the avoidance of doubt it is to be understood that where $R^2$ has a value of substituted or unsubstituted $C_{1-5}$alkyl, it has been selected from $C_{1-3}$alkyl or from $R^5X^1$— wherein $R^5$ has been selected from group 1) as defined hereinbefore and wherein $X^1$ has the value —$CH_2$— or is a direct bond.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an aymmetric carbon atom. Such an asymmetric carbon atom is also involved in the tautomerism described above, and it is to be understood that the present invention encompasses any chiral form (including both pure enantiomers and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6CO$—, it is the nitrogen atom bearing the $R^6$ group which is attached to the quinazoline ring and the carbonyl (CO) group is attached to $R^5$, whereas when $X^1$ is, for example, a group of formula —$CONR^7$—, it is the carbonyl group which is attached to the quinazoline ring and the nitrogen atom bearing the $R^7$ group is attached to $R^1$. A similar convention applies to the other two atom $X^1$ linking groups such as —$NR^9SO_2$— and —$SO_2NR^8$—. When $X^1$ is —$NR^{10}$— it is the nitrogen atom bearing the $R^{10}$ group which is linked to the quinazoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-5}$alkyl$X^9C_{1-5}$alkyl$R^{29}$, it is the terminal $C_{1-5}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applied to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

The present invention relates to the compounds for formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Publication Nos. 0520722, 0566226, 0602851 and 0635498 and in International Patent Applications Publication Nos. WO 97/22596, WO 97/30035, WO 97/32856, WO 97/42187 and WO 98/13354. Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.

Synthesis of Compounds of Formula I

Compounds of the formula I and salts thereof may be prepared by the reaction of a compound of the formula III:

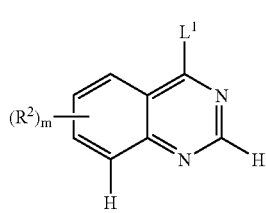

(III)

(wherein $R^2$ and m are as defined hereinbefore and $L^1$ is a displaceable moiety), with a compound of the formula IV:

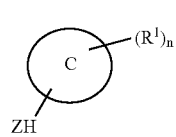

(IV)

(wherein ring C, $R^1$, Z and n are as defined hereinbefore) to obtain compounds of the formula I and salts thereof. A convenient displaceable moiety $L^1$ is, for example, a halogeno, alkoxy (preferable $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range of 20 to 90° C.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$ wherein $R^5$ is as defined hereinbefore and $X^1$ is —O—, —S—, —OCO— or —$NR^{10}$— (wherein $R^{10}$ independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula V:

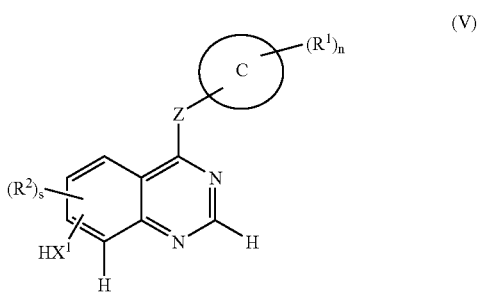

(V)

(wherein ring C, Z, $R^1$, $R^2$ and n are hereinbefore defined and $X^1$ is as hereinbefore defined in this section and s is an integer from 0 to 2) with a compound of formula VI:

$$R^5—L^1 \qquad (VI)$$

(wherein $R^5$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$ wherein $R^5$ is as defined hereinbefore and $X^1$ is —O—, —S—, —OCO— or —$NR^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

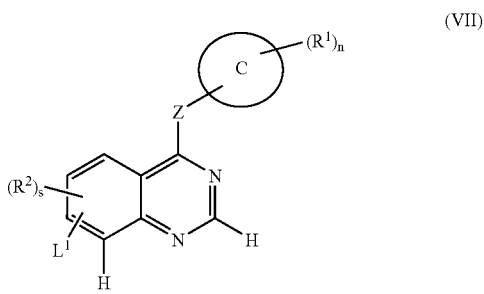

(VII)

with a compound of the formula VIII:

$$R^5—X^1—H \qquad (VIII)$$

(wherein $L^1$, $R^1$, $R^2$, $R^5$, ring C, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X^1$ wherein $X^1$ is as defined hereinbefore and $R^5$ is $C_{1-5}$alkyl$R^{62}$, wherein $R^{62}$ is selected from one of the following nine groups:
1) $X^{10}C_{1-3}$alkyl (wherein $X^{10}$ represents —O—, —S—, —SO$_2$—, —NR$^{63}$CO— or —NR$^{64}$SO$_2$— (wherein $R^{63}$ and $R^{64}$ which may be the same or different are each hydrogen, $C_{1-3}$alkyl or $C_{1-3}$alkoxy$C_{2-3}$alkyl);
2) NR$^{65}$R$^{66}$ (wherein $R^{65}$ and $R^{66}$ which may be the same or different are each hydrogen, $C_{1-3}$-alkyl or $C_{1-3}$alkoxy$C_{2-3}$alkyl);
3) $X^{11}C_{1-5}$alkyl$X^5R^{22}$ (wherein $X^{11}$ represents —O—, —S—, —SO$_2$—, —NR$^{67}$CO—, —NR$^{68}$SO$_2$— or —NR$^{69}$— (wherein $R^{67}$, $R^{68}$, and $R^{69}$ which may be the same or different are each hydrogen, $C_{1-3}$alkyl or $C_{1-3}$alkoxy$C_{2-3}$alkyl) and $X^5$ and $R^{22}$ are as defined hereinbefore);
4) $R^{28}$ (wherein $R^{28}$ is as defined hereinbefore);
5) $X^{12}R^{29}$ (wherein $X^{12}$ represents —O—, —S—, —SO$_2$—, —NR$^{70}$CO—, —NR$^{71}$SO$_2$—, or —NR$^{72}$— (wherein $R^{70}$, $R^{71}$, and $R^{72}$ which may be the same or different are each hydrogen, $C_{1-3}$alkyl or $C_{1-3}$alkoxy$C_{2-3}$ alkyl) and $R^{29}$ is as defined hereinbefore);
6) $X^{13}C_{1-5}$alkyl$R^{29}$, preferably $X^{13}C_{1-3}$alkyl$R^{29}$, (wherein $X^{13}$ represents —O—, —S—, —SO$_2$—, —NR$^{73}$CO—, —NR$^{74}$SO$_2$— or —NR$^{75}$— (wherein $R^{73}$, $R^{74}$ and $R^{75}$ each independently represents hydrogen, $C_{1-3}$alkyl or $C_{1-3}$alkoxy$C_{2-3}$alkyl) and $R^{29}$ is as defined hereinbefore);
7) $R^{29}$ (wherein $R^{29}$ is as defined hereinbefore);
8) $X^{14}C_{1-3}$alkyl$R^{28}$ (wherein $X^{14}$ represents —O—, —S—, —SO$_2$—, —NR$^{76}$CO—, —NR$^{77}$SO$_2$— or —NR$^{78}$— (wherein $R^{76}$, $R^{77}$ and $R^{78}$ each independently represents hydrogen, $C_{1-3}$alkyl or $C_{1-3}$alkoxy$C_{2-3}$ alkyl) and $R^{28}$ is as defined hereinbefore); and
9) $R^{54}C_{1-3}$alkyl$X^9R^{55}$ (wherein $R^{54}$, $R^{55}$ and $X^9$ are as defined hereinbefore);

may be prepared by reacting a compound of the formula IX:

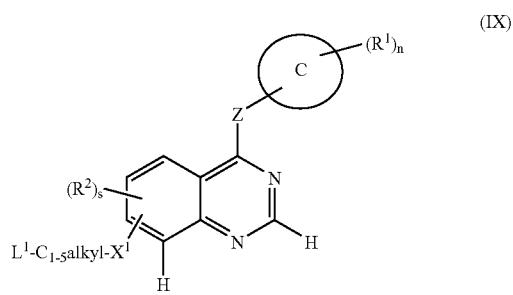

(IX)

(wherein $L^1$, $X^1$, $R^1$, $R^2$, ring C, Z, n and s are as hereinbefore defined) with a compound of the formula X:

$R^{62}$—H (X)

(wherein $R^{62}$ is as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Process (a) is preferred over processes (b), (c) and (d).

(e) The production of those compounds of the formula I and salts thereof wherein one or more of the substituents $(R^2)_m$ is represented by —NR$^{79}$R$^{80}$, where one (and the other is hydrogen) or both of $R^{79}$ and $R^{80}$ are $C_{1-3}$alkyl, may be effected by the reaction of compounds of formula I wherein the substituent $(R^2)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ is an amino group may be effected by the reduction of a corresponding compound of formula I wherein the substituent(s) at the corresponding position(s) of the quinazoline group is/are a nitro group(s). The reduction may conveniently be effected as described in process (i) hereinafter. The production of a compound of formula I and salts thereof wherein the substituent(s) at the corresponding position(s) of the quinazoline group is/are a nitro group(s) may be effected by the processes described hereinbefore and hereinafter in processes (a-d) and (i-v) using a compound selected from the compounds of the formulae (I-XXII) in which the substituent(s) at the corresponding position(s) of the quinazoline group is/are a nitro group(s).

(f) Compounds of the formula I and salts thereof wherein $X^1$ is —SO— or —SO$_2$— may be prepared by oxidation from the corresponding compound in which $X^1$ is —S— or —SO— (when $X^1$ is —SO$_2$— is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

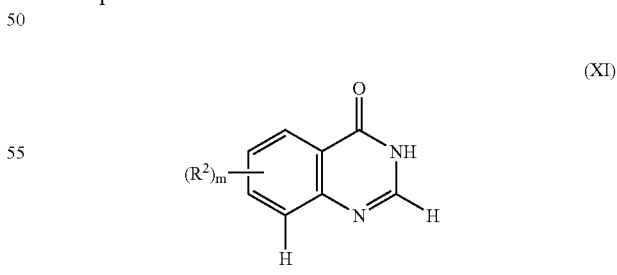

(XI)

wherein $R^2$ and m are as hereinbefore defined).

Convenient halogenating agents include inorganic acid halides, for example thionyl chloride, phosphorus(III)chloride, phosphorus(V)oxychloride and phosphorus(V)chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

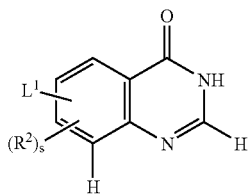

(XII)

(wherein $R^2$, s and $L^1$ are as hereinbefore defined) with a compound of the formula VIII as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XI and salts thereof wherein at least one $R^2$ is $R^5X^1$ and wherein $X^1$ is —O—, —S—, —SO—, —SO$_2$—, —CO—, —CONR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may for example also be prepared by the reaction of a compound of the formula XIII:

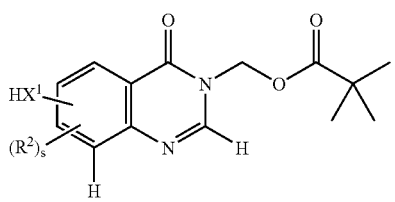

(XIII)

(wherein $R^2$ and s are as hereinbefore defined and $X^1$ is as hereinbefore defined in this section) with a compound of the formula VI as hereinbefore defined. The reaction may for example be effected as described for process (b) hereinbefore. The pivaloyloxymethyl group can then be cleaved by reacting the product with a base such as, for example, aqueous ammonia, triethylamine in water, an alkali metal or alkaline earth metal hydroxide or alkoxide, preferably aqueous ammonia, aqueous sodium hydroxide or aqueous potassium hydroxide, in a polar protic solvent such as an alcohol, for example methanol or ethanol. The reaction is conveniently effected at a temperature in the range 20 to 100° C., preferably in the range 20 to 50° C.

The compounds of formula XI and salts thereof may also be prepared by cyclising a compound of the formula XIV:

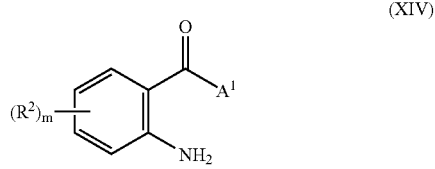

(XIV)

(wherein $R^2$ and m, are as hereinbefore defined, and $A^1$ is an hydroxy, alkoxy (preferably $C_{1-4}$alkoxy)or amino group) whereby to form a compound of formula XI or salt thereof. The cyclisation may be effected by reacting a compound of the formula XIV, where $A^1$ is an hydroxy or alkoxy group, with formamide or an equivalent thereof effective to cause cyclisation whereby a compound of formula XI or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XI may also be prepared by cyclising a compound of the formula XIV, where $A^1$ is an amino group, with formic acid or an equivalent thereof effective to cause cyclisation whereby a compound of formula XI or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof may for example be prepared by the reduction of the nitro group in a compound of the formula XV:

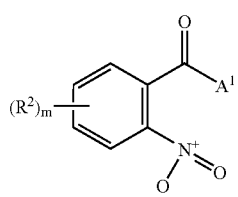

(XV)

(wherein $R^2$, m and $A^1$ are as hereinbefore defined) to yield a compound of formula XIV as hereinbefore defined. The reduction of the nitro group may conveniently be effected by any of the procedures known for such a transformation. The reduction may be carried out, for example, by stirring a solution of the nitro compound under hydrogen at 1 to 4 atmospheres pressure in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound under hydrogen at 2 atmospheres pressure in the presence of the activated metal and a solvent or diluent such as a mixture of water and alcohol, for example methanol or ethanol, at a temperature in the range, for example 50 to 150° C., conveniently at about 70° C.

Compounds of the formula XV and salts thereof may for example be prepared by the reaction of a compound of the formula XVI:

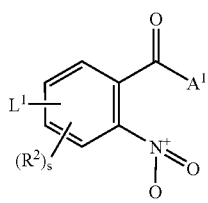

(XVI)

(wherein $R^2$, s, $L^1$ and $A^1$ are as hereinbefore defined) with a compound of the formula VIII as hereinbefore defined to give a compound of the formula XV. The reaction of the compounds of formulae XVI and VIII is conveniently effected under conditions as described for process (c) hereinbefore.

Compounds of formula XV and salts thereof wherein at least one $R^2$ is $R^5X^1$ and wherein $X^1$ is —O—, —S—, —SO$_2$—, —CO—, —CONR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may for example also be prepared by the reaction of a compound of the formula XVII:

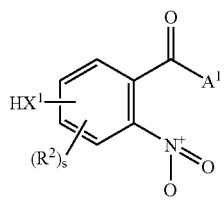

(XVII)

(wherein $R^2$, s and $A^1$ are as hereinbefore defined and $X^1$ is as hereinbefore defined in this section) with a compound of the formula VI as hereinbefore defined to yield a compound of formula XV as hereinbefore defined. The reaction of the compounds of formulae XVII and VI is conveniently effected under conditions as described for process (b) hereinbefore.

The compounds of formula III and salts thereof wherein at least one $R^2$ is $R^5X^1$ and wherein $X^1$ is —CH$_2$— may be prepared for example as described above from a compound of the formula XV (in which $R^2$ is —CH$_3$) or XIII (in which $HX^1$— is —CH$_3$), by radical bromination or chlorination to give a —CH$_2$Br or —CH$_2$Cl group which may then be reacted with a compound of the formula $R^5$—H under standard conditions for such substitution reactions.

The compounds of formula III and salts thereof wherein at least one $R^2$ is $R^5X^1$ and wherein $X^1$ is a direct bond may be prepared for example as described above from a compound of the formula XI, wherein the $R^5$ group is already present in the intermediate compounds (for example in a compound of the formula XV) used to prepare the compound of formula XI.

The compounds of formula III and salts thereof wherein at least one $R^2$ is $R^5X^1$ and wherein $X^1$ is —NR$^6$CO— or —NR$^9$SO$_2$— may be prepared for example from a compound of the formula XIII in which $HX^1$— is an —NHR$^6$— or —NHR$^9$— group (prepared for example from an amino group (later functionalised if necessary) by reduction of a nitro group) which is reacted with an acid chloride or sulfonyl chloride compound of the formula R$^5$COCl or R$^3$SO$_2$Cl.

The compounds of formula III and salts thereof wherein at least one $R^2$ is $R^5X^1$ and wherein $X^1$ is —O—, —S—, —SO$_2$—, —OCO—, —CONR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may also be prepared for example by reacting a compound of the formula XVIII:

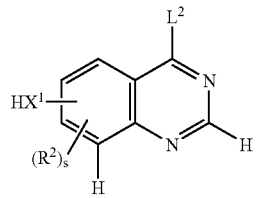

(XVIII)

(wherein $R^2$ and s are as hereinbefore defined, $X^1$ is as hereinbefore defined in this section and $L^2$ represents a displaceable protecting moiety) with a compound of the formula VI as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVIII and salts thereof may for example be prepared by deprotecting a compound of the formula XIX:

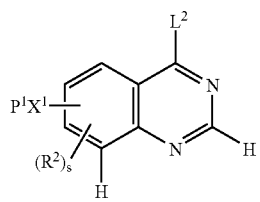

(XIX)

(wherein $R^2$, s and $L^2$ are as hereinbefore defined, $P^1$ is a protecting group and $X^1$ is as hereinbefore defined in the section describing compounds of the formula XVIII). The choice of protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where $P^1$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XI as hereinbefore defined, followed by introduction of halide to the compound of formula XI, thus obtained as hereinbefore defined, to yield a compound of formula III in which $L^1$ represents halogen.

(ii) Compounds of formula IV and salts thereof in which ring C is pyrazolyl may be prepared for exmaple by reacting hydrazine with either a compound of the formula $R^2$—C≡C—$CO_2$—$C_{1-4}$alkyl, (Al-Jallo et al, J. Het. Chem. 1976, 13, 455), or a compound of the formula $R^2$—C(O)—$CH_2$—C(O)—O—$C_{1-4}$alkyl. In both cases the reaction may be effected by heating the keto-ester compound in an inert diluent or solvent such as methanol, ethanol, isopropanol, isopentanol (preferably ethanol) in the presence of hydrazine hydrate. The reaction is effected at a temperature in a range 25-150° C. preferably 50-100° C.

(iii) Compounds of formula V as hereinbefore defined and salts thereof may be made by deprotecting the compound of formula XX:

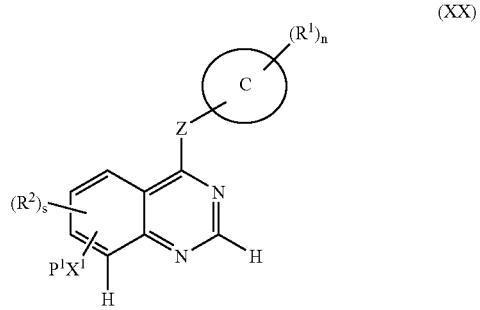

(XX)

(wherein ring C, Z, $R^1$, $R^2$, $P^1$, n and s are as hereinbefore defined and $X^1$ is as hereinbefore defined in the section describing compounds of the formula V) by a process for example as described in (i) above.

Compounds of the formula XX and salts thereof may be made by reacting compounds of the formulae XIX and IV as hereinbefore defined, under the conditions described in (a) hereinbefore, to give a compound of the formula XX or salt thereof.

(iv) Compounds of the formula VII and salts thereof may be made by reacting a compound of the formula XXI:

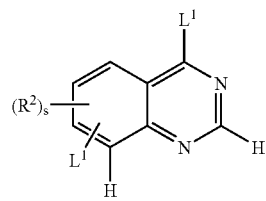

(XXI)

(wherein $R^2$, s and each $L^1$ are as hereinbefore defined and the $L^1$ in the 4-position and the other $L^1$ in a further position on the quinazoline ring may be the same or different) with a compound of the formula IV as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XXII:

$$L^1\text{—}C_{1-5}\text{alkyl-}L^1 \qquad (XXII)$$

(wherein $L^1$ is as hereinbefore defined) to give compounds of formula IX or salts thereof. The reaction may be effected for example by a process as described in (b) above.

(vi) Intermediate compounds wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein, for example, those of the formulae V, VII, IX and XX are novel and these are provided as a further feature of the invention. The preparation of these compounds is as described herein and/or is by methods well known to persons skilled in the art of organic chemistry.

The identification of compounds which potently inhibit the tyrosine kinase activity associated with VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al. (Oncogene, 1990, 5: 519-524), was isolated from cDNA and cloned into a baculovirus transplacement vector (for example pacYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21 (Sf21)) with viral DNA (eg Pharmingen BaculoGold) to prepare recombinant baculovirus (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al. 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis($\beta$aminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4-6 hours following oestrogen stimulation. This early increase in uterine weight has long been known to be due to oedema caused by increased permeability of the uterine vasculature and recently Cullinan-Bove and Koos (Endocrinology, 1993, 133:829-837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 µg/rat) in a solvent, or solvent only. The latter served as unstimulated controls. Test compounds were orally administered at various times prior to the administration of oestradiol benzoate.

Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5-5000 mg per square meter body area of the animal, i.e. approximately 0.1-100 mg/kg. A unit dose in the range, for example, 1-100 mg/kg, preferably 1-50 mg/kg is envisaged and this normally provides a therapeutically-effective dose. A unit dose form such as a tablet or capsule will usually contain, for example 1-250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin $\alpha v\beta 3$ function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testoterone $5\alpha$-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent of VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:
(i) evaporations were carried out by rotary evaporation in vacuo and work-up procedures were carried out after removal of residual solids such as drying agents by filtration;
(ii) operations were carried out at ambient temperature, that is in the range 18-25° C. and under an atmosphere of an inert gas such as argon;
(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;
(iv) yields are given for illustration only and are not necessarily the maximum attainable;
(v) melting points are uncorrected and were determined using a Mettler SP62 automatic melting point apparatus, an oil-bath apparatus or a Koffler hot plate apparatus.
(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(vii) intermediates were not generally fully characterised and purity was assessed by thin layer chromatography (TLC), high-performance liquid chromatography (HPLC), infra-red (IR) or NMR analysis;
(viii) petroleum ether refers to that fraction boiling between 40-60° C.
(ix) the following abbreviations have been used:
DMF N,N-dimethylformamide
DMSO dimethylsulphoxide
TFA trifluoroacetic acid
NMP 1-methyl-2-pyrrolidinone
THF tetrahydrofuran
HPLC RT retention time

EXAMPLE 1

3-Phenyl-4,5-dihydro-1H-pyrazol-5-one (160 mg, 1 mmol), (J. Org. Chem., 1967, 32, 3321-3324), was added in portions over 10 minutes to a suspension of sodium hydride (40 mg, 1 mmol, prewashed with THF) in DMF (3 ml) under nitrogen. After stirring for 20 minutes at ambient temperature 4-chloro-6,7-dimethoxyquinazoline (112 mg, 0.5 mmol) was added and the mixture was heated for 20 minutes at 60° C. After cooling, the mixture was diluted with saturated aqueous ammonium chloride solution and partitioned between ethyl acetate and water. The organic layer was washed with water, brine, dried (MgSO$_4$) and the volatiles removed by evaporation. The residue was purified by column chromatography eluting with methylene chloride/methanol (95/5 followed by 90/10). The volatiles were removed by evaporation, the residual solid was dissolved in methylene chloride and 3M ethereal hydrogen chloride (1 ml) was added. After removal of the solvent by evaporation, the residue was triturated with ether, collected by filtration and dried under vacuum to give 6,7-dimethoxy-4-(5-phenylpyrazol-3-yloxy)quinazoline (145 mg, 75%).

$^1$H NMR Spectrum: (DMSOd$_6$; CF$_3$COOD) 3.98 (s, 3H); 3.99 (s, 3H); 6.66 (s, 1H); 7.33 (t, 1H); 7.43 (t, 2H); 7.45 (s, 1H); 7.62 (s, 1H); 7.73 (d, 1H); 8.9 (s, 1H)

MS-ESI: 349 [MH]$^-$

The starting material was prepared as follows:

A mixture of 4,5-dimethoxyanthranilic acid (19.7 g) and formamide (10 ml) was stirred and heated at 190° C. for 5 hours. The mixture was allowed to cool to approximately 80° C. and water (50 ml) was added. The mixture was then allowed to stand at ambient temperature for 3 hours. The precipitate was collected by filtration, washed with water and dried to give 6,7-dimethoxy-3,4-dihydroquinazolin-4-one (3.65 g).

To a portion (2.06 g) of the material so obtained were added thionyl chloride (20 ml) and DMF (1 drop) and the mixture stirred and heated at reflux for 2 hours. Excess thionyl chloride was removed by evaporation and the residue was partitioned between ethyl acetate and a saturated aqueous sodium hydrogen carbonate solution. The organic phase was washed with water, dried (MgSO$_4$) and the solvent removed by evaporation. The residue was purified by column chromatography using increasingly polar mixtures of methylene chloride and ethyl acetate as eluent to give 4-chloro-6,7-dimethoxyquinazoline (0.6 g, 27%).

EXAMPLE 2

3-Benzyl-4,5-dihydro-1H-pyrazol-5-one (174 mg, 1 mmol), (J. Chem. Soc. Perk. Trans 1, 1980, 1618-1621), was added to a suspension of sodium hydride (40 mg, 1 mmol, prewashed with pentane) in DMF (3 ml) under nitrogen. After stirring for 30 minutes at ambient temperature, 4-chloro-6-methoxy-7-(3-morpholinopropoxy)quinazoline (135 mg, 0.4 mmol) was added and the mixture was heated at 80° C for 1 hour. After cooling, the mixture was diluted with saturated aqueous ammonium chloride solution and partitioned between ethyl acetate and water. The precipitate was collected by filtration, washed with water, followed by ethanol, ether and dried under vacuum to give 4-(5-benzylpyrazol-3-yloxy)-6-methoxy-7-(3-morpholinopropoxy) quinazoline (150 mg, 79%).

$^1$H NMR Spectrum: (DMSOd$_6$; CF$_3$COOD) 2.35-2.45 (m, 2H); 3.15-3.3 (m, 2H); 3.45 (t, 2H); 3.65 (d, 2H); 3.75 (t, 2H); 4.10 (s, 3H); 4.11 (s, 2H); 4.15 (d, 2H); 4.45 (d, 2H); 6.12 (s, 1H); 7.3-7.5 (m, 5H); 7.58 (s, 1H); 7.75 (s, 1H); 9.05 (s, 1H)

MS-ESI: 476 [MH]$^+$

The starting material was prepared as follows:

A mixture of 4-hydroxy-3-methoxybenzoic acid (4.5 g, 26.8 mmol), 3-morpholinopropyl chloride (9.5 g, 58.0 mmol), (prepared according to J. Am. Chem. Soc. 1945, 67, 736), potassium carbonate (8.0 g, 58 mmol), potassium iodide (1.0 g, 0.22 mmol) and DMF (80 ml) was stirred and heated at 100° C. for 3 hours. The solid was removed by filtration and the volatiles were removed by evaporation. The residue was dissolved in ethanol (50 ml), 2M sodium hydroxide (50 ml) was added and the mixture heated at 90° C. for 2 hours. After partial evaporation, the mixture was acidified with concentrated hydrochloric acid, washed with ether and then subjected to purification on a Diaion (trade mark of Mitsubishi) HP20SS resin column, eluting with water and then with a gradient of methanol (0 to 25%) in hydrochloric acid (pH2). Partial evaporation of the solvents and lyophilisation gave 3-methoxy-4-(3-morpholinopropoxy)benzoic acid (8.65 g, 97%).

$^1$H NMR Spectrum: (DMSOd$_6$; TFA) 2.17-2.24 (m, 2H); 3.10-3.16 (m, 2H); 3.30 (t, 2H); 3.52 (d, 2H); 3.71 (t, 2H); 3.82 (s, 3H); 4.01 (br d, 2H); 4.14 (t, 2H); 7.08 (d, 1H); 7.48 (d, 1H); 7.59 (dd, 1H)

MS-ESI: 296 [MH]$^+$

Fuming nitric acid (1.5 ml, 36.2 mmol) was added slowly at 0° C. to a solution of 3-methoxy-4-(3-morpholinopropoxy)benzoic acid (7.78 g, 23.5 mmol) in TFA (25 ml). The cooling bath was removed and the reaction mixture stirred at ambient temperature for 1 hour. The TFA was removed by evaporation and ice was added to the residue. The precipitate was collected by filtration, washed with a minimum of water followed by toluene and ether. The solid was dried under vacuum over phosphorus pentoxide to give 5-methoxy-4-(3-morpholinopropoxy)-2-nitrobenzoic acid (7.54 g) which was used without further purification.

$^1$H NMR Spectrum: (DMSOd$_6$; TFA) 2.16-2.23 (m, 2H); 3.10-3.17 (m, 2H); 3.30 (t, 2H); 3.52 (d, 2H); 3.66 (t, 2H); 3.93 (s, 3H); 4.02 (br d, 2H); 4.23 (t, 2H); 7.34 (s, 1H); 7.61 (s, 1H)

MS-EI: 340 [MH]$^+$

Thionyl chloride (15 ml) and DMF (0.05 ml) were added to 5-methoxy-4-(3-morpholinopropoxy)-2-nitrobenzoic acid (7.54 g). The mixture was heated at 50° C. for 1 hour, the excess thionyl chloride was removed by evaporation and by azeotroping with toluene (x2). The resulting solid was suspended in THF (200 ml) and ammonia was bubbled through the mixture for 30 minutes. The precipitate was removed by filtration and washed with THF. After concentration of the filtrate by evaporation, the product crystallised and was collected by filtration to give 5-methoxy-4-(3-morpholinopropoxy)-2-nitrobenzamide (5.25 g) as light yellow crystals which were used without further purification.

$^1$H NMR Spectrum: (DMSOd$_6$; TFA) 2.17-2.24 (m, 2H); 3.11-3.18 (m, 2H); 3.31 (t, 2H); 3.53 (d, 2H); 3.67 (t, 2H); 3.93 (s, 3H); 4.03 (br d, 2H); 4.21 (t, 2H); 7.17 (s, 1H); 7.62 (s, 1H)

MS-EI: 339 [MH]$^-$

Concentrated hydrochloric acid (30 ml) was added to a suspension of 5-methoxy-4-(3-morpholinopropoxy)-2-nitrobenzamide (5.67 g) in methanol (150 ml) and the mixture was heated to 60° C. When the 5-methoxy-4-(3-morpholinopropoxy)-2-nitrobenzamide had dissolved, iron powder (5.6 g, 100 mmol) was added in portions to the reaction mixture which was then heated for 90 minutes. After cooling, the insolubles were removed by filtration through diatomaceous earth, the volatiles were removed from the filtrate by evaporation and the residue was purified on a Diaion (trade mark of Mitsubishi) HP20SS resin column, eluting with water and then with hydrochloric acid (pH2). Concentration of the fractions by evaporation gave a precipitate which was collected by filtration and dried under vacuum over phosphorus pentoxide to give 2-amino-5-methoxy-4-(3-morpholinopropoxy)benzamide as a hydrochloride salt 4.67 g, 75%) as beige crystals.

$^1$H NMR Spectrum: (DMSOd$_6$; TFA) 2.22-2.28 (m, 2H); 3.12 (br t, 2H); 3.29 (t, 2H); 3.51 (d, 2H); 3.75 (t, 2H); 3.87 (s, 3H); 4.00 (br d, 2H); 4.12 (t, 2H); 7.06 (s, 1H); 7.53 (s, 1H)

MS-EI: 309 [MH]$^+$

A mixture of 2-amino-5-methoxy-4-(3-morpholinopropoxy)benzamide (4.57 g, 12.25 mmol) and Gold's reagent (2.6 g, 15.89 mmol) in dioxane (35 ml) was heated at reflux for 5 hours. Acetic acid (0.55 ml) and sodium acetate (1.0 g) were added to the reaction mixture which was heated for a further 3 hours. The mixture was cooled to ambient temperature and the volatiles removed by evaporation. The residue was adjusted to pH7 with 2M sodium hydroxide and then purified on a Diaion (trade mark of Mitsubishi) HP20SS resin column, eluting with methanol (gradient of 0 to 60%) in water. Concentration of the fractions by evaporation gave a precipitate which was collected by filtration and dried under vacuum over phosphorus pentoxide to give 4-hydroxy-6-methoxy-7-(3-morpholinopropoxy)quinazoline (3.04 g, 78%) as a white solid.

$^1$H NMR Spectrum: (CDCl$_3$) 2.10 (q, 2H); 2.48 (m, 4H); 2.56 (t, 2H); 3.72 (t, 4H); 4.00 (s, 3H); 4.24 (t, 2H); 7.18 (s, 1H); 7.60 (s, 1H); 8.00 (s, 1H); 10.86 (br s, 1H)

MS-EI: 319 [MH]$^+$

A mixture of 4-hydroxy-6-methoxy-7-(3-morpholinopropoxy)quinazoline (638 mg, 2 mmol) and thionyl chloride (8 ml) was heated at reflux for 30 minutes. Excess thionyl chloride was removed by evaporation and by azeotroping with toluene (x2). The residue was suspended in methylene chloride and 10% aqueous solution of sodium hydrogen carbonate was added to the mixture. The organic layer was separated, dried (MgSO$_4$) and the solvent removed by evaporation. The residue was triturated with ether, the solid was collected by filtration, washed with ether and dried under vacuum to give 4-chloro-6-methoxy-7-(3-morpholinopropoxy)quinazoline (590 mg, 87%).

$^1$H NMR Spectrum: (CDCl$_3$) 2.10-2.16 (m, 2H); 2.48 (br s, 4H); 2.57 (t, 2H); 3.73 (t, 4H); 4.05 (s, 3H); 4.29 (t, 2H); 7.36 (s, 1H); 7.39 (s, 1H); 8.86 (s, 1H)

MS-ESI: 337 [MH]$^-$

EXAMPLE 3

Using an analogous procedure to that described for Example 2, 4-chloro-6-methoxy-7-(3-morpholinopropoxy)quinazoline (169 mg, 0.5 mmol), (prepared as described for the starting material in Example 2), was reacted with 3-phenyl-4,5-dihydro-1H-pyrazol-5-one (200 mg, 1.25 mmol), (J. Org. Chem., 1967, 32, 3321-3324), in the presence of sodium hydride (50 mg, 1.25 mmol, prewashed with pentane) in DMF (3 ml) to give 6-methoxy-7-(3-morpholinopropoxy)-4-(5-phenylpyrazol-3-yloxy)quinazoline as the free base. The free base was dissolved in a mixture of methylene chloride/methanol (1/1) and 3M hydrochloric acid in methanol was added. The volatiles were removed by evaporation to give 6-methoxy-7-(3-morpholinopropoxy)-4-(5-phenylpyrazol-3-yloxy)quinazoline hydrochloride (115 mg, 43%).

$^1$H NMR Spectrum: (DMSOd$_6$; CF$_3$COOD) 2.3-2.4 (m, 2H); 3.15 (t, 2H); 3.3-3.4 (m, 2H); 3.55 (d, 2H); 3.75 (t, 2H); 4.01 (d, 2H); 4.05 (s, 3H); 4.38 (t, 2H); 6.7 (s, 1H); 7.4 (t, 1H); 7.5 (t, 2H); 7.55 (s, 1H); 7.7 (s, 1H); 7.8 (d, 2H); 8.91 (s, 1H)

MS-EI: 461 [M.]$^+$

| Elemental analysis: | Found | C 53.0 | H 5.8 | N 12.3 |
|---|---|---|---|---|
| C$_{25}$H$_{27}$N$_5$O$_4$ 0.7H$_2$O 2HCl | Requires | C 53.1 | H 5.7 | N 12.9% |

EXAMPLE 4

Using an analogous procedure to that described for Example 1, 4-chloro-6-methoxy-7-(2-methoxyethoxy)quinazoline (134 mg, 0.5 mmol) was reacted with 3-phenyl-4,5-dihydro-1H-pyrazol-5-one (160 mg, 1 mmol), (J. Org. Chem., 1967, 32, 3321-3324), in the presence of sodium hydride (40 mg, 1 mmol, prewashed with THF) in DMF (3 ml) to give 6-methoxy-7-(2-methoxyethoxy)-4-(5-phenylpyrazol-3-yloxy)quinazoline as the free base. The free base was dissolved in a mixture of methylene chloride/methanol (1/1) and 3M hydrochloric acid in methanol was added. The volatiles were removed by evaporation to give 6-methoxy-7-(2-methoxyethoxy)-4-(5-phenylpyrazol-3-yloxy)quinazoline hydrochloride (155 mg, 72%).

$^1$H NMR Spectrum: (DMSOd$_6$; CF$_3$COOD) 3.38 (s, 3H); 3.85 (t, 2H); 4.09 (s, 3H); 4.43 (t, 2H); 6.74 (s, 1H); 7.42 (t, 1H); 7.51 (t, 2H); 7.58 (s, 1H); 7.76 (s, 1H); 7.82 (d, 2H); 9.15 (s, 1H)

MS-EI: 392 [M.]$^-$

| Elemental analysis: | Found | C 56.0 | H 5.3 | N 12.3 |
|---|---|---|---|---|
| C$_{21}$H$_{20}$N$_4$O$_4$ 1.6H$_2$O 0.75HCl | Requires | C 56.2 | H 5.4 | N 12.5% |

The starting material was prepared as follows:

A mixture of ethyl 4-hydroxy-3-methoxybenzoate (9.8 g, 50 mmol), 2-bromoethyl methyl ether (8.46 ml, 90 mmol) and potassium carbonate (12.42 g, 90 mmol) in acetone (60 ml) was heated at reflux for 30 hours. The mixture was allowed to cool and the solids removed by filtration. The volatiles were removed from the filtrate by evaporation and the residue triturated with hexane to give ethyl 3-methoxy-4-(2-methoxyethoxy)benzoate (11.3 g, 89%) as a white solid.

m.p. 57-60° C.

$^1$H NMR Spectrum: (DMSOd$_6$) 1.31 (t, 3H); 3.29 (s, 3H); 3.32 (s, 3H); 3.68 (m, 2H); 4.16 (m, 2H); 4.28 (q, 2H); 7.06 (d, 1H); 7.45 (d, 1H); 7.56 (dd, 1H)

MS-FAB: 255 [MH]$^+$

Ethyl 3-methoxy-4-(2-methoxyethoxy)benzoate (9.5 g, 37 mmol) was added in portions to stirred concentrated nitric acid (75 ml) at 0° C. The mixture was allowed to warm to ambient temperature and stirred for a further 90 minutes. The mixture was diluted with water and extracted with methylene chloride, dried (MgSO$_4$) and the solvent removed by evaporation. The residue was triturated with hexane to give ethyl 5-methoxy-4-(2-methoxyethoxy)-2-nitrobenzoate (10.6 g, 95%) as an orange solid.

m.p. 68-69° C.

$^1$H NMR Spectrum: (DMSOd$_6$) 1.27 (t, 3H); 3.30 (s, 3H); 3.69 (m, 2H); 3.92 (s, 3H); 4.25 (m, 2H); 4.29 (q, 2H); 7.30 (s, 1H); 7.65 (s, 1H)

MS-Cl: 300 [MH]$^+$

A mixture of ethyl 5-methoxy-4-(2-methoxyethoxy)-2-nitrobenzoate (10.24 g, 34 mmol), cyclohexene (30 ml) and 10% palladium-on-charcoal catalyst (2.0 g) in methanol (150 ml) was heated at reflux for 5 hours. The reaction mixture was allowed to cool and diluted with methylene chloride. The catalyst was removed by filtration and the volatiles removed from the filtrate by evaporation. The residue was recrystallised from ethyl acetate/hexane to give ethyl 2-amino-5-methoxy-4-(2-methoxyethoxy)benzoate (8.0 g) as a buff solid. Formamide (80 ml) was added to this product and the mixture heated at 170° C. for 18 hours. About half the solvent was removed by evaporation under high vacuum and the residue was left to stand overnight. The solid product was collected by filtration, washed with ether and dried to give 6-methoxy-7-(2-methoxyethoxy)-3,4-dihydroquinazolin-4-one (5.3 g, 62% over two steps) as a grey solid.

$^1$H NMR Spectrum: (DMSOd$_6$) 3.35 (s, 3H); 3.74 (m, 2H); 3.89 (s, 3H); 4.26 (m, 2H); 7.15 (s, 1H); 7.47 (s, 1H); 7.98 (s, 1H); 12.03 (br s, 1H)

MS-Cl: 251 [MH]$^+$

DMF (0.5 ml) was added to a mixture of 6-methoxy-7-(2-methoxyethoxy)-3,4-dihydroquinazolin-4-one (5.1 g, 20 mmol) in thionyl chloride (50 ml). The mixture was stirred and heated at reflux for 3 hours, allowed to cool and the excess thionyl chloride removed by evaporation. The residue was suspended in methylene chloride and washed with aqueous sodium hydrogen carbonate solution. The aqueous phase was extracted with methylene chloride and the combined extracts dried (MgSO$_4$). The crude product was recrystallised from methylene chloride/hexane to give 4-chloro-6-methoxy-7-(2-methoxyethoxy)quinazoline (2.8 g, 51%) as a fine white solid.

$^1$H NMR Spectrum: (DMSOd$_6$) 3.37 (s, 3H); 3.77 (m, 2H); 4.01 (s, 3H); 4.37 (m, 2H); 7.40 (s, 1H); 7.49 (s, 1H); 8.88 (s, 1H)

MS-Cl: 269 [MH]$^+$

EXAMPLE 5

3-(4-Fluorophenyl)-4,5-dihydro-1H-pyrazol-5-one (222 mg, 1.25 mmol) was added in portions over 10 minutes to a suspension of sodium hydride (50 mg, 1.25 mmol, prewashed with hexane) in DMF (3 ml) under nitrogen. After stirring for 20 minutes at ambient temperature, 4-chloro-6-methoxy-7-(3-morpholinopropoxy)quinazoline (169 mg, 0.5 mmol), (prepared as described for the starting material in Example 2), was added and the mixture was heated at 60° C. for 1 hour. After cooling, the mixture was diluted with aqueous ammonium chloride solution and ether was added. The precipitate was collected by filtration, washed with water, and dried under vacuum. The solid was dissolved in methylene chloride/methanol (1/1) and 4M ethereal hydrogen chloride (0.5 ml) was added. After removal of the solvent by evaporation, the solid was triturated with ether, collected by filtration and dried under vacuum to give 4-(5-(4-fluorophenyl)pyrazol-3-yloxy)-6-methoxy-7-(3-morpholinopropoxy)quinazoline hydrochloride (115 mg, 48%).

¹H NMR Spectrum: (DMSOd₆; CF₃COOD) 2.3-2.4 (m, 2H); 3.1-3.2 (m, 2H); 3.35 (t, 2H); 3.55 (d, 2H); 3.75 (t, 2H); 4.02 (d, 2H); 4.04 (s, 3H); 4.35 (t, 2H); 6.71 (s, 1H); 7.35 (t, 2H); 7.53 (s, 1H); 7.67 (s, 1H); 7.83 (dd, 2H); 8.86 (s, 1H)

MS-ESI: 480 [MH]⁻

| Elemental analysis: | Found | C 52.7 | H 5.4 | N 12.5 |
| --- | --- | --- | --- | --- |
| C₂₅H₂₆N₅O₄F 1.2H₂O 1.9HCl | Requires | C 52.6 | H 5.3 | N 12.3% |

The starting material was prepared as follows:

To a solution of methyl 4-fluorobenzoyl acetate (588 mg, 3 mmol), (Clark, J. Chem. Soc. 1971, 1945) in ethanol (6 ml) was added hydrazine hydrate (150 mg, 3 mmol). After stirring for 30 minutes at ambient temperature, the mixture was stirred at 80° C. for 30 minutes. After cooling, ether was added. The precipitate was collected by filtration, washed with ether and dried under vacuum to give 3-(4-fluorophenyl)-4,5-dihydro-1H-pyrazol-5-one (504 mg, 94%).

¹H NMR Spectrum: (DMSOd₆; CF₃COOD) 6.2 (d, 0.25H, enolic proton partly exchanged); 7.35 (t, 2H); 7.8-7.9 (m, 2H)

MS-EI: 178 [M.]⁺

| Elemental analysis: | Found | C 60.8 | H 4.0 | N 15.9 |
| --- | --- | --- | --- | --- |
| C₉H₇N₂OF | Requires | C 60.8 | H 4.0 | N 15.7% |

EXAMPLE 6

3-Phenyl-4,5-dihydro-1H-pyrazol-5-one (270 mg, 1.68 mmol), (J. Org. Chem., 1967, 32, 3321-3324), was added in portions over 10 minutes to a suspension of sodium hydride (70 mg, 1.68 mmol, prewashed with pentane) in DMF (3 ml) under nitrogen. After stirring for 1 hour at ambient temperature 4-chloro-7-(2-methoxyethoxy)quinazoline (160 mg, 0.67 mmol) was added and the mixture was heated for 1 hour at 60° C. After cooling, the mixture was diluted with saturated aqueous ammonium chloride solution and partitioned between ethyl acetate and water. The organic layer was washed with water, brine, dried (MgSO₄) and the volatiles removed by evaporation. The residue was purified by column chromatography eluting with methanol/methylene chloride (5/95). The volatiles were removed by evaporation, the residual solid was dissolved in methylene chloride and 3M ethereal hydrogen chloride (0.5 ml) was added. After removal of the solvent by evaporation, the residue was triturated with ether, collected by filtration and dried under vacuum to give 7-(2-methoxyethoxy)-4-(5-phenylpyrazol-3-yloxy)quinazoline hydrochloride (120 mg, 46%).

¹H NMR Spectrum: (DMSOd₆; CF₃COOD) 3.36 (s, 3H); 3.8 (t, 2H); 4.4 (t, 2H); 6.7 (s, 1H); 7.4 (t, 1H); 7.4-7.55 (m, 4H); 7.8 (d, 2H); 8.35 (d, 1H); 8.94 (s, 1H)

MS-ESI: 363 [MH]⁺

| Elemental analysis: | Found | C 62.5 | H 4.9 | N 14.3 |
| --- | --- | --- | --- | --- |
| C₂₀H₁₈N₄O₃ 0.6HCl | Requires | C 62.2 | H 4.9 | N 14.5% |

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water 1/1 (250 ml). The precipitated solid was collected by filtration, washed with water and dried to give 7-fluoro-3,4-dihydroquinazolin-4-one (2.6 g, 82%).

Sodium (400 mg, 17 mmol) was added carefully to 2-methoxyethanol (10 ml) and the mixture heated at reflux for 30 minutes. 7-Fluoro-3,4-dihydroquinazolin-4-one (750 mg, 4.57 mmol) was added to the resulting solution and the mixture heated at reflux for 15 hours. The mixture was cooled and poured into water (250 ml). The mixture was acidified to pH4 with concentrated hydrochloric acid. The resulting solid product was collected by filtration, washed with water and then with ether, and dried under vacuum to give 7-(2-methoxyethoxy)-3,4-dihydroquinazolin-4-one (580 mg, 58%).

A solution of 7-(2-methoxyethoxy)-3,4-dihydroquinazolin-4-one (500 mg, 2.2 mmol) in thionyl chloride (15 ml) and DMF (0.1 ml) was heated at reflux for 3 hours. The volatiles were removed by evaporation to give 4-chloro-7-(2-methoxyethoxy)quinazoline hydrochloride as a cream solid (520 mg, 83%).

A suspension of 4-chloro-7-(2-methoxyethoxy)quinazoline hydrochloride (500 mg, 1.8 mmol) in a mixture of water (20 ml) and ethyl acetate (20 ml) was diluted with a saturated solution of sodium hydrogen carbonate. After stirring at ambient tempreature for 15 minutes the solution was extracted with ethyl acetate. The organic layer was washed with brine, dried (MgSO₄) and evaporated to give 4-chloro-7-(2-methoxyethoxy)quinazoline (345 mg, 80%).

EXAMPLE 7

Using an analogous procedure to that described for Example 6, 4-chloro-6-methoxy-7-(2-(imidazol-1-yl) ethoxy)quinazoline (0.2 g, 0.66 mmol) was reacted with 3-phenyl-4,5-dihydro-1H-pyrazol-5-one (260 mg, 1.6 mmol), (J. Org. Chem., 1967, 32, 3321-3324), in DMF (3 ml) containing sodium hydride (65 mg, 1.6 mmol) to give, after purification, 7-(2-(imidazol-1-yl)ethoxy)-6-methoxy-4-(5-phenylpyrazol-3-yloxy)quinazoline hydrochloride (100 mg, 28%).

¹H NMR Spectrum: (DMSOd₆; CF₃COOD) 4.05 (s, 3H); 4.70 (t, 2H); 4.79 (t, 2H); 6.7 (s, 1H); 7.4 (t, 1H); 7.5 (t, 2H); 7.57 (s, 1H); 7.7 (s, 1H); 7.73 (s, 1H); 7.8 (d, 1H); 7.85 (s, 1H); 8.91 (s, 1H); 9.22 (s, 1H)

MS-EI: 429 [MH]⁺

| Elemental analysis: | Found | C 50.6 | H 4.5 | N 15.3 |
| --- | --- | --- | --- | --- |
| C₂₃H₂₀N₆O₃ 1.5H₂O 2.5HCl | Requires | C 50.5 | H 4.7 | N 15.4% |

The starting material was prepared as follows:

A mixture of 2-amino-4-benzyloxy-5-methoxybenzamide (10 g, 0.04 mol), (prepared according to J. Med. Chem. 1977, vol 20, 146-149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol), in DMF (70 ml) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (100 ml) and poured onto ice/water (400 ml) and 2M hydrochloric acid (4 ml). The organic layer was separated and the aqueous layer extracted with ethyl acetate, the combined extracts were washed with brine, dried ($MgSO_4$) and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: ($DMSOd_6$) 1.11 (s, 9H); 3.89 (s, 3H); 5.3 (s, 2H); 5.9 (s, 2H); 7.27 (s, 1H); 7.35 (m, 1H); 7.47 (t, 2H); 7.49 (d, 2H); 7.51 (s, 1H); 8.34 (s, 1H)

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: ($DMSOd_6$) 1.1 (s, 9H); 3.89 (s, 3H); 5.89 (s, 2H); 7.0 (s, 1H); 7.48 (s, 1H); 8.5 (s, 1H)

Diethyl azodicarboxylate (435 mg, 2.5 mmol) was added dropwise to a suspension of 7-hydroxy-6-methoxy-3-((pivaloyloxy)methyl)-3,4-dihydroquinazolin-4-one (612 mg, 2 mmol), 2-(imidazol-1-yl)ethanol (280 mg, 2.5 mmol), (J. Med. Chem. 1993, 25, 4052-4060), and triphenylphosphine (655 mg, 2.5 mmol) in methylene chloride (10 ml) at 5° C. The mixture was stirred for 10 minutes at 5° C. and then 1 hour at ambient temperature. The mixture was poured directly on to a silica column and eluted with methylene chloride/methanol (95/5) to give 7-(2-(imidazol-1-yl)ethoxy)-6-methoxy-3-((pivaloyloxy)methyl)-3,4-dihydroquinazolin-4-one (640 mg, 80%).

$^1$H NMR Spectrum: ($CDCl_3$) 1.19 (s, 9H); 3.98 (s, 3H); 4.34 (m, 2H); 4.45 (m, 2H); 5.94 (s, 2H); 7.02 (s, 1H); 7.07 (s, 1H); 7.11 (s, 1H); 7.64 (s, 1H); 7.67 (s, 1H); 8.17 (s, 1H)

MS-ESI: 423 [MNa]$^+$

| Elemental analysis: | Found | C 58.3 | H 6.4 | N 13.9 |
|---|---|---|---|---|
| $C_{20}H_{24}N_4O_5$ 0.7$H_2O$ | Requires | C 58.2 | H 6.2 | N 13.6% |

A solution of 7-(2-(imidazol-1-yl)ethoxy)-6-methoxy-3-((pivaloyloxy)methyl)-3,4-dihydroquinazolin-4-one (640 mg, 1.6 mmol) in saturated methanolic ammonia (10 ml) was stirred for 15 hours at ambient temperature. The volatiles were removed by evaporation, the solid was triturated with ether, collected by filtration and dried under vacuum to give 7-(2-(imidazol-1-yl)ethoxy)-6-methoxy-3,4-dihydroquinazolin-4-one (412 mg, 90%).

$^1$H NMR Spectrum: ($DMSOd_6$) 3.89 (s, 3H); 4.4-4.5 (m, 4H); 6.9 (s, 1H); 7.16 (s, 1H); 7.28 (s, 1H); 7.47 (s, 1H); 7.7 (s, 1H); 7.99 (s, 1H)

MS-ESI: 287 [MH]$^+$

| Elemental Analysis: | Found | C 57.8 | H 5.2 | N 19.3 |
|---|---|---|---|---|
| $C_{14}H_{14}N_4O_3$ 0.3$H_2O$ | Requires | C 57.7 | H 5.1 | N 19.2% |

A mixture of 7-(2-(imidazol-1-yl)ethoxy)-6-methoxy-3,4-dihydroquinazolin-4-one (412 mg, 1.44 mmol), thionyl chloride (5 ml) and DMF (0.2 ml) was heated at reflux for 1 hour. The mixture was diluted with toluene and the volatiles were removed by evaporation. The residue was suspended in methylene chloride, cooled to 0° C. and aqueous sodium hydrogen carbonate solution was added. The resulting precipitate was collected by filtration and dried under vacuum to give 4-chloro-7-(2-(imidazol-1-yl)ethoxy)-6-methoxyquinazoline (258 mg, 59%).

$^1$H NMR Spectrum: ($DMSOd_6$) 4.01 (s, 3H); 4.47 (m, 2H); 4.53 (m, 2H); 6.89 (s, 1H); 7.27 (s, 1H); 7.41 (s, 1H); 7.49 (s, 1H); 7.70 (s, 1H); 8.88 (s, 1H)

MS-ESI: 327 [MNa]$^+$

EXAMPLE 8

Using an analogous procedure to that described for Example 6, 4-chloro-6-methoxy-7-(2-(2-methoxyethoxy)ethoxy)quinazoline (156 mg, 0.5 mmol) was reacted with 3-phenyl-4,5-dihydro-1H-pyrazol-5-one (200 mg, 1.25 mmol), (J. Org. Chem., 1967, 32, 3321-3324), in DMF (3 ml) containing sodium hydride (50 mg, 1.25 mmol) to give, after purification, 6-methoxy-7-(2-(2-methoxyethoxy)ethoxy)-4-(5-phenylpyrazol-3-yloxy)quinazoline hydrochloride (180 mg, 75%).

$^1$H NMR Spectrum: ($DMSOd_6$; $CF_3COOD$) 3.27 (s, 3H); 3.52 (t, 2H); 3.68 (t, 2H); 3.9 (t, 2H); 4.04 (s, 3H); 4.38 (t, 2H); 6.72 (s, 1H); 7.4 (t, 1H); 7.48 (t, 2H); 7.51 (s, 1H); 7.67 (s, 1H); 7.8 (d, 2H); 8.9 (s, 1H)

MS-ESI: 437 [MH]$^+$

| Elemental analysis: | Found | C 57.5 | H 5.8 | N 11.7 |
|---|---|---|---|---|
| $C_{23}H_{24}N_4O_5$ 0.5$H_2O$ 0.85HCl | Requires | C 58.0 | H 5.5 | N 11.8% |

The starting material was prepared as follows:

Diethyl azodicarboxylate (864 µl, 5.5 mmol) was added dropwise to a mixture of 7-hydroxy-6-methoxy-3-((pivaloyloxy)methyl)-3,4-dihydroquinazolin-4-one 1.2 g, 3.9 mmol) (prepared as described for the starting material in Example 7), triphenylphosphine (1.44 g, 5.5 mmol) and 2-(2-methoxyethoxy)ethanol (653 µl, 5.5 mmol) in methylene chloride (70 ml) cooled at 0° C. The mixture was stirred for 1.5 hours at ambient temperature and the solvent was removed by evaporation. The residue was purified by column chromatography eluting with a mixture of ethyl acetate/methylene chloride (50/50 followed by 80/20). The purified solid was suspended in ether, collected by filtration and dried under vacuum to give 6-methoxy-7-(2-(2-methoxyethoxy)ethoxy)-3-((pivaloyloxy)methyl)-3,4-dihydroquinazolin-4-one (1.70 g, 100%).

¹H NMR Spectrum: (DMSOd₆) 1.13 (s, 9H); 3.26 (s, 3H); 3.5 (m, 2H); 3.65 (m, 2H); 3.85 (m, 2H); 3.91 (s, 3H); 4.3 (m, 2H); 5.9 (s, 2H); 7.2 (s, 1H); 7.5 (s, 1H); 8.4 (s, 1H)

Saturated methanolic ammonia (20 ml) was added to a solution of 6-methoxy-7-(2-(2-methoxyethoxy)ethoxy)-3-((pivaloyloxy)methyl)-3,4-dihydroquinazolin-4-one (2.26 g, 5.5 mmol) in a mixture of ethanol (40 ml) and methylene chloride (15 ml). The mixture was stirred for 24 hours at ambient temperature, and further methanolic ammonia (20 ml) was added. The mixture was stirred for a further 24 hours at ambient temperature and the volatiles were removed by evaporation. The residue was triturated with ether, collected by filtration, dried under vacuum to give 6-methoxy-7-(2-(2-methoxyethoxy)ethoxy)-3,4-dihydroquinazolin-4-one (975 mg, 78%).

¹H NMR Spectrum: (DMSOd₆) 3.25 (s, 3H); 3.45 (t, 2H); 3.6 (t, 2H); 3.8 (t, 2H); 3.9 (s, 3H); 4.2 (t, 2H); 7.15 (s, 1H); 7.45 (s, 1H); 8.0 (s, 1H)

MS-EI: 294 [M]⁺

A solution of 6-methoxy-7-(2-(2-methoxyethoxy)ethoxy)-3,4-dihydroquinazolin-4-one (930 mg, 3.16 mmol) in thionyl chloride (15 ml) and DMF (150 µl) was heated at 60° C. for 1.5 hours. The mixture was allowed to cool and the volatiles were removed by evaporation and by azeotroping with toluene. The residue was dissolved in methylene chloride and 5% aqueous sodium hydrogen carbonate solution was added until the aqueous layer was at pH8. The organic layer was separated, washed with brine, dried (MgSO₄) and the solvent removed by evaporation. The residue was purified by flash chromatography eluting with ethyl acetate to give 4-chloro-6-methoxy-7-(2-(2-methoxyethoxy)ethoxy)quinazoline (863 mg, 87%).

¹H NMR Spectrum: (DMSOd₆) 3.24 (s, 3H); 3.47 (m, 2H); 3.62 (m, 2H); 3.84 (t, 2H); 4.01 (s, 3H); 4.25 (t, 2H); 7.41 (s, 1H); 7.49 (s, 1H); 8.88 (s, 1H)

EXAMPLE 9

Sodium hydride (40 mg, 1 mmol, prewashed with THF) was added to a suspension of 3-(3,4-dimethoxyphenyl)-4,5-dihydro-1H-pyrazol-5-one (220 mg, 1 mmol) in DMF (3 ml) under nitrogen. After stirring for 20 minutes at ambient temperature, 4-chloro-6-methoxy-7-(3-morpholinopropoxy)quinazoline (134 mg, 0.4 mmol), (prepared as described for the starting material in Example 2), was added and the mixture was heated for 30 minutes at 60° C. After cooling, the mixture was diluted with saturated aqueous ammonium chloride solution and partitioned between methylene chloride and water. The organic layer was washed with water, brine, dried (MgSO₄) and the volatiles were removed by evaporation. The residue was purified by column chromatography eluting with methylene chloride/ethyl acetate/methanol (1/10 followed by 5/4/1). The volatiles were removed by evaporation and the residual solid was collected by filtration, washed with ether and dried under vacuum to give 4-(5-(3,4-dimethoxyphenyl)pyrazol-3-yloxy)-6-methoxy-7-(3-morpholinopropoxy)quinazoline (120 mg, 57%).

¹H NMR Spectrum: (DMSOd₆) 1.95-2.05 (m, 2H); 2.4-2.6 (m, 6H); 3.6 (t, 4H); 3.81 (s, 3H); 3.85 (s, 3H); 4.02 (s, 3H); 4.3 (t, 2H); 6.65 (s, 1H); 7.05 (d, 1H); 7.35 (d, 1H); 7.42 (d, 2H); 7.55 (s, 1H); 8.65 (s, 1H)

MS-ESI: 522 [MH]⁺

| Elemental analysis: | Found | C 61.5 | H 6.1 | N 13.0 |
| C₂₇H₃₁N₅O₆ 0.2H₂O 0.12Et₂O | Requires | C 61.8 | H 6.1 | N 13.1% |

The starting material was prepared as follows:

To a solution of ethyl-3,4-dimethoxybenzoylacetate (1 g, 4 mmol), (Heterocycles 1979, 13, 239), in ethanol (5 ml) containing hydrazine hydrate (192 µl, 4 mmol) was stirred for 30 minutes at ambient temperature followed by 40 minutes being heated at reflux. After cooling at ambient temperature, the mixture was concentrated to half the volume and ether (10 ml) was added. After trituration, the solid was collected by filtration, washed with ether and dried under vacuum to give 3-(3,4-dimethoxyphenyl)-4,5-dihydro-1H-pyrazol-5-one (521 mg, 60%).

¹H NMR Spectrum: (DMSOd₆) 3.76 (s, 3H); 3.80 (s, 3H); 5.81 (s, 1H); 6.96 (d, 1H); 7.18 (dd, 1H); 7.25 (d, 1H)

MS-ESI: 221 [MH]⁺

EXAMPLE 10

Using an analogous procedure to that described for Example 9, 4-chloro-6-methoxy-7-(2-methoxyethoxy)quinazoline (134 mg, 0.5 mmol), (prepared as described for the starting material in Example 4), was reacted with 3-(4-methoxyphenyl)-4,5-dihydro-1H-pyrazol-5-one (190 mg, 1 mmol) in the presence of sodium hydride (40 mg, 1 mmol, prewashed with THF) in DMF (3 ml) to give 6-methoxy-7-(2-methoxyethoxy)-4-(5-(4-methoxyphenyl)pyrazol-3-yloxy)quinazoline (125 mg, 59%).

¹H NMR Spectrum: (DMSOd₆) 3.36 (s, 3H); 3.8 (t, 2H); 3.82 (s, 3H); 4.01 (s, 3H); 4.35 (t, 2H); 6.6 (s, 1H); 7.05 (d, 2H); 7.45 (s, 1H); 7.55 (s, 1H); 7.75 (d, 2H); 8.65 (s, 1H)

MS-ESI: 423 [MH]⁺

| Elemental analysis: | Found | C 61.0 | H 5.2 | N 13.0 |
| C₂₂H₂₂N₄O₅ 0.5H₂O | Requires | C 61.2 | H 5.4 | N 13.0% |

The starting material was prepared using an analogous procedure to that described for the synthesis of 3-(3,4-dimethoxyphenyl)-4,5-dihydro-1H-pyrazol-5-one in Example 9. Ethyl-4-methoxybenzoylacetate (1 g, 4.5 mmol) was reacted with hydrazine hydrate (218 µl, 4.5 mmol) to give 3-(4-methoxyphenyl)-4,5-dihydro-1H-pyrazol-5-one (570 mg, 67%).

¹H NMR Spectrum: (DMSOd₆) 3.77 (s, 3H); 5.77 (s, 1H); 6.96 (d, 2H); 7.60 (d, 2H);

MS-ESI: 191 [MH]⁺

EXAMPLE 11

Using an analogous procedure to that described for Example 9, 4-chloro-6-methoxy-7-(3-morpholinopropoxy)quinazoline (134 mg, 0.4 mmol), (prepared as described for the starting material in Example 2), was reacted with 3-(3-pyridyl)-4,5-dihydro-1H-pyrazol-5-one (161 mg, 1 mmol) in the presence of sodium hydride (40 mg, 1 mmol, prewashed with THF) in DMF (3 ml) to give 6-methoxy-7-(3-morpholinopropoxy)-4-(5-(3-pyridyl)pyrazol-3-yloxy)quinazoline (110 mg, 59%).

¹H NMR Spectrum: (DMSOd₆) 1.95-2.05 (m, 2H); 2.4 (br s, 4H); 2.5 (t, 2H); 3.6 (t, 4H); 4.02 (s, 3H); 4.28 (t, 2H); 6.85 (s, 1H); 7.45 (s, 1H); 7.55 (m, 1H); 7.6 (s, 1H); 8.3 (d, 1H); 8.6 (d, 1H); 8.65 (s, 1H); 9.05 (s, 1H)

MS-ESI: 463 [MH]⁺

| Elemental analysis: | Found | C 62.2 | H 5.7 | N 18.0 |
|---|---|---|---|---|
| $C_{24}H_{26}N_6O_4$ | Requires | C 62.3 | H 5.7 | N 18.2% |

The starting material was prepared using an analogous procedure to that described in Example 9. Ethyl-2-(3-pyridylcarbonyl)acetate (1 g, 5.18 mmol) was treated with hydrazine hydrate (251 µl, 5.2 mmol) to give 3-(3-pyridyl)-4,5-dihydro-1H-pyrazol-5-one (413 mg, 50%).

¹H NMR Spectrum: (DMSOd₆) 6.0 (br s, 1H); 7.4 (m, 1H); 8.05 (m, 1H); 8.5 (d, 1H); 8.92 (s, 1H); 9.7-10 (br s, 1H)

MS (ESI): 162 [MH]⁺

EXAMPLE 12

Using an analogous procedure to that described for Example 9, 4-chloro-6-methoxy-7-(3-morpholinopropoxy)quinazoline (140 mg, 0.415 mmol), (prepared as described for the starting material in Example 2), was reacted with 3-(4-chlorophenyl)-4,5-dihydro-1H-pyrazol-5-one (202 mg, 1.04 mmol) in the presence of sodium hydride (41.5 mg, 1.04 mmol, prewashed with THF) in DMF (2.5 ml) to give 4-(5-(4-chlorophenyl)pyrazol-3-yloxy)-6-methoxy-7-(3-morpholinopropoxy)quinazoline (150 mg, 73%).

¹H NMR Spectrum: (DMSOd₆) 1.95-2.05 (m, 2H); 2.4 (br s, 4H); 2.5 (t, 2H); 3.6 (t, 4H); 4.0 (s, 3H); 4.25 (t, 2H); 6.76 (s, 1H); 7.42 (s, 1H); 7.55 (s, 1H); 7.6 (d, 2H); 7.85 (d, 2H); 8.65 (s, 1H)

MS (ESI): 496 [MH]⁺

The starting material was prepared using an analogous procedure to that described in Example 9. Ethyl-4-chlorobenzoyl acetate (734 mg, 3.24 mmol) was treated with hydrazine hydrate (157 µl, 3.24 mmol) to give 3-(4-chlorophenyl)-4,5-dihydro-1H-pyrazol-5-one (244 mg, 39%).

¹H NMR Spectrum: (DMSOd₆) 5.9 (br s, 1H); 7.45 (d, 2H); 7.7 (d, 2H); 9.7-10 (br s, 1H)

MS (ESI): 195 [MH]⁺

EXAMPLE 13

Using an analogous procedure to that described for Example 9, 4-chloro-6-methoxy-7-(3-morpholinopropoxy)quinazoline (200 mg, 0.59 mmol), (prepared as described for the starting material in Example 2), was reacted with 3-(4-pyridyl)-4,5-dihydro-1H-pyrazol-5-one (240 mg, 1.5 mmol) in the presence of sodium hydride (59 mg, 1.5 mmol, prewashed with THF) in DMF (3 ml) to give 6-methoxy-7-(3-morpholinopropoxy)-4-(5-(4-pyridyl)pyrazol-3-yloxy)quinazoline (130 mg, 48%).

¹H NMR Spectrum: (DMSOd₆) 1.95-2.05 (m, 2H); 2.4 (br s, 4H); 2.45 (t, 2H); 3.6 (t, 4H); 4.0 (s, 3H); 4.25 (t, 2H); 6.95 (s, 1H); 7.4 (s, 1H); 7.55 (s, 1H); 7.8 (d, 2H); 8.62 (s, 1H); 8.68 (d, 2H)

MS (ESI): 463 [MH]⁺

| Elemental analysis: | Found | C 61.2 | H 5.9 | N 17.8 |
|---|---|---|---|---|
| $C_{24}H_{26}N_6O_4$ 0.5$H_2O$ | Requires | C 61.1 | H 5.8 | N 17.8% |

The starting material was prepared using an analogous procedure to that described in Example 9. Ethyl isonicotinoyl acetate (1 g, 5.2 mmol) was treated with hydrazine hydrate (251 µl, 5.2 mmol) in ethanol (5 ml) to give 3-(4-pyridyl)-4,5-dihydro-1H-pyrazol-5-one (714 mg, 86%).

¹H NMR Spectrum: (DMSOd₆) 5.9-6.2 (br s, 1H); 7.63 (d, 2H); 8.6 (br s, 2H)

MS (ESI): 162 [MH]⁺

EXAMPLE 14

3-Phenyl-4,5-dihydro-1H-pyrazol-5-one (182 mg, 1.14 mmol), (J. Org. Chem., 1967, 32, 3321-3324), was added in portions to a suspension of sodium hydride (46 mg, 1.14 mmol, prewashed with pentane) in DMF (3 ml). After stirring for 30 minutes at ambient temperature, 4-chloro-6-methoxy-7-(3-(4-methylpiperazin-1-yl)propoxy)quinazoline (200 mg, 0.57 mmol) was added. The mixture was stirred for 30 minutes at 60° C. After cooling, the mixture was diluted with saturated aqueous ammonium chloride solution and partitioned between ethyl acetate and water. The organic layer was passed through an ISOLUTE (trade mark of IST) SPE column. The column was thoroughly washed with methanol. The product was recovered from the column by washing with a mixture of 0.1M solution of ammonia in methylene chloride/methanol (1/1). The volatiles were removed by evaporation and the solid was collected by filtration, washed with ether and dried under vacuum to give 6-methoxy-7-(3-(4-methylpiperazin-1-yl)propoxy)-4-(5-phenylpyrazol-3-yloxy)quinazoline (206 mg, 76%).

¹H NMR Spectrum: (DMSOd₆; CF₃COOD) 2.3-2.4 (m, 2H); 2.98 (s, 3H); 3.3-3.6 (m, 5H); 3.6-4.0 (m, 5H); 4.04 (s, 3H); 4.38 (t, 2H); 6.75 (s, 1H); 7.42 (s, 1H); 7.5 (t, 2H); 7.55 (s, 1H); 7.7 (s, 1H); 7.85 (d, 2H); 8.9 (s, 1H)

MS (ESI): 475 [MH]⁺

The starting material was prepared as follows:

1-Bromo-3-chloropropane (0.97 ml, 9.8 mmol) was added to a solution of 7-hydroxy-6-methoxy-3-((pivaloyloxy)methyl)-3,4-dihydroquinazolin-4-one (2.5 g, 8.17 mmol), (prepared as described for the starting material in Example 7), in DMF (40 ml) containing potassium carbonate (2.8 g, 20 mmol). The mixture was stirred overnight at ambient temperature and partitioned between ethyl acetate and water. The organic layer was washed with water, brine, dried (MgSO₄) and evaporated to give 7-(3-chloropropoxy)-6-methoxy-3-((pivaloyloxy)methyl)-3,4-dihydroquinazolin-4-one (3.10 g, 100%).

¹H NMR Spectrum: (DMSOd₆) 1.12 (s, 9H); 2.15 (t, 2H); 3.8 (t, 2H); 3.9 (s, 3H); 4.25 (t, 2H); 5.9 (s, 2H); 7.2 (s, 1H); 7.5 (s, 1H); 8.36 (s, 1H)

MS (ESI): 383 [MH]⁺

A solution of 7-(3-chloropropoxy)-6-methoxy-3-((pivaloyloxy)methyl)-3,4-dihydroquinazolin-4-one (3 g, 7.84 mmol) in 1-methylpiperazine (30 ml) was heated at 100° C. for 1 hour. After cooling, the mixture was partitioned between saturated ammonium chloride and methylene chloride. The organic layer was washed with water, brine, dried (MgSO$_4$) and the volatiles were removed by evaporation. The residue was purified by column chromatography eluting with methylene chloride/methanol (95/5 followed by 90/10). The volatiles were removed by evaporation to give 6-methoxy-7-(3-(4-methylpiperazin-1-yl)propoxy)-3-((pivaloyloxy)methyl)-3,4-dihydroquinazolin-4-one (3.24 g, 92%).

A solution of 6-methoxy-7-(3-(4-methylpiperazin-1-yl)propoxy)-3-((pivaloyloxy)methyl)-3,4-dihydroquinazolin-4-one (3.1 g, 7 mmol) in 5M ammonia in methanol (60 ml) was stirred at ambient temperature overnight. The volatiles were removed by evaporation and the residue was triturated with ether, collected by filtration, washed with ether and dried under vacuum to give 6-methoxy-7-(3-(4-methylpiperazin-1-yl)propoxy)-3,4-dihydroquinazolin-4-one (2.1 g, 91%).

$^1$H NMR Spectrum: (DMSOd$_6$) 1.9-2.0 (m, 2H); 2.2 (s, 3H); 2.2-2.5 (m, 10H); 3.85 (s, 3H); 4.15 (t, 2H); 7.1 (s, 1H); 7.45 (s, 1H); 7.95 (s, 1H)

MS (ESI): 331 [MH]$^+$

A solution of 6-methoxy-7-(3-(4-methylpiperazin-1-yl)propoxy)-3,4-dihydroquinazolin-4-one (2.05 g, 6.2 mmol) in thionyl chloride (30 ml) containing DMF (500 μl) was heated at reflux for 30 minutes. After cooling, the volatiles were removed by evaporation. The residue was partitioned between methylene chloride and saturated aqueous sodium hydrogen carbonate and the aqueous layer was adjusted to pH8 with solid sodium hydrogen carbonate. The organic layer was washed with water, brine, dried (MgSO$_4$) and the volatiles were removed by evaporation. The residue was triturated with ether, collected by filtration, washed with ether and dried under vacuum to give 4-chloro-6-methoxy-7-(3-(4-methylpiperazin-1-yl)propoxy)quinazoline (1.4 g, 65).

$^1$H NMR Spectrum: (DMSOd$_6$) 2.1 (m, 2H); 2.2 (s, 3H); 2.3-2.5 (m, 10H); 4.05 (s, 3H); 4.3 (t, 2H); 7.4 (s, 1H); 7.45 (s, 1H); 8.88 (s, 1H)

EXAMPLE 15

A solution of 3-amino-5-(4-methoxyphenyl)-4H-pyrazole (74 mg, 0.39 mmol), (Synthesis, 1984, 3, 276), in isopropanol (3.5 ml) was added to 4-chloro-6-methoxy-7-((1-methylpiperidin-4-yl)methoxy)quinazoline (110 mg, 0.34 mmol) followed by 5M hydrogen chloride in isopropanol (78 μl, 0.39 mmol) and the mixture was heated at reflux for 1.5 hours. After cooling to 5° C., the precipitate was collected by filtration washed with isopropanol, followed by ether and dried under vacuum at 60° C. to give 4-(5-(4-methoxyphenyl)pyrazol-3-ylamino)-6-methoxy-7-((1-methylpiperidin-4-yl)methoxy)quinazoline hydrochloride (133 mg, 72%).

$^1$H NMR Spectrum: (DMSOd$_6$, CH$_3$COOD) 1.6-1.75 (m, 2H); 2.05 (d, 2H); 2.1-2.2 (m, 1H); 2.75 (s, 3H); 3.05 (t, 2H); 3.5 (d, 2H); 3.8 (s, 3H); 4.02 (s, 3H); 4.1 (d, 2H); 7.06 (d, 2H); 7.08 (s, 1H); 7.2 (s, 1H); 7.37 (d, 2H); 8.15 (s, 1H); 8.92 (s, 1H)

MS (ESI): 475 [MH]$^+$

HPLC RT=2.5 minutes

The starting material was prepared as follows:

A solution of di-tert-butyl dicarbonate (41.7 g, 0.19 mol) in ethyl acetate (75 ml) was added in portions to a solution of ethyl 4-piperidinecarboxylate (30 g, 0.19 mol) in ethyl acetate (150 ml) cooled at 5° C., while maintaining the temperature in the range of 0-5° C. After stirring for 48 hours at ambient temperature, the mixture was poured onto water (300 ml). The organic layer was separated, washed successively with water (200 ml), 0.1M aqueous hydrochloric acid (200 ml), saturated sodium hydrogen carbonate (200 ml) and brine (200 ml), dried (MgSO$_4$), and the volatiles were removed by evaporation to give ethyl 4-(1-tert-butyloxycarbonylpiperidine)carboxylate (48 g, 98%).

$^1$H NMR Spectrum: (CDCl$_3$) 1.25 (t, 3H); 1.45 (s, 9H); 1.55-1.70 (m, 2H); 1.8-2.0 (d, 2H); 2.35-2.5 (m, 1H); 2.7-2.95 (t, 2H); 3.9-4.1 (br s, 2H); 4.15 (q, 2H)

A solution of 1M lithium aluminium hydride in THF (133 ml, 0.133 mol) was added in portions to a solution of ethyl 4-(1-tert-butyloxycarbonylpiperidine)carboxylate (48 g, 0.19 mol) in dry THF (180 ml) cooled at 0° C. After stirring at 0° C. for 2 hours, water (30 ml) was added followed by 2M sodium hydroxide (10 ml). The precipitate was filtered through diatomaceous earth and washed with ethyl acetate. The filtrate was washed with water, brine, dried (MgSO$_4$) and the volatiles were removed by evaporation to give 4-hydroxymethyl-1-tert-butyloxycarbonylpiperidine (36.3 g, 89%).

$^1$H NMR Spectrum: (CDCl$_3$) 1.05-1.2 (m, 2H), 1.35-1.55 (m, 10H); 1.6-1.8 (m, 2H); 2.6-2.8 (t, 2H); 3.4-3.6 (t, 2H); 4.0-4.2 (br s, 2H)

MS (EI): 215 [M.]$^+$ 1,4-Diazabicyclo[2.2.2]octane (42.4 g, 0.378 mol) was added to a solution of 4-hydroxymethyl-1-tert-butyloxycarbonylpiperidine (52.5 g, 0.244 mol) in tert-butyl methyl ether (525 ml). After stirring for 15 minutes at ambient temperature, the mixture was cooled to 5° C. and a solution of toluene sulphonyl chloride (62.8 g, 0.33 mmol) in tert-butyl methyl ether (525 ml) was added in portions over 2 hours while maintaining the temperature at 0° C. After stirring for 1 hour at ambient temperature, petroleum ether (II) was added. The precipitate was removed by filtration. The volatiles were removed by evaporation to give a solid. The solid was dissolved in ether and washed successively with 0.5M aqueous hydrochloric acid (2×500 ml), water, saturated sodium hydrogen carbonate and brine, dried (MgSO$_4$) and the volatiles were removed by evaporation to give 4-(4-methylphenylsulphonyloxymethyl)-1-tert-butyloxycarbonylpiperidine (76.7 g, 85%).

$^1$H NMR Spectrum: (CDCl$_3$) 1.0-1.2 (m, 2H), 1.45 (s, 9H); 1.65 (d, 2H); 1.75-1.9 (m, 2H); 2.45 (s, 3H); 2.55-2.75 (m, 2H); 3.85 (d, 1H); 4.0-4.2 (br s, 2H); 7.35 (d, 2H); 7.8 (d, 2H)

MS (ESI): 392 [MNa]$^+$ 4-(4-Methylphenylsulphonyloxymethyl)-1-tert-butyloxycarbonylpiperidine (40 g, 0.11 mol) was added to a suspension of ethyl 3-methoxy-4-hydroxybenzoate (19.6 g, 0.1 mol) and potassium carbonate (28 g, 0.2 mol) in dry DMF (200 ml). After stirring at 95° C. for 2.5 hours, the mixture was cooled to ambient temperature and partitioned between water and ethyl acetate/ether. The organic layer was washed with water, brine, dried (MgSO$_4$) and the volatiles were removed by evaporation. The resulting oil was crystallised from petroleum ether and the suspension was stored overnight (at 5° C.). The solid was collected by filtration, washed with petroleum ether and dried under vacuum to give ethyl 3-methoxy-4-(1-tert-butyloxycarbonylpiperidin-4-ylmethoxy)benzoate (35 g, 89%).

m.p. 81-83° C.

$^1$H NMR Spectrum: (CDCl$_3$) 1.2-1.35 (m, 2H); 1.4 (t, 3H); 1.48 (s, 9H); 1.8-1.9 (d, 2H); 2.0-2.15 (m, 2H); 2.75 (t, 2H);

3.9 (d, 2H); 3.95 (s, 3H); 4.05-4.25 (br s, 2H); 4.35 (q, 2H); 6.85 (d, 1H); 7.55 (s, 1H); 7.65 (d, 1H)

MS (ESI): 416 [MNa]+

| Elemental analysis: | Found | C 63.4 | H 8.0 | N 3.5 |
| --- | --- | --- | --- | --- |
| $C_{21}H_{31}NO_6 \cdot 0.3H_2O$ | Requires | C 63.2 | H 8.0 | N 3.5% |

Formaldehyde (12M, 37% in water, 35 ml, 420 mmol) was added to a solution of ethyl 3-methoxy-4-(1-tert-butyloxycarbonylpiperidin-4-ylmethoxy)benzoate (35 g, 89 mmol) in formic acid (35 ml). After stirring at 95° C. for 3 hours, the volatiles were removed by evaporation. The residue was dissolved in methylene chloride and 3M hydrogen chloride in ether (40 ml, 120 mmol) was added. After dilution with ether, the mixture was triturated until a solid was formed. The solid was collected by filtration, washed with ether and dried under vacuum overnight at 50° C. to give ethyl 3-methoxy-4-(1-methylpiperidin-4-ylmethoxy) benzoate (30.6 g, quant.).

$^1$H NMR Spectrum: (DMSOd$_6$) 1.29 (t, 3H); 1.5-1.7 (m, 2H); 1.95 (d, 2H); 2.0-2.15 (br s, 1H); 2.72 (s, 3H); 2.9-3.1 (m, 2H); 3.35-3.5 (br s, 2H); 3.85 (s, 3H); 3.9-4.05 (br s, 2H); 4.3 (q, 2H); 7.1 (d, 1H); 7.48 (s, 1H); 7.6 (d, 1H)

MS (ESI): 308 [MH]

A solution of ethyl 3-methoxy-4-(1-methylpiperidin-4-ylmethoxy)benzoate (30.6 g, 89 mmol) in methylene chloride (75 ml) was cooled to 0-5° C. TFA (37.5 ml) was added followed by the addition in portions over 15 minutes of a solution of fuming 24M nitric acid (7.42 ml, 178 mmol) in methylene chloride (15 ml). After completion of the addition, the solution was allowed to warm up and stirred at ambient temperature for 2 hours. The volatiles were removed under vacuum and the residue was dissolved in methylene chloride (50 ml). The solution was cooled to 0-5° C. and ether was added. The precipitate was collected by filtration, and dried under vacuum at 50° C. The solid was dissolved in methylene chloride (500 ml) and 3M hydrogen chloride in ether (30 ml) was added followed by ether (500 ml). The solid was collected by filtration and dried under vacuum at 50° C. to give ethyl 3-methoxy-4-(1-methylpiperidin-4-ylmethoxy)-6-nitrobenzoate (28.4 g, 82%).

$^1$H NMR Spectrum: (DMSOd$_6$) 1.3 (t, 3H), 1.45-1.65 (m, 2H); 1.75-2.1 (m, 3H); 2.75 (s, 3H); 2.9-3.05 (m, 2H); 3.4-3.5 (d, 2H); 3.95 (s, 3H); 4.05 (d, 2H); 4.3 (q, 2H); 7.32 (s, 1H); 7.66 (s, 1H)

MS (ESI): 353 [MH]+

A suspension of ethyl 3-methoxy-4-(1-methylpiperidin-4-ylmethoxy)-6-nitrobenzoate (3.89 g, 10 mmol) in methanol (80 ml) containing 10% platinum on activated carbon (50% wet) (389 mg) was hydrogenated at 1.8 atmospheres pressure until uptake of hydrogen ceased. The mixture was filtered and the volatiles were removed by evaporation. The residue was dissolved in water (30 ml) and adjusted to pH10 with a saturated solution of sodium hydrogen carbonate. The mixture was diluted with ethyl acetate/ether (1/1) and the organic layer was separated. The aqueous layer was further extracted with ethyl acetate/ether and the organic layers were combined. The organic layers were washed with water, brine, dried (MgSO$_4$), filtered and the volatiles were removed by evaporation. The resulting solid was triturated in a mixture of ether/petroleum ether, filtered, washed with petroleum ether and dried under vacuum at 60° C. to give ethyl 6-amino-3-methoxy-4-(1-methylpiperidin-4-ylmethoxy)benzoate (2.58 g, 80%).

m.p. 111-112° C.

$^1$H NMR Spectrum: (CDCl$_3$) 1.35 (t, 3H), 1.4-1.5 (m, 2H); 1.85 (m, 3H); 1.95 (t, 2H); 2.29 (s, 3H); 2.9 (d, 2H); 3.8 (s, 3H); 3.85 (d, 2H); 4.3 (q, 2H); 5.55 (br s, 2H); 6.13 (s, 1H); 7.33 (s, 1H)

MS (ESI): 323 [MH]+

| Elemental analysis: | Found | C 62.8 | H 8.5 | N 8.3 |
| --- | --- | --- | --- | --- |
| $C_{17}H_{26}N_2O_4 \cdot 0.2H_2O$ | Requires | C 62.6 | H 8.2 | N 8.6% |

A solution of ethyl 6-amino-3-methoxy-4-(1-methylpiperidin-4-ylmethoxy)benzoate (16.1 g, 50 mmol) in 2-methoxyethanol (160 ml) containing formamidine acetate (5.2 g, 50 mmol) was heated at 115° C. for 2 hours. Formamidine acetate (10.4 g, 100 mmol) was added in portions every 30 minutes during 4 hours. Heating was prolonged for 30 minutes after the last addition. After cooling, the volatiles were removed under vacuum. The solid was dissolved in ethanol (100 ml) and methylene chloride (50 ml). The precipitate was removed by filtration and the filtrate was concentrated to a final volume of 100 ml. The suspension was cooled to 5° C. and the solid was collected by filtration, washed with cold ethanol followed by ether and dried under vacuum overnight at 60° C. to give 6-methoxy-7-((1-methylpiperidin-4-yl)methoxy)-3,4-dihydroquinazolin-4-one (12.7 g, 70%).

$^1$H NMR Spectrum: (DMSOd$_6$) 1.25-1.4 (m, 2H); 1.75 (d, 2H); 1.9 (t, 1H); 1.9 (s, 3H); 2.16 (s, 2H); 2.8 (d, 2H); 3.9 (s, 3H); 4.0 (d, 2H); 7.11 (s, 1H); 7.44 (s, 1H); 7.97 (s, 1H)

MS (ESI): 304 [MH]+

A solution of 6-methoxy-7-((1-methylpiperidin-4-yl)methoxy)-3,4-dihydroquinazolin-4-one (2.8 g, 9.24 mmol) in thionyl chloride (28 ml) containing DMF (280 µl) was refluxed at 85° C. for 1 hour. After cooling, the volatiles were removed by evaporation. The precipitate was triturated with ether, filtered, washed with ether and dried under vacuum. The solid was dissolved in methylene chloride and saturated aqueous sodium hydrogen carbonate was added. The organic layer was separated, washed with water, brine, dried (MgSO$_4$) and evaporated to give 4-chloro-6-methoxy-7-((1-methylpiperidin-4-yl)methoxy)quinazoline (2.9 g, 98%).

$^1$H NMR Spectrum: (DMSOd$_6$) 1.3-1.5 (m, 2H), 1.75-1.9 (m, 3H); 2.0 (t, 1H); 2.25 (s, 3H); 2.85 (d, 2H); 4.02 (s, 3H); 4.12 (d, 2H); 7.41 (s, 1H); 7.46 (s, 1H); 8.9 (s, 1H)

MS (ESI): 322 [MH]+

EXAMPLES 16-20

Using an analogous procedure to that described for Example 15, 4-chloro-6-methoxy-7-(1-methylpiperidin-4-yl)methoxy)quinazoline (110 mg, 0.34 mol), (prepared as described for the starting material in Example 15), was reacted with the appropriate amino pyrazole to give, as hydrochloride salts, the compounds described in Table I hereinafter.

TABLE I

| Example No. | Weight obtained mg | yield % | R | HPLC RT minutes | [MH]+ | Note |
|---|---|---|---|---|---|---|
| 16 | 168 | 90 | 4-chlorophenyl | 2.72 | 479 | 1 |
| 17 | 178 | 89 | 3,4-dichlorophenyl | 2.99 | 514 | 2 |
| 18 | 145 | 80 | 4-methylphenyl | 2.63 | 459 | 3 |
| 19 | 185 | 93 | 3-trifluoromethylphenyl | 2.87 | 513.3 | 4 |
| 20 | 140 | 86 | cyclopropyl | 2.17 | 409.5 | 5 |

HPLC conditions: column: TSK gel Super ODS 2 mm; 4.6 mm × 5 cm; eluent: gradient 0-100% acetonitrile/water (1% acetic acid) over 7 minutes; column temperature 50° C.: flow rate = 14 ml/minute; detection: UV at 254 nm.

Notes 1 4-Chloro-6-methoxy-7-((1-methylpiperidin-4-yl)methoxy)quinazoline was reacted with 3-amino-5-(4-chlorophenyl)-4H-pyrazole (76 mg), (Synthesis, 1984, 3, 276), to give Example 16.
$^1$H NMR Spectrum: (DMSOd$_6$, CD$_3$COOD) 1.55-1.75(m, 2H), 2.0-2.1(d, 2H), 2.15-2.25(m, 1H), 2.78(s, 3H), 3.05(t, 2H), 3.5(d, 2H), 4.0(s, 3H), 4.1(d, 2H), 7.29(s, 1H), 7.38(s, 1H), 7.58(d, 2H), 7.84(d, 2H), 8.3(s, 1H), 8.9(s, 1H)

2 4-Chloro-6-methoxy-7-((1-methylpiperidin-4-yl)methoxy)quinazoline was reacted with 3-amino-5-(3,4-dichlorophenyl)-4H-pyrazole (89 mg), (Synthesis, 1984, 3, 276), to give Example 17.
$^1$H NMR Spectrum: (DMSOd$_6$, CD$_3$COOD) 1.55-1.7(m, 2H), 2.05(d, 2H), 2.15-2.25(m, 1H), 2.78(s, 3H), 3.02(t, 2H), 3.5(d, 2H), 4.01(s, 3H), 4.1(d, 2H), 7.36(s, 2H), 7.7-7.8(m, 2H), 8.11(s, 1H), 8.28(s, 1H), 8.92(s, 1H)

3 4-Chloro-6-methoxy-7-((1-methylpiperidin-4-yl)methoxy)quinazoline was reacted with 3-amino-5-(4-methylphenyl)-4H-pyrazole (68 mg), (Synthesis, 1984, 3, 276), to give Example 18.
$^1$H NMR Spectrum: (DMSOd$_6$, CD$_3$COOD) 1.55-1.7(m, 2H), 2.03(d, 2H), 2.1-2.2(m, 1H), 2.36(s, 3H), 2.77(s, 3H), 3.02(t, 2H), 3.5(d, 2H), 4.02(s, 3H), 4.10(d, 2H), 7.23(s, 1H), 7.32(d, 2H), 7.40(s, 1H), 7.70(d, 2H), 8.31(s, 1H), 8.9(s, 1H)

4 4-Chloro-6-methoxy-7-((1-methylpiperidin-4-yl)methoxy)quinazoline was reacted with 3-amino-(3-trifluoromethylphenyl)-4H-pyrazole (89 mg), (WO 98/25907), to give Example 19.
$^1$H NMR Spectrum: (DMSOd$_6$, CD$_3$COOD) 1.6-1.7(m, 2H), 2.05(d, 2H), 2.15-2.25(m, 1H), 2.77(s, 3H), 3.05(t, 2H), 3.5(d, 2H), 4.0(s, 3H), 4.11(d, 2H), 7.42(d, 1H), 7.76(br s, 2H), 8.1(s, 1H), 8.19(s, 1H), 8.94(s, 1H)

5 4-Chloro-6-methoxy-7-((1-methylpiperidin-4-yl)methoxy)quinazoline was reacted with 3-amino-5-cyclopropyl-4H-pyrazole (48 mg) to give Example 20.
$^1$H NMR Spectrum: (DMSOd$_6$, CD$_3$COOD) 0.7(d, 2H), 1.05(d, 2H), 1.6-1.8(m, 2H), 1.9-2.2(m, 3H), 2.8(s, 3H), 3.05(t, 2H), 3.5(d, 2H), 4.0(s, 3H), 4.1(d, 2H), 6.6(s, 1H), 7.4(s, 1H), 8.3(s, 1H), 8.9(s, 1H)

EXAMPLE 21

A solution of 4-chloro-6-methoxy-7-((1-methylpiperidin-4-yl)methoxy)quinazoline (161 mg, 0.5 mmol), (prepared as described for the starting material in Example 15), and 3-amino-5-phenyl-4H-pyrazole (91 mg, 0.57 mmol) in isopropanol (5 ml) container 5M hydrogen chloride is isopropanol (110 μl, 0.55 mmol) was heated at reflux for 1.5 hours. After cooling, the precipitate was collected by filtration and washed with isopropanol followed by ether. The solid was partitioned between aqueous sodium hydrogen carbonate and ethyl acetate. The organic layer was separated, washed with water, brine, dried (MgSO$_4$) and the volatiles were removed by evaporation. The solid was dissolved in methylene chloride/methanol and 5M hydrogen chloride in ether was added. The volatiles were removed under vacuum and the solid was dried under vacuum to give 6-methoxy-7-((1-methylpiperidin-4-yl)methoxy-4-(5-phenylpyrazol-3-ylamino)quinazoline hydrochloride (160 mg, 72%).

MS-ESI: 445 [MH]$^-$ $^1$H NMR Spectrum: (DMSOd$_6$) 1.6-1.8 (m, 2H), 2.0-2.1 (d, 2H), 2.1-2.2 (m, 1H), 2.75 (s, 3H), 3.0 (m, 2H), 3.45 (m, 2H), 4.0 (s, 3H), 4.1 (d, 2H), 7.21 (s, 1H), 7.4 (m, 1H), 7.45-7.55 (m, 3H), 7.8 (d, 2H), 8.3 (s, 1H), 8.9 (s, 1H)

| Elemental analysis: | Found | C 52.2 | H 6.3 | N 14.4 |
|---|---|---|---|---|
| C$_{25}$H$_{28}$N$_6$O$_2$ 2.2H$_2$O 2.4HCl | Requires | C 52.5 | H 6.1 | N 14.7% |

EXAMPLE 22

Using a procedure analogous to that described in Example 15, 4-chloro-6,7-dimethoxyquinazoline (224 mg, 1 mol), (prepared as described for the starting material in Example 1), was reacted with 3-amino-5-phenyl-4H-pyrazole (183 mg, 1.16 mol) to give 6,7-dimethoxy-4-(5-phenylpyrazol-3-ylamino)quinazoline hydrochloride (328 mg, 94%).

MS-ESI: 348 [MH]

$^1$H NMR Spectrum: (DMSOd$_6$, CF$_3$COOD) 4.0 (s, 6H), 7.28 (s, 1H), 7.35 (s, 1H), 7.41 (t, 1H), 7.53 (t, 2H), 7.81 (d, 2H), 8.31 (s, 1H), 8.99 (s, 1H)

| Elemental analysis: | Found | C 54.0 | H 4.7 | N 16.5 |
|---|---|---|---|---|
| C$_{19}$H$_{17}$N$_5$O$_2$ 0.5H$_2$O 1.8HCl | Requires | C 54.1 | H 4.7 | N 16.6% |

EXAMPLE 23

A suspension of 4-chloro-6-methoxy-7-(3-morpholino-propoxy)quinazoline (150 mg, 0.44 mol), (prepared as described for the starting material in Example 2), and 3-(3-furyl)-4,5-dihydro-1H-pyrazol-5-one (80 mg, 0.53 mol) in DMF (2 ml) containing potassium carbonate (92 mg, 0.67 mol) was heated at 100° C. for 2.5 hours. After cooling, the mixture was partitioned between ethyl acetate and water. The organic layer was washed with brine, dried (MgSO$_4$) and evaporated. The residue was purified by chromatography eluting with ethyl acetate/methylene chloride (1/1) followed by methanol/ethyl acetate/methylene chloride (1/4/5), followed by methanol/methylene chloride (1/9) to give 4-(5-(3-furyl)pyrazol-3-yloxy)-6-methoxy-7-(3-morpholinopropoxy)quinazoline hydrochloride (155 mg, 77%).

$^1$H NMR Spectrum: (DMSOd$_6$, CF$_3$COOD) 2.25-2.35 (m, 2H), 3.2 (t, 2H), 3.35 (t, 2H), 3.55 (d, 2H), 3.65 (t, 2H), 4.05 (d, 2H), 4.1 (s, 3H), 4.4 (t, 2H), 6.5 (s, 1H), 6.95 (s, 1H), 7.55 (s, 1H), 7.7 (s, 1H), 7.8 (s, 1H), 8.15 (s, 1H)

MS-ESI: 4.52 [MH]$^+$

The starting material was prepared as follows:

Using an analogous procedure to that described for the preparation of the starting material in Example 9, ethyl 3-furoyl acetate (845 mg, 4.64 mmol) was reacted with hydrazine (0.25 ml, 5.16 mmol) to give 3-(3-furyl)-4,5-dihydro-1H-pyrazol-5-one (230 mg, 30%).

MS-ESI: 151 [MH]$^-$ $^1$H NMR Spectrum: (DMSOd$_6$, CF$_3$COOD) 6.15 (s, 0.5H partly exchanged), 6.96 (s, 1H), 7.84 (s, 1H), 8.35 (s, 1H)

EXAMPLES 24-31

Using an analogous procedure to that described in Example 23, 4-chloro-6-methoxy-7-(3-morpholinopropoxy)quinazoline, (prepared as described for the starting material in Example 2), was reacted with the appropriate pyrazolone to give the compounds described in Table II hereinafter.

TABLE II

| Example No. | weight obtained mg | yield % | R | [MH]$^+$ | Note |
|---|---|---|---|---|---|
| 24 | 100 | 47 | 2-fluorophenyl | 480 | 1 |
| 25 | 65 | 29 | 3-nitrophenyl | 507 | 2 |
| 26 | 65 | 29 | 4-nitrophenyl | 507 | 3 |
| 27 | 60 | 32 | propyl | 428 | 4 |
| 28 | 60 | 44 | pent-3-en-1-yl | 454 | 5 |
| 29 | 42 | 33 | methoxymethyl | 430 | 6 |
| 30 | 33 | 26 | ethyl | 414 | 7 |
| 31 | 38 | 17 | 2-phenylethyl | 490 | 8 |

Notes 1 4-Chloro-6-methoxy-7-(3-morpholinopropoxy)quinazoline was reacted with 3-(2-fluorophenyl)-4,5-dihydro-1H-pyrazol-5-one (95 mg) to give Example 24.
$^1$H NMR Spectrum: (DMSOd$_6$, CF$_3$COOD) 2.25-2.4(m, 2H), 3.15(t, 2H), 3.35(t, 2H), 3.55(d, 2H), 3.7(t, 2H), 4.05(d, 2H), 4.1(s, 3H), 4.4(t, 2H), 6.65(s, 1H), 7.3-7.4(m, 3H), 7.4-7.5(m, 1H), 7.55(s, 1H), 7.7(s, 1H), 7.9(t, 1H), 8.98(s, 1H)
The starting material was prepared as follows:
Using an analogous procedure to that described for the preparation of the starting material in Example 9, ethyl 2-fluorobenzoyl acetate was reacted with hydrazine to give 3-(2-fluorophenyl)-4,5-dihydro-1H-pyrazol-5-one (975 mg, 48%).
MS - ESI: 179 [MH]$^+$
$^1$H NMR Spectrum: (DMSOd$_6$, CF$_3$COOD) 6.1(s, 0.5H, partly exchanged), 7.3-7.45(m, 2H), 7.45-7.55(m, 1H), 7.8-7.9(t, 1H)
2 4-Chloro-6-methoxy-7-(3-morpholinopropoxy)quinazoline was reacted with 3-(3-nitrophenyl)-4,5-dihydro-1H-pyrazol-5-one (109 mg) to give Example 25.
$^1$H NMR Spectrum: (DMSOd$_6$, CF$_3$COOD) 2.25-2.4(m, 2H), 3.1-3.25(t, 2H), 3.4(t, 2H), 3.55(d, 2H), 3.7(t, 2H), 4.05(d, 2H), 4.1(s, 3H), 4.4(t, 2H), 7.0(s, 1H), 7.55(s, 1H), 7.7(s, 1H), 7.8(t, 2H), 8.25(d, 2H), 8.7(s, 1H), 8.9 (s, 1H)
The starting material was prepared as follows:
Using an analogous procedure to that described for the preparation of the starting material in Example 9, ethyl 3-nitrobenzoyl acetate was reacted with hydrazine to give 3-(3-nitrophenyl)-4,5-dihydro-1H-pyrazol-5-one (765 mg, 72%).
MS - ESI: 205 [M.]$^+$
$^1$H NMR Spectrum: (DMSOd$_6$, CF$_3$COOD) 6.32(s, 0.5H partly exchanged), 7.8(t, 1H), 8.2-8.3(m, 2H), 8.64(s, 1H)
3 4-Chloro-6-methoxy-7-(3-morpholinopropoxy)quinazoline was reacted with 3-(4-nitrophenyl)-4,5-dihydro-1H-pyrazol-5-one (109 mg) to give Example 26.
$^1$H NMR Spectrum: (DMSOd$_6$, CF$_3$COOD) 2.2-2.4(m, 2H), 3.1-3.2(m, 2H), 3.3-3.4(m, 2H), 3.55(d, 2H), 3.7(t, 2H), 4.02(d, 2H), 4.05(s, 3H), 4.35(t, 2H), 7.0(s, 1H), 7.5(s, 1H), 7.68(s, 1H), 8.1(d, 2H), 8.35(d, 2H), 8.82(s, 1H)
The starting material was prepared as follows:
Using an analogous procedure to that described for the preparation of the starting material in Example 9, ethyl 4-nitrobenzoyl acetate was reacted with hydrazine to give 3-(4-nitrophenyl)-4,5-dihydro-1H-pyrazol-5-one (630 mg, 60%).
MS - ESI: 205 [M.]$^+$
$^1$H NMR Spectrum: (DMSOd$_6$, CF$_3$COOD) 6.21(s, 0.5H partly exchanged), 8.03(d, 2H), 8.31(d, 2H)
4 4-Chloro-6-methoxy-7-(3-morpholinopropoxy)quinazoline was reacted with 3-propyl-4,5-dihydro-1H-pyrazol-5-one (67 mg) to give Example 27.
$^1$H NMR Spectrum: (DMSOd$_6$, CF$_3$COOD) 0.95(t, 3H), 1.65(q, 2H), 2.25-2.35(m, 2H), 2.62(t, 2H), 3.15(t, 2H), 3.3-3.4(m, 2H), 3.58(d, 2H), 3.7(t, 2H), 4.05(d, 2H), 4.05(s, 3H), 4.4(t, 2H), 6.05(s, 1H), 7.55(s, 1H), 7.7(s, 1H), 9.0(s, 1H)

TABLE II-continued

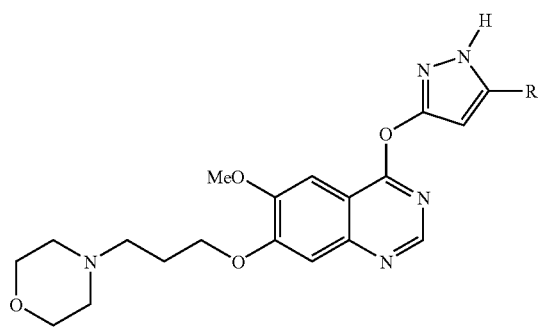

| Example No. | weight obtained mg | yield % | R | [MH]+ | Note |
|---|---|---|---|---|---|

The starting material was prepared as follows:
Using an analogous procedure to that described for the preparation of the starting material in Example 9, ethyl propylcarbonyl acetate was reacted with hydrazine to give 3-propyl-4,5-dihydro-1H-pyrazol-5-one (345 mg, 53%).
MS - ESI: 127 [MH]+
$^1$H NMR Spectrum: (DMSOd$_6$, CF$_3$COOD) 0.95(t, 3H), 1.65(q, 2H), 2.6(t, 2H), 5.8(s, 0.5H partly exchanged)
5 4-Chloro-6-methoxy-7-(3-morpholinopropoxy)quinazoline was reacted with 3-(pent-3-en-1-yl)-4,5-dihydro-1H-pyrazol-5-one (46 mg) to give Example 28.
$^1$H NMR Spectrum: (DMSOd$_6$, CF$_3$COOD) 1.6 and 1.65(2d, 3H), 2.2-2.4 (m, 4H), 2.7(t, 2H), 3.15(t, 2H), 3.4(t, 2H), 3.6(d, 2H), 3.7(t, 2H), 4.02(s, 3H), 4.05(d, 2H), 4.4(t, 2H), 5.4-5.5(m, 2H), 6.05(m, 1H), 7.5(s, 1H), 7.65 (s, 1H), 8.9(br s, 1H).
6 4-Chloro-6-methoxy-7-(3-morpholinopropoxy)quinazoline was reacted with 3-(methoxymethyl)-4,5-dhydro-1H-pyrazol-5-one (38 mg), (DE2644588), to give Example 29.
$^1$H NMR Spectrum: (DMSOd$_6$, CF$_3$COOD) 2.3-2.4(m, 2H), 3.15(t, 2H), 3.3(s, 3H), 3.35(t, 2H), 3.55(d, 2H), 3.65(t, 2H), 4.02(s, 3H), 4.05(d, 2H), 4.4(t, 2H), 4.45(s, 2H), 6.20(s, 1H), 7.5(s, 1H), 7.55(s, 1H), 8.70(br s, 1H)
7 4-Chloro-6-methoxy-7-(3-morpholinopropoxy)quinazoline was reacted with 3-ethyl-4,5-dihydro-1H-pyrazol-5-one (34 mg), (Org. Synth. 1976, 55, 73), to give Example 30.
$^1$H NMR Spectrum: (DMSOd$_6$, CF$_3$COOD): 1.25(t, 3H), 2.3(m, 2H), 2.68 (q, 2H), 3.15(t, 2H), 3.35(t, 2H), 3.55(d, 2H), 3.7(t, 2H), 4.05(s, 3H), 4.07 (d, 2H), 4.35(t, 2H), 6.05(s, 1H), 7.5(s, 1H), 7.65(s, 1H), 8.8(s, 1H)
8 4-Chloro-6-methoxy-7-(3-morpholinopropoxy)quinazoline was reacted with 3-(2-phenylethyl)-4,5-dihydro-1H-pyrazol-5-one (100 mg) to give Example 31.
$^1$H NMR Spectrum: (DMSOd$_6$, CF$_3$COOD): 2.3(m, 2H), 3.0(s, 4H), 3.2(t, 2H), 3.35(t, 2H), 3.6(d, 2H), 3.7(t, 2H), 4.05(s, 3H), 4.1(d, 2H), 4.4(t, 2H), 6.05(s, 1H), 7.15-7.35(m, 6H), 7.5(s, 1H), 7.65(s, 1H), 8.9(s, 1H)
The starting material was prepared as follows:
Using an analogous procedure to that described for the preparation of the starting material in Example 9, 2-phenylethyl propylcarbonyl acetate (1 g, 4.8 mmol) was reacted with hydrazine to give 3-(2-phenylethyl)-4,5-dihydro-1H-pyrazol-5-one (741 mg, 82%).
MS - ESI: 189 [MH]+
$^1$H NMR Spectrum: (DMSOd$_6$) 2.75(m, 2H), 2.9(m, 2H), 5.25(s, 1H), 7.1-7.25(m, 3H), 7.25-7.35(m, 2H)

EXAMPLE 32

Using a procedure analogous to that described in Example 15, 4-chloro-6-methoxy-7-((1-methylpiperidin-4-yl)methoxy)quinazoline (140 mg, 0.435 mol), (prepared as described for the starting material in Example 15), was reacted with 3-(4-methoxyphenyl)-4,5-dihydro-1H-pyrazol-5-one (100 mg, 0.52 mol), (prepared as described for the starting material in Example 10), to give 6-methoxy-7-((1-methylpiperidin-4-yl)methoxy)-4-(5-(4-methoxyphenyl) pyrazol-3-yl)quinazoline (174 mg, 84%).

MS-ESI: 476 [MH]+

$^1$H NMR Spectrum: (DMSOd$_6$, CF$_3$COOD) 1.55-1.75 (m, 2H), 2.05 (d, 2H), 2.1-2.3 (m, 1H), 2.82 (s, 3H), 3.05 (t, 2H), 3.55 (d, 2H), 3.8 (s, 3H), 4.1 (s, 3H), 4.25 (d, 2H), 6.6 (s, 1H), 7.07 (d, 2H), 7.58 (s, 1H), 7.75 (d, 2H), 9.1 (br s, 1H)

| Elemental analysis: | Found | C 64.6 | H 6.1 | N 14.7 |
|---|---|---|---|---|
| C$_{26}$H$_{29}$N$_5$O$_4$ 0.4H$_2$O | Requires | C 64.7 | H 6.2 | N 14.5% |

EXAMPLE 33

Using a procedure analogous to that described in Example 23, 4-chloro-6-methoxy-7-(2-(1,2,3-triazol-1-yl)ethoxy)quinazoline (160 mg, 0.52 mol) was reacted with 3-(4-methoxyphenyl)-4,5-dihydro-1H-pyrazol-5-one (120 mg, 0.63 mol), (prepared as described for the starting material in Example 10), to give 4-(5-(4-methoxyphenyl)pyrazol-3-yloxy)-6-methoxy-7-(2-(1,2,3-triazol-1-yl)ethoxy)quinazoline (105 mg, 44%).

MS-ESI: 460 [MH]+

$^1$H NMR Spectrum: (DMSOd$_6$, CF$_3$COOD) 3.84 (s, 3H), 4.07 (s, 3H), 4.78 (t, 2H), 5.02 (t, 2H), 6.6 (s, 1H), 7.07 (d, 2H), 7.6 (s, 1H), 7.74 (d, 1H), 7.78 (s, 1H), 7.82 (s, 1H), 8.26 (s, 1H), 9.17 (s, 1H)

| Elemental analysis: | Found | C 58.5 | H 4.6 | N 20.8 |
|---|---|---|---|---|
| C$_{23}$H$_{21}$N$_7$O$_4$ 0.6H$_2$O | Requires | C 58.7 | H 4.8 | N 20.9% |

The starting material was prepared as follows:
Triphenylphosphine (2.82 g, 10.7 mmol) was added to a solution of 2-(1,2,3-triazol-1-yl)ethanol (609 mg, 5.4 mmol), (J. Antib. 1993, 46, 177), and 7-hydroxy-6-methoxy-3-((pivaloyloxy)methyl)-3,4-dihydroquinazolin-4-one (1.1 g, 3.6 mmol), (prepared as described for the starting material in Example 7), in methylene chloride (70 ml), diethyl azodicarboxylate (600 µl, 10.7 mmol) was then added. After stirring for 2 hours at ambient temperature, the volatiles were removed by evaporation and the residue was purified by column chromatography eluting with methylene chloride/methanol (98/2) to give 6-methoxy-3-((pivaloyloxy)methyl)-7-(2-(1,2,3-triazol-1-yl)ethoxy)-3,4-dihydroquinazolin-4-one (4 g, 97%).

5.1M Ammonia in methanol (30 ml) was added to a solution of 6-methoxy-3-((pivaloyloxy)methyl)-7-(2-(1,2,3-triazol-1-yl)ethoxy)-3,4-dihydroquinazolin-4-one (1.4 g, 3.5 mmol) in a solution of methanol (30 ml). After stirring overnight at ambient temperature, the volatiles were removed by evaporation and the residue was triturated with ether, collected by filtration, washed with ether and dried under vacuum to give 6-methoxy-7-(2-(1,2,3-triazol-1-yl)ethoxy)quinazoline (946 mg, 92%).

$^1$H NMR Spectrum: (DMSOd$_6$, CF$_3$COOD) 3.9 (s, 3H); 4.6 (t, 2H); 4.9 (t, 2H); 7.25 (s, 1H); 7.52 (s, 1H); 7.77 (s, 1H); 8.19 (s, 1H); 8.9 (s, 1H)

MS-ESI: 170 [MH]−

A solution of 6-methoxy-7-(2-(1,2,3-triazol-1-yl)ethoxy)quinazoline (920 mg, 3.2 mmol) in thionyl chloride (10 ml) containing DMF (0.9 ml) was heated at 80° C. for 1 hour. After evaporation of the volatiles, the residue was azeotroped with toluene. The residue was partitioned between ethyl acetate and water and the aqueous layer was adjusted to pH8 with solid sodium hydrogen carbonate. The organic layer was washed with water, brine, dried (MgSO$_4$), and the volatiles were removed by evaporation. The residue was purified by column chromatography eluting with methylene chloride/methanol (96/4) to give 4-chloro-6-methoxy-7-(2-(1,2,3-triazol-1-yl)ethoxy)quinazoline (693 mg, 71%).

$^1$H NMR Spectrum: (CDCl$_3$) 4.1 (s, 3H); 4.55 (t, 2H); 4.95 (t, 2H); 7.3 (s, 1H); 7.4 (s, 1H); 7.75 (s, 1H); 7.95 (s, 1H); 8.85 (s, 1H)

MS-EI: 305 [MH]$^+$

| Elemental analysis: | Found | C 51.0 | H 4.0 | N 22.6% |
|---|---|---|---|---|
| C$_{13}$H$_{12}$N$_5$O$_2$Cl | Requires | C 51.0 | H 3.9 | N 22.9% |

EXAMPLE 34

A suspension of 4-chloro-6-methoxy-7-(1-(2-methylsulphonylethyl)piperidin-4-ylmethoxy)quinazoline (115 mg, 0.28 mol) and 3-(4-methoxyphenyl)-4,5-dihydro-1H-pyrazol-5-one (65 mg, 0.33 mol), (prepared as described for the starting material in Example 10), in DMF (1.5 ml) containing potassium carbonate (60 mg, 0.42 mol) was heated at 100° C. for 30 minutes. After cooling, water was added. The precipitate was collected by filtration, washed with water and dried under vacuum. The solid was dissolved in methylene chloride/methanol and pentane was added. The precipitate was collected by filtration, washed with pentane and dried under vacuum to give 4-(5-(4-methoxyphenyl)pyrazol-3-yloxy)-6-methoxy-7-(1-(2-methylsulphonylethyl)piperidin-4-ylmethoxy)quinazoline (120 mg, 75%).

MS-ESI: 568 [MH]$^-$ $^1$H NMR Spectrum: (DMSOd$_6$, CF$_3$COOD) 1.3-1.4 (m, 2H), 1.8-1.9 (m, 3H), 2.0 (t, 2H), 2.7 (t, 2H), 2.95 (d, 2H), 3.05 (s, 3H), 3.25-3.3 (m, 2H), 3.8 (s, 3H), 4.0 (s, 3H), 4.1 (d, 2H), 6.6 (s, 1H), 7.05 (d, 2H), 7.4 (s, 1H), 7.55 (s, 1H), 7.7 (d, 2H), 8.6 (s, 1H)

| Elemental analysis: | Found | C 57.1 | H 5.9 | N 12.1 |
|---|---|---|---|---|
| C$_{28}$H$_{33}$N$_5$O$_6$S 0.6H$_2$O | Requires | C 58.1 | H 6.0 | N 12.1% |

The starting material was prepared as follows:

A suspension of 7-hydroxy-6-methoxy-3-((pivaloyloxy)methyl-3,4-dihydroquinazolin-4-one (6.12 g, 20 mmol), (prepared as described for the starting material in Example 7) and potassium carbonate (5.52 g, 40 mmol) in DMF (60 ml) was stirred at ambient temperature for 30 minutes. 4-(4-Methylphenylsulphonyloxymethyl)-1-tert-butyloxycarbonylpiperidine (8.86 g, 24 mmol), (prepared as described for the starting material in Example 15), was added and the mixture was stirred at 100° C. for 2 hours. After cooling, the mixture was poured onto water/ice (400 ml, 1/1) containing 2M hydrochloric acid (10 ml). The precipitate was collected by filtration, washed with water and dried under vacuum over phophorus pentoxide. The solid was triturated in a mixture of ether/pentane (1/1), collected by filtration and dried to give 6-methoxy-3-((pivaloyloxy)methyl)-7-((tert-butyloxycarbonylpiperidin-4-yl)methoxy)-3,4-dihydroquinazolin-4-one (7.9 g, 78.5%).

$^1$H NMR Spectrum: (DMSOd$_6$) 1.1 (s, 9H); 1.1-1.3 (m, 2H); 1.42 (s, 9H); 1.73 (d, 2H); 1.93-2.1 (br s, 1H); 2.65-2.9 (br s, 2H); 3.9 (s, 3H); 3.9-4.1 (m, 4H); 5.9 (s, 2H); 7.2 (s, 1H); 7.5 (s, 1H); 8.35 (s, 1H)

MS (ESI): 526 [MNa]+

A solution of 6-methoxy-3-((pivaloyloxy)methyl)-7-((1-tert-butyloxycarbonylpiperidin-4-yl)methoxy)-3,4-dihydroquinazolin-4-one (7.9 g, 16 mmol) in methylene chloride (80 ml) containing 5.5M hydrogen chloride in isopropanol (80 ml) was stirred for 1 hour at ambient temperature. Ether was added and the solid was collected by filtration, washed with ether and dried under vacuum at 60° C. to give 6-methoxy-7-((piperidin-4-yl)methoxy)-3-((pivaloyloxy)methyl)-3,4-dihydroquinazolin-4-one hydrochloride (6.9 g, 100%).

$^1$H NMR Spectrum: (DMSOd$_6$, CF$_3$CO$_2$D) 1.15 (s, 9H); 1.5-1.7 (m, 2H); 2.0 (d, 2H); 2.2-2.3 (br s, 1H); 3.0 (t, 2H); 3.4 (d, 2H); 3.94 (s, 3H); 4.15 (d, 2H); 5.97 (s, 2H); 7.3 (s, 1H); 7.6 (s, 1H); 8.65 (s, 1H)

MS (ESI): 404 [MH]$^-$

Potassium carbonate (280 mg, 2 mmol) and methyl vinyl sulfone (0.4 ml, 2.1 mmol) were added to a solution of 6-methoxy-7-((piperidin-4-yl)methoxy)-3-((pivaloyloxy)methyl)-3,4-dihydroquinazolin-4-one hydrochloride (0.88 g, 2 mmol) and triethylamine (0.3 ml, 2.1 mmol) in methanol (10 ml) and methylene chloride (10 ml). After stirring for 2 hours at ambient temperature, the volatiles were removed under vacuum. The residue was partitioned between ethyl acetate and water. The organic layer was washed with brine, dried (MgSO$_4$) and evaporated to give 6-methoxy-7-((1-(2-methylsulphonylethyl)piperidin-4-yl)methoxy)-3-((pivaloyloxy)methyl)-3,4-dihydroquinazolin-4-one (0.55 g, 54%).

$^1$H NMR Spectrum: (DMSOd$_6$) 1.09 (s, 9H); 1.25-1.4 (m, 2H); 1.7-1.9 (m, 3H); 2.0 (t, 2H); 2.7 (t, 2H); 2.95 (d, 2H); 3.02 (s, 3H); 3.25-3.45 (m, 2H); 3.9 (s, 3H); 4.0 (d, 2H); 5.9 (s, 2H); 7.15 (s, 1H); 7.49 (s, 1H); 8.35 (s, 1H)

MS (ESI): 510 [MH]$^+$.

2M Aqueous sodium hydroxide (180 µl, 0.35 mmol) was added to a suspension of 6-methoxy-7-((1-(2-methylsulphonylethyl)piperidin-4-yl)methoxy)-3-((pivaloyloxy)methyl)-3,4-dihydroquinazolin-4-one (90 mg, 0.18 mmol) in methanol (3 ml). After stirring for 2 hours at ambient temperature, the mixture was adjusted to pH10 with 2M hydrochloric acid. The volatiles were removed under vacuum and the residue was suspended in water, filtered, washed with water followed by ether and dried under vacuum at 60° C. to give 6-methoxy-7-((1-(2-methylsulphonylethyl)piperidin-4-yl)methoxy)-3,4-dihydroquinazolin-4-one (55 mg, 79%).

$^1$H NMR Spectrum: (DMSOd$_6$) 1.2-1.4 (m, 2H); 1.7-1.85 (m, 3H); 2.0 (t, 2H); 2.7 (t, 2H); 2.9 (d, 2H); 3.02 (s, 3H); 3.3-3.5 (m, 2H); 3.9 (s, 3H); 4.0 (d, 2H); 7.11 (s, 1H); 7.45 (s, 1H); 7.97 (s, 1H)

MS (ESI): 396 [MH]$^+$

A solution of 6-methoxy-7-((1-(2-methylsulphonylethyl)piperidin-4-yl)methoxy)-3,4-dihydroquinazolin-4-one (335 mg, 0.85 mmol) in thionyl chloride (5 ml) containing DMF (50 µl) was heated at reflux for 1 hour. After cooling, the volatiles were removed under vacuum and the residue was triturated with ether and filtered. The solid was suspended in methylene chloride and sodium hydrogen carbonate was added. The organic layer was washed with water, brine, dried (MgSO$_4$) and evaporated. The residue was triturated with ether, filtered and dried under vacuum to give 4-chloro-6-methoxy-7-((1-(2-methylsulphonylethyl)piperidin-4-ylmethoxy)quinazoline (335 mg, 95%).

$^1$H NMR Spectrum: (DMSOd$_6$) 1.25-1.45 (m, 2H); 1.75-1.90 (m, 3H); 2.0 (t, 2H); 2.7 (t, 2H); 2.92 (d, 2H); 3.03 (s, 3H); 3.2-3.35 (m, 2H); 4.0 (s, 3H); 4.1 (d, 2H); 7.40 (s, 1H); 7.45 (s, 1H); 8.9 (s, 1H)

MS (ESI): 414 [MH]

EXAMPLE 35

Using a procedure analogous to that described in Example 14, 4-chloro-6-methoxy-7-(3-(4-methylpiperazin-1-yl)propoxy)quinazoline (350 mg, 1 mol), (prepared as described for the starting material in Example 14), was reacted with 3-(4-methoxyphenyl)-4,5-dihydro-1H-pyrazol-5-one (380 mg, 2 mol), (prepared as described for the starting material in Example 10), to give 4-(5-(4-methoxyphenyl)pyrazol-3-yloxy)-6-methoxy-7-(3-(4-methylpiperazin-1-yl)propoxy)quinazoline (215 mg, 43%).

MS-ESI: 505 [MH]+

$^1$H NMR Spectrum: (DMSOd$_6$, CD$_3$COOD), (60° C.), 2.3-2.4 (m, 2H), 2.95 (s, 3H), 3.45 (t, 2H), 3.55-3.7 (m, 8H), 3.8 (s, 3H), 4.05 (s, 3H), 4.4 (t, 2H), 6.55 (s, 1H), 7.05 (d, 2H), 7.55 (s, 1H), 7.55 (d, 2H), 7.75 (s, 1H), 8.9 (s, 1H)

EXAMPLE 36

A suspension of 4-chloro-6-methoxy-7-(3-morpholinopropoxy)quinazoline (150 mg, 0.44 mol), (prepared as described for the starting material in Example 2), and 3-isobutyl-4,5-dihydro-1H-pyrazol-5-one (75 mg, 0.53 mol), (Org. Synth. 1976, 55, 73), in DMF (2 ml) containing potassium carbonate (92 mg, 0.67 mol) was heated at 100° C. for 2.5 hours. After cooling, water was added and the aqueous layer was adjusted to pH6.5 with 2M hydrochloric acid. Ethyl acetate was added. The organic layer was separated, washed with water, brine, dried (MgSO$_4$) and the volatiles were removed by evaporation. The residue was purified by column chromatography eluting the ethyl acetate/methylene chloride (1/1) followed by methanol/ethyl acetate/methylene chloride (1/4/5) and by methanol/methylene chloride (1/9) to give 4-(5-isobutylpyrazol-3-yloxy)-6-methoxy-7-(3-morpholinopropoxy)quinazoline (85 mg, 43%).

MS-ESI: 441 [MH]+

$^1$H NMR Spectrum: (DMSOd$_6$, CF$_3$COOD) 0.91 (d, 6H), 1.9 (m, 1H), 2.2-2.4 (m, 2H), 3.15 (t, 2H), 3.35 (t, 2H), 3.55 (d, 2H), 3.7 (t, 2H), 4.03 (d, 2H), 4.05 (s, 3H), 4.35 (t, 2H), 6.02 (s, 1H), 7.55 (s, 1H), 7.7 (s, 1H), 9.1 (s, 1H)

EXAMPLES 37-38

Using an analogous procedure to that described in Example 36, 4-chloro-6-methoxy-7-(3-morpholinopropoxy)quinazoline (150 mg, 0.44 mol), (prepared as described for the starting material in Example 2), was reacted with the appropriate pyrazolone to give the compounds described in Table III hereinafter.

TABLE III

| Example No. | weight obtained mg | yield % | R | [MH]+ | Note |
|---|---|---|---|---|---|
| 37 | 100 | 51 | butyl | 442 | 1 |
| 38 | 60 | 28 | 2-cyclopentylethyl | 482 | 2 |

1 4-Chloro-6-methoxy-7-(3-morpholinopropoxy)quinazoline was reacted with 3-butyl-4,5-dihydro-1H-pyrazol-5-one (75 mg), (Synthesis, 1982, 12, 1100), to give Example 37.
$^1$H NMR Spectrum: (DMSOd$_6$, CF$_3$COOD): 0.9(t, 3H), 1.3-1.45(m, 2H), 1.55-1.7(m, 2H), 2.3-2.4(m, 2H), 2.6(t, 2H), 3.2(t, 2H), 3.35(t, 2H), 3.55 (d, 2H), 3.7(t, 2H), 4.02(s, 3H), 4.04(d, 2H), 4.35(t, 2H), 6.0(s, 1H), 7.5(s, 1H), 7.66(s, 1H), 8.95(s, 1H)

2 4-Chloro-6-methoxy-7-(3-morpholinopropoxy)quinazoline was reacted with 3-(2-cyclopentylethyl)-4,5-dihydro-1H-pyrazol-5-one (96 mg) to give Example 38.
$^1$H NMR Spectrum: (DMSOd$_6$, CF$_3$COOD): 1.05-1.2(m, 2H), 1.4-1.9(m, 1.1H), 2.3(br s, 2H), 2.65(t, 2H), 3.15(br s, 2H), 3.35(t, 2H), 3.55(d, 2H), 3.7(t, 2H), 4.0(s, 3H), 4.02(d, 2H), 4.35(br s, 2H), 6.0(s, 1H), 7.5(s, 1H), 7.65(s, 1H), 8.9(s, 1H)

The starting material was prepared as follows:

3-Cyclopentylpropionyl chloride (0.64 ml, 4.16 mmol) was added to a solution of 2,2-dimethyl-1,3-dioxane-4,6-dione (500 mg, 3.47 mmol) in anhydrous methylene chloride (10 ml). After cooling to 0° C., pyridine (0.56 ml, 6.94 mmol) was added in portions. After stirring for 1 hour at 0° C. and 2 hours at ambient temperature the mixture was poured onto water (20 ml) containing concentrated hydrochloric acid (0.5 ml). The organic layer was separated, washed with water, brine, dried (MgSO$_4$) and the volatiles were removed by evaporation to give 5-(3-cyclopentylpropionyl)-2,2-dimethyl-1,3-dioxane-4,6-dione (900 mg, 96%).

$^1$H NMR Spectrum: (CDCl$_3$) 1.0-1.2 (m, 4H), 1.45-1.9 (m, 11H), 2.35-2.55 (m, 2H), 3.1 (t, 2H)

A solution of 5-(3-cyclopentylpropionyl)-2,2-dimethyl-1,3-dioxane-4,6-dione (900 mg, 3.3 mmol) in ethanol (5 ml) containing hydrazine (0.43 ml, 8.84 mmol) was stirred at ambient temperature for 20 minutes followed by stirring for 2 hours at 75° C. The volatiles were removed under vacuum and the residue was triturated with ether. The solid was collected by filtration, washed with ether and dried under vacuum to give 3-(2-cyclopentylethyl)-4,5-dihydro-1H-pyrazol-5-one (250 mg, 42%).

MS-ESI: 181 [MH]

$^1$H NMR Spectrum: (DMSOd$_6$, CF$_3$COOD) 1.0-1.2 (m, 2H), 1.4-1.8 (m, 9H), 2.6 (t, 2H), 5.8 (s, 0.5H partly exchanged)

EXAMPLE 39

Using a procedure analogous to that described in Example 34, 4-chloro-6-methoxy-7-(3-methylsulphonylpropoxy)quinazoline (150 mg, 0.45 mol) was reacted with 3-(4- methoxyphenyl)-4,5-dihydro-1H-pyrazol-5-one (105 mg, 0.54 mol), (prepared as described for the starting material in Example 10), to give 4-(5-(4-methoxyphenyl)pyrazol-3-yloxy)-6-methoxy-7-(3-methylsulphonylpropoxy)quinazoline (220 mg, 91%).

MS-ESI: 485 [MH]+

$^1$H NMR Spectrum: (DMSOd$_6$, CF$_3$COOD) 2.35 (m, 2H); 3.05 (s, 3H), 3.35 (t, 2H), 3.8 (s, 3H), 4.1 (s, 3H), 4.4 (t, 2H), 6.6 (s, 1H), 7.05 (d, 2H), 7.55 (s, 1H), 7.7 (d, 2H), 7.74 (s, 1H), 9.14 (s, 1H)

| Elemental analysis: | Found | C 56.5 | H 5.3 | N 11.6 |
|---|---|---|---|---|
| C$_{23}$H$_{24}$N$_4$O$_6$S, 0.1H$_2$O | Requires | C 56.8 | H 5.0 | N 11.5% |

The starting material was prepared as follows:

Triphenylphosphine (8.9 g, 35.2 mmol) was added to a suspension of 7-hydroxy-6-methoxy-3-((pivaloyloxy)methyl)-3,4-dihydroquinazolin-4-one (6 g, 19.6 mmol), (prepared as described for the starting material in Example 7), in methylene chloride (150 ml). This was followed by the addition of 3-methylsulphonylpropanol (3.5 g, 25.4 mmol) and diethylazodicarboxylate (5.55 ml, 35.2 mmol) in portions. The reaction was complete once the reaction became homogeneous. Silica was added and the volatiles were removed by evaporation. The free flowing powder was placed on the top of a flash chromatography column pre-equilibrated with ethyl acetate (100%). Elution was done using ethyl acetate (100%) followed by methylene chloride/ethyl acetate/methanol (60/35/3). The volatiles were removed by evaporation to give 6-methoxy-7-(3-methylsulphonylpropoxy)-3-((pivaloyloxy)methyl)-3,4-dihydroquinazolin-4-one (7.58 g, 91%) as a white solid.

$^1$H NMR Spectrum: (CDCl$_3$) 1.2 (s, 9H); 2.4-2.5 (m, 2H); 3.0 (s, 3H); 3.25-3.35 (t, 2H); 5.95 (s, 1H); 7.1 (s, 1H); 7.65 (s, 1H); 8.2 (s, 1H)

6-Methoxy-7-(3-methylsulphonylpropoxy)-3-((pivaloyloxy)methyl)-3,4-dihydroquinazolin-4-one (7 g, 17 mmol) was suspended in methanol and 2M sodium hydroxide (3.3 ml, 6.6 mmol) was added with continuous stirring. The reaction mixture became homogeneous after 15 minutes. After a further 45 minutes water was added (7 ml) and the reaction mixture was adjusted to pH10 with 2M hydrochloric acid. The precipitate (a white solid) was collected by filtration, washed with water and dried over phosphorus pentoxide under vacuum to give 6-methoxy-7-(3-methylsulphonylpropoxy)-3,4-dihydroquinazolin-4-one (5 g, 90%).

$^1$H NMR Spectrum: (DMSOd$_6$) 2.2-2.3 (m, 2H); 3.05 (s, 3H); 3.35 (t, 2H); 3.9 (s, 3H); 4.25 (t, 2H); 7.15 (s, 1H); 7.5 (s, 1H); 8.0 (s, 1H)

6-Methoxy-7-(3-methylsulphonylpropoxy)-3,4-dihydroquinazolin-4-one (3.6 g, 11.5 mmol) was suspended in thionyl chloride (40 ml). DMF (1.8 ml) was added under argon and the mixture was heated at reflux for 1.5 hours. The thionyl chloride was eliminated by several azeotropic distillations using toluene. The solid residue was suspended in ice/water and a saturated solution of sodium hydrogen carbonate was added to adjust the mixture to pH7. The solid was collected by filtration, washed with water and dried in a vacuum dessicator over phosphorus pentoxide to give 4-chloro-6-methoxy-7-(3-methylsulphonylpropoxy)quinazoline (3.35 g, 88%).

$^1$H NMR Spectrum: (DMSOd$_6$) 2.2-2.3 (m, 2H); 3.05 (s, 3H); 3.3-3.4 (m, 2H); 4.01 (s, 3H); 4.4 (t, 2H); 7.41 (s, 1H); 7.47 (s, 1H); 8.88 (s, 1H)

EXAMPLE 40

The following illustrate representative pharmaceutical dosage forms containing the compound of formula I, or a pharmaceutically acceptable salt thereof (hereafter compound X), for therapeutic or prophylactic use in humans.

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1N Sodium hydroxide solution | 15.0% v/v |
| | 0.1N Hydrochloric acid | |
| | (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1N Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note
The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound of the formula II:

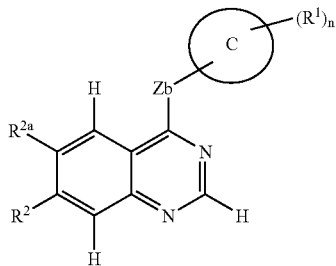

wherein:
ring C is pyrazolyl;
Zb is —O— or —S—;
$R^1$ represents hydrogen, $C_{1-4}$alkyl, $C_{1-4}$alkoxymethyl, di($C_{1-4}$)alkoxy)methyl, $C_{1-4}$alkanoyl, trifluoromethyl, cyano, amino, $C_{2-5}$alkenyl, $C_{2-5}$alkynyl, a phenyl group, a benzyl group or a 5-6-membered heterocyclic group with 1-3 heteroatoms, selected independently from O, S and N, which heterocyclic group may be aromatic or non-aromatic and may be saturated and linked via a ring carbon or nitrogen atom, or unsaturated and linked via a ring carbon atom, and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, $C_{1-4}$alkylamino, $C_{1-4}$hydroxyalkyl, $C_{1-4}$aminoalkyl, $C_{1-4}$haloalkyl, $C_{1-4}$hydroxyalkoxy, carboxy and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$-alkanoyloxy, trifluoromethyl, cyano, amino, nitro and $C_{1-4}$alkoxycarbonyl; and additionally $R^1$ may represent carboxy, $C_{3-7}$cycloalkyl, $C_{3-7}$cycloalkyl$C_{1-3}$alkyl, or phenyl$C_{2-4}$alkyl wherein the phenyl moiety may bear up to 5 substituents selected from the list herein defined for a phenyl ring which is directly linked to ring C;
n is an integer from 0 to 5;
m is an integer from 0 to 3;
$R^2$ represents hydroxy, nitro, trifluoromethyl, cyano, amino or $R^5X^1$— wherein $X^1$ represents a direct bond, —O—, —$CH_2$—, —OCO—, carbonyl, —S—, —SO—, —$SO_2$—, —$NR^6CO$—, —$CONR^7$—, —$SO_2NR^8$, —$NR^9SO_2$— or —$NR^{10}$—, wherein $R^6$, $R^7$, $R^8$, $R^9$ and $R^{10}$ each independently represents hydrogen, $C_{1-3}$alkyl or $C_{1-3}$alkoxy$C_{2-3}$alkyl, and $R^5$ is selected from one of the following eighteen groups:
1) $C_{1-4}$alkyl which may be unsubstituted or substituted with one or more fluorine atoms, or $C_{2-4}$alkyl which may be unsubstituted or substituted with 1 or 2 groups selected from hydroxy and amino;
2) $C_{2-3}$alkyl$X^2COR^{11}$, wherein $X^2$ represents —O— or —$NR^{12}$—, in which $R^{12}$ represents hydrogen, $C_{1-3}$alkyl or $C_{1-3}$alkoxy$C_{2-3}$alkyl, and $R^{11}$ represents —$NR^{13}R^{14}$ or —$OR^{15}$, wherein $R^{13}$, $R^{14}$ and $R^{15}$ which may be the same or different are each $C_{1-2}$alkyl or $C_{1-2}$alkoxyethyl;
3) $C_{2-4}$alkyl$X^3R^{16}$, wherein $X^3$ represents —O—, —S—, —SO—, —$SO_2$—, —OCO—, —$NR^{17}CO$—, —$CONR^{18}$—, —$SO_2NR^{19}$, —$NR^{20}SO_2$— or —$NR^{21}$—, wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl, and $R^{16}$ is a group selected from $C_{1-3}$alkyl, cyclopentyl, cyclohexyl, pyrrolidinyl and piperidinyl which group is linked to $X^3$ through a carbon atom and which $C_{1-3}$alkyl group may bear 1 or 2 substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy;
4) $C_{2-3}$alkyl$X^4C_{2-3}$alkyl$X^5R^{22}$, wherein $X^4$ and $X^5$, which may be the same or different, are each —O—, —S—, —SO—, —$SO_2$—, —$NR^{23}CO$—, —$CONR^{24}$—, —$SO_2NR^{25}$—, —$NR^{26}SO_2$— or —$NR^{27}$—, wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl, and $R^{22}$ represents hydrogen or $C_{1-3}$alkyl;
5) $C_{1-4}$alkyl$R^{59}$, wherein $R^{59}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry 1 or 2 substituents selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl or $C_{2-4}$alkyl$R^{60}$, wherein $R^{60}$ is a group selected from morpholino, thiomorpholino, pyrrolidin-1-yl, piperazin-1-yl and piperidino which group may carry 1 or 2 substituents selected from oxo, hydroxy, halogeno, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl;
6) $C_{3-4}$alkenyl$R^{61}$, wherein $R^{61}$ represents $R^{59}$ or $R^{60}$ as defined herein;
7) $C_{3-4}$alkynyl$R^{61}$, wherein $R^{61}$ represents $R^{59}$ or $R^{60}$ as defined herein;
8) $R^{29}$, wherein $R^{29}$ represents a pyridone group, a phenyl group or a 5-6-membered aromatic heterocyclic group, linked via carbon or nitrogen, with 1-3 heteroatoms selected from O, N and S, which pyridone, phenyl or aromatic heterocyclic group may carry up to 5 substituents on an available carbon atom selected from hydroxy, halogen, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{30}R^{31}$ and —$NR^{32}COR^{33}$, wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl;
9) $C_{1-4}$alkyl$R^{29}$, wherein $R^{29}$ is as defined herein;
10) 1-$R^{29}$prop-1-en-3-yl or 1-$R^{29}$but-2-en-4-yl, wherein $R^{29}$ is as defined herein with the proviso that when $R^5$ is 1-$R^{29}$prop-1-en-3-yl, $R^{29}$ is linked to the alkenyl group via a carbon atom;

11) 1-$R^{29}$prop-1-yn-3-yl or 1-$R^{29}$but-2-yn-4-yl, wherein $R^{29}$ is as defined herein with the proviso that when $R^5$ is 1-$R^{29}$prop-1-yn-3-yl, $R^{29}$ is linked to the alkynyl group via a carbon atom;
12) $C_{1-5}$alkyl$X^6X^{29}$, wherein $X^6$ represents —O—, —S—, —SO—, —SO$_2$—, —NR$^{34}$CO—, —CONR$^{35}$—, —SO$_2$NR$^{36}$—, —NR$^{37}$SO$_2$— or —NR$^{38}$—, wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl, and $R^{29}$ is as defined herein;
13) 1-($R^{29}X^7$)but-2-en-4-yl, wherein $X^7$ represents —O—, —S—, —SO—, —SO$_2$—, —NR$^{39}$CO—, —CONR$^{40}$—, —SO$_2$NR$^{41}$—, —NR$^{42}$SO$_2$— or —NR$^{43}$—, wherein $R^{39}$, $R^{40}$, $R^{41}$, $R^{42}$ and $R^{43}$ each independently represents hydrogen, $C_{1-3}$alkyl or $C_{1-3}$-alkoxy$C_{2-3}$alkyl, and $R^{29}$ is as defined herein;
14) 1-($R^{29}X^8$)but-2-yn-4-yl, wherein $X^8$ represents —O—, —S—, —SO—, —SO$_2$—, —NR$^{44}$CO—, —CONR$^{45}$—, —SO$_2$NR$^{46}$—, —NR$^{47}$SO$_2$— or —NR$^{48}$—, wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl, and $R^{29}$ is as defined herein;
15) $C_{2-3}$alkyl$X^9C_{1-2}$alkyl$R^{29}$, wherein $X^9$ represents —O—, —S—, —SO—, —SO$_2$—, —NR$^{49}$CO—, —CONR$^{50}$—, —SO$_2$NR$^{51}$—, —NR$^{52}$SO$_2$— or —NR$^{53}$—, wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl, and $R^{29}$ is as defined herein;
16) $R^{28}$, wherein $R^{28}$ is a 5-6-membered saturated heterocyclic group, linked via carbon or nitrogen, with 1-2 heteroatoms selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl and $C_{1-4}$alkoxycarbonyl;
17) $C_{2-3}$alkyl$X^9C_{1-2}$alkyl$R^{28}$, wherein $X^9$ and $R^{28}$ are as defined herein; and
18) $C_{2-3}$alkyl$R^{54}C_{1-2}$alkyl$X^9R^{55}$, wherein $X^9$ is as defined herein, and $R^{54}$ and $R^{55}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$cyanoalkyl and $C_{1-4}$alkoxycarbonyl, with the proviso that $R^{54}$ cannot be hydrogen;

and additionally wherein any $C_{1-5}$alkyl, $C_{2-5}$alkenyl or $C_{2-5}$alkynyl group in $R^5X^1$— may bear one or more substituents selected from hydroxy, halogeno and amino; provided that $R^2$ is not hydrogen, substituted or unsubstituted $C_{1-5}$alkyl, $C_{1-5}$alkoxy, phenoxy or phenyl$C_{1-5}$alkoxy; and $R^{2a}$ represents hydrogen, halogeno, $C_{1-3}$alkyl, $C_{1-3}$alkoxy, $C_{1-3}$alkylthio, —NR$^{3a}R^{4a}$, wherein $R^{3a}$ and $R^{4a}$, which may be the same or different, each represents hydrogen or $C_{1-3}$alkyl, or $R^{5a}(CH_2)_{za}X^{1a}$, wherein $R^{5a}$ is a 5- or 6-membered saturated heterocyclic group with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl and $C_{1-4}$alkoxy, za is an integer from 0 to 4 and $X^{1a}$ represents a direct bond, —O—, —CH$_2$—, —S—, —SO—, —SO$_2$—, —NR$^{6a}$CO—, —CONR$^{7a}$—, —SO$_2$NR$^{8a}$—, —NR$^{9a}$SO$_2$— or —NR$^{10a}$—, wherein $R^{6a}$, $R^{7a}$, $R^{8a}$, $R^{9a}$ and $R^{10a}$ each independently represents hydrogen, $C_{1-3}$alkyl or $C_{1-3}$alkoxy$C_{2-3}$alkyl;

or a salt thereof.

2. A compound as claimed in claim 1 wherein Zb is —O—.

3. A compound as claimed in claim 1 wherein $R^{2a}$ is methoxy.

4. A compound as claimed in claim 1 wherein $R^1$ is a phenyl group or a 5-6-membered heteroaromatic group with 1-3 heteroatoms, selected independently from O, S and N, (linked via a ring carbon atom), which phenyl or heteroaromatic group is optionally substituted as defined in claim 1.

5. A compound as claimed in claim 1 wherein $R^2$ represents 2-methoxyethoxy, 2-(2-methoxyethoxy)ethoxy, 3-methoxypropoxy, 2-methylsulphonylethoxy, 3-methylsulphonylpropoxy, 2-(tetrahydropyran-4-yloxy)ethoxy, 3-(tetrahydropyran-4-yloxy)propoxy, 2-(4-methylpiperazin-1-yl)ethoxy, 3-(4-methylpiperazin-1-yl)propoxy, 2-morpholinoethoxy, 3-morpholinopropoxy, 2-(imidazol-1-yl)ethoxy, 3-(imidazol-1-yl)propoxy 2-(1,1-dioxothiomorpholino)ethoxy, 3-(1,1-dioxothiomorpholino)propoxy, 2-(1,2,3-triazol-1-yl)ethoxy, 3-(1,2,3-triazol-1-yl)propoxy, 2-(N-methoxyacetyl-N-methylamino)ethoxy, 3-(N-methoxyacetyl-N-methylamino)propoxy, N-methylpiperidin-3-ylmethoxy, 4-(pyrrolidin-1-yl)but-2-en-yloxy, 2-(2-oxopyrrolidin-1-yl)ethoxy, 3-(2-oxopyrrolidin-1-yl)propoxy, 2-(pyrrolidin-1-yl)ethoxy, 3-(pyrrolidin-1-yl)propoxy, 2-(2-(pyrrolidin-1-yl)ethoxy)ethoxy, 2-(2-(4-methylpiperazin-1-yl)ethoxy)ethoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(methylpiperidin-3-yl)ethoxy, 2-(methylpiperidin-4-yl)ethoxy, 3-(methylpiperidin-3-yl)propoxy, 3-(methylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 3-(4-methylpiperazin-1-yl)propoxy, 1-methylpiperidin-4-ylmethoxy, 1-(2-methylsulphonylethyl)piperidin-4-ylmethoxy, 1-(2-pyrrolidinylethyl)piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2- azetidinylethyl)piperidin-4-ylmethoxy or 1-(3-azetidinylpropyl)piperidin-4-ylmethoxy.

6. A compound as claimed in claim 1 selected from:
4-(5-(4-methoxyphenyl)pyrazol-3-yloxy)-6-methoxy-7-(1-methylpiperidin-4-ylmethoxy)quinazoline,
4-(5-(4-methoxyphenyl)pyrazol-3-yloxy)-6-methoxy-7-(3-(4-methylpiperidin-1-yl)propoxy)quinazoline,
6-methoxy-7-(2-(2-methoxyethoxy)ethoxy)-4-(5-phenylpyrazol-3-yloxy)quinazoline,
4-(5-(3-furyl)pyrazol-3-yloxy)-6-methoxy-7-(3-morpholinopropoxy)quinazoline,
6-methoxy-7-(3-morpholinopropoxy)-4-(5-phenylpyrazol-3-yloxy)quinazoline,
7-(2-(imidazol-1-yl)ethoxy)-6-methoxy-4-(5-phenylpyrazol-3-yloxy)quinazoline,
4-(5-(4-chlorophenyl)pyrazol-3-yloxy)-6-methoxy-7-(3-morpholinopropoxy)quinazoline,
6-methoxy-7-(3-(4-methylpiperazin-1-yl)propoxy)-4-(5-phenylpyrazol-3-yloxy)-quinazoline,
6-methoxy-7-(2-methoxyethoxy)-4-(5-phenylpyrazol-3-yloxy)quinazoline,
4-(5-(4-methoxyphenyl)pyrazol-3-yloxy)-6-methoxy-7-(2-(1,2,3-triazol-1-yl)ethoxy)quinazoline and
4-(5-(4-methoxyphenyl)pyrazol-3-yloxy)-6-methoxy-7-(1-(2-methylsulphonylethyl)piperidin-4-ylmethoxy)quinazoline,
and salts thereof.

7. A compound as claimed in claim 1 selected from:
7-(2-methoxyethoxy)-4-(5-phenylpyrazol-3-yloxy)quinazoline,
4-(5-(2-fluorophenyl)pyrazol-3-yloxy)-6-methoxy-7-(3-morpholinopropoxy)quinazoline,
6-methoxy-7-(3-morpholinopropoxy)-4-(5-(3-nitrophenyl)pyrazol-3-yloxy)quinazoline,
6-methoxy-7-(3-morpholinopropoxy)-4-(5-(4-nitrophenyl)pyrazol-3-yloxy)quinazoline,
6-methoxy-7-(3-morpholinopropoxy)-4-(5-(4-pyridyl)pyrazol-3-yloxy)quinazoline,
4-(5-(4-fluorophenyl)pyrazol-3-yloxy)-6-methoxy-7-(3-morpholinopropoxy)quinazoline, and
6-methoxy-7-(2-methoxyethoxy)-4-(5-(4-methoxyphenyl)pyrazol-3-yloxy)quinazoline,
and salts thereof.

8. A compound as claimed in any one of claims 1 and 2-3, 4 and 5 to 7 in the form of a pharmaceutically acceptable salts.

9. A pharmaceutical composition which comprises as active ingredient a compound of formula II or a pharmaceutically acceptable salt thereof as claimed in any one of claims 1 and 2-3, 4 and 5 to 7 in association with a pharmaceutically acceptable excipient or carrier.

10. A process for the preparation of a compound of formula II or salt thereof, as defined in claim 1, wherein, unless otherwise defined herein, Z herein is $Z^b$ as defined in claim 1, $R^2$ herein when at the 7-position of the quinazoline ring is $R^2$ as defined in claim 1, $R^2$ herein when at the 6-position of the quinazoline ring is $R^{2a}$ as defined in claim 1, and ring C, $R^1$, n, m, $R^5$ and $X^1$ herein are as defined in claim 1, said process comprising:

(a) the reaction of a compound of the formula III:

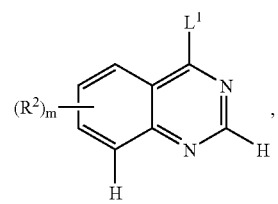

wherein $R^2$ and m are as defined in claim 1 and $L^1$ is a displaceable moiety, with a compound of the formula IV:

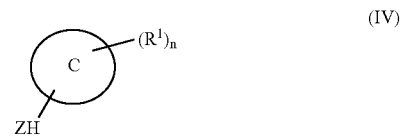

(b) compounds of formula II and salts thereof wherein at least one $R^2$ is $R^5X^1$ wherein $X^1$ is —O—, —S—, —OCO— or —NR$^{10}$—, wherein $R^{10}$ independently represents hydrogen, $C_{1-3}$alkyl or $C_{1-3}$alkoxy$C_{2-3}$alkyl may be prepared by the reaction of a compound of the formula V:

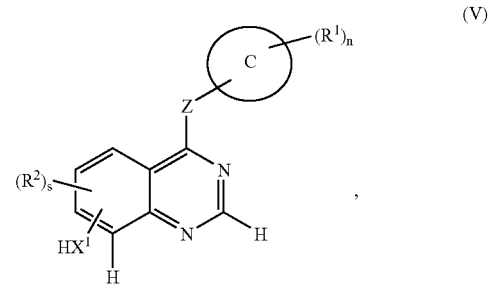

wherein $X^1$ is as defined herein in this section and s is an integer from 0 to 2 with a compound of formula VI:

wherein $L^1$ is as defined herein;

(c) compounds of the formula II and salts thereof wherein at least one $R^2$ is $R^5X^1$ wherein $X^1$ is —O—, —S—, —OCO— or —NR$^{10}$—, wherein $R^{10}$ represents hydrogen, $C_{1-3}$alkyl or $C_{1-3}$alkoxy$C_{2-3}$alkyl may be prepared by the reaction of a compound of the formula VII:

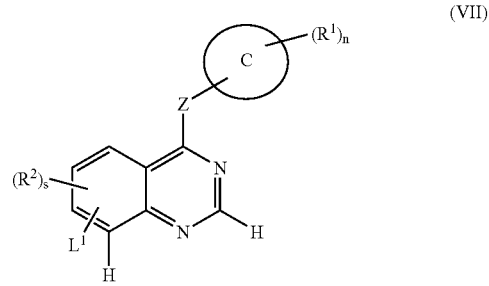

with a compound of the formula VIII:

$$R^5—X^1—H \quad (VIII),$$

wherein s and $L^1$ are as defined herein and $X^1$ is as defined herein in this section;

(d) compounds of the formula II and salts thereof wherein at least one $R^2$ is $R^5X^1$ wherein $X^1$ is as defined in claim 1 and $R^5$ is $C_{1-5}$alkyl$R^{62}$, wherein $R^{62}$ is selected from one of the following nine groups:
1) $X^{10}C_{1-3}$alkyl (wherein $X^{10}$ represents —O—, —S—, —SO$_2$—, —NR$^{63}$CO— or —NR$^{64}$SO$_2$—, wherein $R^{63}$ and $R^{64}$ which may be the same or different are each hydrogen, $C_{1-3}$alkyl or $C_{1-3}$alkoxy$C_{2-3}$alkyl;
2) NR$^{65}$R$^{66}$, wherein $R^{65}$ and $R^{66}$ which may be the same or different are each hydrogen, $C_{1-3}$-alkyl or $C_{1-3}$alkoxy$C_{2-3}$alkyl;
3) $X^{11}C_{1-5}$alkyl$X^5R^{22}$, wherein $X^{11}$ represents —O—, —S—, —SO$_2$—, —NR$^{67}$CO—, —NR$^{68}$SO$_2$— or —NR$^{69}$—, wherein $R^{67}$, $R^{68}$, and $R^{69}$ which may be the same or different are each hydrogen, $C_{1-3}$alkyl or $C_{1-3}$alkoxy$C_{2-3}$alkyl and $X^5$ and $R^{22}$ are as defined in claim 1;
4) $R^{59}$, wherein $R^{59}$ is as defined in claim 1;
5) $X^{12}R^{29}$, wherein $X^{12}$ represents —O—, —S—, —SO$_2$—, —NR$^{70}$CO—, —NR$^{71}$SO$_2$—, or —NR$^{72}$—, wherein $R^{70}$, $R^{71}$, and $R^{72}$ which may be the same or different are each hydrogen, $C_{1-3}$alkyl or $C_{1-3}$alkoxy$C_{2-3}$alkyl and $R^{29}$ is as defined in claim 1;
6) $X^{13}C_{1-2}$alkyl$R^{29}$, wherein $X^{13}$ represents —O—, —S—, —SO$_2$—, —NR$^{73}$CO—, —NR$^{74}$SO$_2$— or —NR$^{75}$—, wherein $R^{73}$, $R^{74}$ and $R^{75}$ each independently represents hydrogen, $C_{1-3}$alkyl or $C_{1-3}$alkoxy$C_{2-3}$alkyl, and $R^{29}$ is as defined in claim 1;
7) $R^{29}$, wherein $R^{29}$ is as defined in claim 1;
8) $X^{14}C_{1-3}$alkyl$R^{28}$, wherein $X^{14}$ represents —O—, —S—, —SO$_2$—, —NR$^{76}$CO—, —NR$^{77}$SO$_2$— or —NR$^{78}$—, wherein $R^{76}$, $R^{77}$ and $R^{78}$ each independently represents hydrogen, $C_{1-3}$alkyl or $C_{1-3}$alkoxy$C_{2-3}$alkyl, and $R^{28}$ is as defined in claim 1; and
9) $R^{54}C_{1-3}$alkyl$X^9R^{55}$, wherein $R^{54}$, $R^{55}$ and $X^9$ are as defined in claim 1;

may be prepared by reacting a compound of the formula IX:

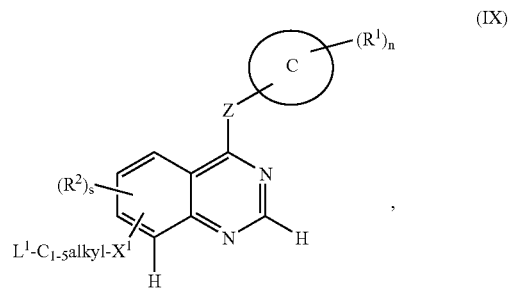

wherein a and $L^1$ are as defined herein) with a compound of the formula X:

$$R^{62}—H \quad (X),$$

wherein $R^{62}$ is as defined herein);

(e) compounds of the formula II and salts thereof wherein one or more of the substituents $(R^2)_m$ is represented by —NR$^{79}$R$^{80}$, where one (and the other is hydrogen) or both of $R^{79}$ and $R^{80}$ are $C_{1-3}$alkyl, may be prepared by the reaction of compounds of formula II wherein the substituent $(R^2)_m$ is an amino group and an alkylating agent;

(f) compounds of the formula II and salts thereof wherein $X^1$ is —SO— or —SO$_2$— may be prepared by oxidation from the corresponding compound in which $X^1$ is —S— or —SO—;

and optionally forming a salt of a compound of formula II by reaction of the compound obtained with an acid or base whereby to obtain the desired salt.

* * * * *